US011723809B2

(12) United States Patent
Askem et al.

(10) Patent No.: US 11,723,809 B2
(45) Date of Patent: Aug. 15, 2023

(54) WOUND TREATMENT APPARATUSES AND METHODS WITH NEGATIVE PRESSURE SOURCE INTEGRATED INTO WOUND DRESSING

(71) Applicant: Smith & Nephew PLC, Watford (GB)

(72) Inventors: Ben Alan Askem, Brough (GB); Victoria Beadle, Hull (GB); John Philip Gowans, Hessle (GB); Mark Hesketh, Royston (GB); Allan Kenneth Frazer Grugeon Hunt, Beverley (GB); William Kelbie, Inverness (GB); Damyn Musgrave, Cottenham (GB); Joseph William Robinson, Papworth Everard (GB)

(73) Assignee: Smith & Nephew PLC, Watford (GB)

( * ) Notice: Subject to any disclaimer, the term of this patent is extended or adjusted under 35 U.S.C. 154(b) by 1198 days.

(21) Appl. No.: 16/082,884

(22) PCT Filed: Mar. 6, 2017

(86) PCT No.: PCT/EP2017/055225
§ 371 (c)(1),
(2) Date: Sep. 6, 2018

(87) PCT Pub. No.: WO2017/153357
PCT Pub. Date: Sep. 14, 2017

(65) Prior Publication Data
US 2019/0021911 A1 Jan. 24, 2019

Related U.S. Application Data

(60) Provisional application No. 62/327,537, filed on Apr. 26, 2016, provisional application No. 62/305,926,
(Continued)

(51) Int. Cl.
*A61F 13/00* (2006.01)
*A61M 1/00* (2006.01)
(Continued)

(52) U.S. Cl.
CPC .... *A61F 13/00068* (2013.01); *A61F 13/0216* (2013.01); *A61M 1/782* (2021.05);
(Continued)

(58) Field of Classification Search
CPC .......... A61F 13/00068; A61F 13/0216; A61M 1/782; A61M 1/784; A61M 1/80;
(Continued)

(56) References Cited

U.S. PATENT DOCUMENTS

| 3,874,387 A | 4/1975 | Barbieri |
| 4,224,941 A | 9/1980 | Stivala |

(Continued)

FOREIGN PATENT DOCUMENTS

| CN | 201664463 U | 12/2010 |
| DE | 198 44 355 | 4/2000 |

(Continued)

OTHER PUBLICATIONS

International Search Report and Written Opinion, re PCT Application No. PCT/EP2017/055225, dated Aug. 3, 2017.
(Continued)

*Primary Examiner* — Jessica Arble
(74) *Attorney, Agent, or Firm* — Knobbe, Martens, Olson & Bear, LLP

(57) ABSTRACT

Disclosed embodiments relate to apparatuses and methods for wound treatment. In some embodiments, a negative pressure source is incorporated into a wound dressing apparatus so that the wound dressing and the negative pressure source are part of an integral or integrated wound dressing structure that applies the wound dressing and the negative
(Continued)

pressure source simultaneously to a patient's wound. The negative pressure source and/or electronic components may be positioned between a wound contact layer and a cover layer of the wound dressing. The negative pressure source and/or electronic components may be separated and/or partitioned from an absorbent area of the dressing. A switch may be integrated with the wound dressing to control operation of the wound dressing apparatus. A connector may be direct air from an outlet of the negative pressure source to the environment. A non-return valve may inhibit back flow of air into the wound dressing.

21 Claims, 53 Drawing Sheets

Related U.S. Application Data filed on Mar. 9, 2016, provisional application No. 62/304,910, filed on Mar. 7, 2016, provisional application No. 62/304,790, filed on Mar. 7, 2016.

(51) Int. Cl.
*A61M 39/24* (2006.01)
*A61F 13/02* (2006.01)

(52) U.S. Cl.
CPC .............. *A61M 1/784* (2021.05); *A61M 1/80* (2021.05); *A61M 1/962* (2021.05); *A61M 39/24* (2013.01); *A61M 1/74* (2021.05); *A61M 2039/2433* (2013.01); *A61M 2205/3344* (2013.01)

(58) Field of Classification Search
CPC .......... A61M 39/24; A61M 2039/2433; A61M 2039/244; A61M 2039/246; F04B 39/1073; F04B 53/1037; F04B 53/16; F16K 15/16
See application file for complete search history.

(56) References Cited

U.S. PATENT DOCUMENTS

| | | |
|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,881,772 A | 3/1999 | Bennett |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,216,651 B2 | 5/2007 | Argenta et al. |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,776,028 B2 | 8/2010 | Miller et al. |
| 7,779,625 B2 | 8/2010 | Joshi et al. |
| D625,422 S | 10/2010 | Arbesman et al. |
| 7,837,673 B2 | 11/2010 | Vogel |
| 7,838,717 B2 | 11/2010 | Haggstrom et al. |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radi et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,062,273 B2 | 11/2011 | Weston |
| 8,080,702 B2 | 12/2011 | Blott et al. |
| 8,092,441 B2 | 1/2012 | Sugito |
| 8,118,794 B2 | 2/2012 | Weston et al. |
| 8,158,844 B2 | 4/2012 | Mcneil |
| 8,167,869 B2 | 5/2012 | Wudyka |
| 8,207,392 B2 | 6/2012 | Haggstrom et al. |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,444,612 B2 | 5/2013 | Patel et al. |
| 8,449,508 B2 | 5/2013 | Coulthard et al. |
| 8,460,255 B2 | 6/2013 | Joshi et al. |
| 8,500,776 B2 | 8/2013 | Ebner |
| 8,545,464 B2 | 10/2013 | Weston |
| 8,545,466 B2 | 10/2013 | Andresen et al. |
| 8,569,566 B2 | 10/2013 | Blott et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,628,505 B2 | 1/2014 | Weston |
| 8,641,691 B2 | 2/2014 | Fink |
| 8,641,693 B2 | 2/2014 | Locke et al. |

(56) References Cited

U.S. PATENT DOCUMENTS

| | | |
|---|---|---|
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,829,263 B2 | 9/2014 | Haggstrom et al. |
| 8,870,837 B2 | 10/2014 | Locke et al. |
| 8,915,895 B2 | 12/2014 | Jaeb et al. |
| 8,961,496 B2 | 2/2015 | Locke et al. |
| 8,974,429 B2 | 3/2015 | Gordon et al. |
| 9,050,209 B2 | 6/2015 | Coulthard et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,168,330 B2 | 10/2015 | Joshi et al. |
| 9,198,802 B2 | 12/2015 | Robinson et al. |
| 9,220,822 B2 | 12/2015 | Hartwell et al. |
| 9,259,558 B2 | 2/2016 | Tsai |
| 9,265,665 B2 | 2/2016 | Robinson et al. |
| 9,265,867 B2 | 2/2016 | Coulthard et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,452,088 B2 | 9/2016 | Shulman et al. |
| 9,452,245 B2 | 9/2016 | Jaeb et al. |
| 9,560,975 B2 | 2/2017 | Mei et al. |
| 9,629,986 B2 | 4/2017 | Patel et al. |
| D787,690 S | 5/2017 | Mackay et al. |
| 9,669,138 B2 | 6/2017 | Joshi et al. |
| 9,737,649 B2 | 8/2017 | Begin et al. |
| 9,770,368 B2 | 9/2017 | Robinson et al. |
| 9,795,725 B2 | 10/2017 | Joshi et al. |
| 9,814,811 B2 | 11/2017 | Aalders et al. |
| 9,844,475 B2 | 12/2017 | Hartwell |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,016,309 B2 | 7/2018 | Hartwell |
| 10,016,544 B2 | 7/2018 | Coulthard et al. |
| 2003/0212357 A1 | 11/2003 | Pace |
| 2004/0064132 A1 | 4/2004 | Boehringer et al. |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0213527 A1 | 9/2006 | Argenta et al. |
| 2006/0259102 A1 | 11/2006 | Slatkine |
| 2007/0055209 A1 | 3/2007 | Patel et al. |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2008/0021356 A1 | 1/2008 | Castello Escude et al. |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2011/0092927 A1 | 4/2011 | Wilkes et al. |
| 2011/0112492 A1 | 5/2011 | Bharti et al. |
| 2011/0137271 A1 | 6/2011 | Andresen et al. |
| 2011/0213319 A1 | 9/2011 | Blott et al. |
| 2011/0224631 A1 | 9/2011 | Simmons |
| 2011/0292623 A1 | 12/2011 | Stanley |
| 2011/0305736 A1 | 12/2011 | Wieland et al. |
| 2012/0016323 A1* | 1/2012 | Robinson ............... A61M 1/90 604/319 |
| 2012/0041401 A1 | 2/2012 | Chao et al. |
| 2012/0059294 A1 | 3/2012 | Schubert et al. |
| 2012/0109034 A1 | 5/2012 | Locke et al. |
| 2012/0109083 A1* | 5/2012 | Coulthard ........... A61F 13/0216 604/319 |
| 2013/0090615 A1 | 4/2013 | Jaeb et al. |
| 2013/0102979 A1 | 4/2013 | Coulthard et al. |
| 2013/0215638 A1 | 8/2013 | Dabov et al. |
| 2013/0331823 A1* | 12/2013 | Askem ................... F04B 53/10 417/44.1 |
| 2014/0005618 A1 | 1/2014 | Locke et al. |
| 2014/0100536 A1 | 4/2014 | Angel |
| 2014/0330227 A1 | 11/2014 | Coulthard et al. |
| 2014/0343518 A1 | 11/2014 | Riesinger |
| 2015/0057625 A1 | 2/2015 | Coulthard et al. |
| 2015/0065965 A1 | 3/2015 | Haggstrom et al. |
| 2015/0174304 A1 | 6/2015 | Askem et al. |
| 2015/0202354 A1 | 7/2015 | Wall |
| 2015/0224238 A1 | 8/2015 | Hartwell |
| 2015/0258256 A1 | 9/2015 | Jaeb et al. |
| 2015/0250931 A1 | 10/2015 | Bharti et al. |
| 2016/0015873 A1 | 1/2016 | Robinson et al. |
| 2016/0058927 A1 | 3/2016 | Weston |
| 2016/0166438 A1 | 6/2016 | Rovaniemi |
| 2016/0199546 A1 | 7/2016 | Chao |
| 2016/0206793 A1 | 7/2016 | Robinson et al. |
| 2016/0242964 A1 | 8/2016 | Rapp et al. |
| 2016/0271305 A1 | 9/2016 | Kurihara et al. |
| 2016/0361473 A1 | 12/2016 | Robinson et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0304510 A1 | 10/2017 | Askem et al. |
| 2017/0319761 A1 | 11/2017 | Locke et al. |
| 2017/0326277 A1 | 11/2017 | Huang |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0200414 A1 | 7/2018 | Askem et al. |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0125943 A1 | 5/2019 | Askem et al. |
| 2019/0143007 A1 | 5/2019 | Askem et al. |
| 2019/0192350 A1 | 6/2019 | Gowans et al. |
| 2019/0282737 A1 | 9/2019 | Beadle et al. |
| 2020/0022846 A1 | 1/2020 | Beadle et al. |

FOREIGN PATENT DOCUMENTS

| | | |
|---|---|---|
| EP | 0512543 A2 | 11/1992 |
| EP | 1411874 A1 | 4/2004 |
| EP | 1455701 B1 | 3/2006 |
| EP | 1448261 B1 | 2/2007 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |

(56) References Cited

FOREIGN PATENT DOCUMENTS

| | | |
|---|---|---|
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2 345 437 | 4/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2945584 B1 | 7/2016 |
| EP | 2293749 B1 | 8/2016 |
| EP | 3 072 542 | 9/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2282788 B1 | 12/2016 |
| EP | 2462956 B2 | 3/2017 |
| EP | 3139878 A1 | 3/2017 |
| EP | 1587502 B1 | 5/2017 |
| EP | 1587554 B1 | 5/2017 |
| EP | 2731563 B1 | 5/2017 |
| EP | 2968871 B1 | 7/2017 |
| EP | 2632613 B1 | 8/2017 |
| EP | 2888478 B1 | 8/2017 |
| EP | 2937107 B1 | 8/2017 |
| EP | 2967627 B1 | 8/2017 |
| EP | 3062751 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 2244756 B1 | 12/2019 |
| EP | 2968702 B1 | 12/2019 |
| FR | 2939320 A1 | 6/2010 |
| GB | 2511523 A | 9/2014 |
| JP | H04354722 A | 12/1992 |
| RU | 131622 U1 | 8/2013 |
| WO | WO 1996/05873 | 2/1996 |
| WO | WO 2007/030601 | 3/2007 |
| WO | WO 2009/098696 | 8/2009 |
| WO | WO-2009120951 A2 | 10/2009 |
| WO | WO-2011037524 A1 | 3/2011 |
| WO | WO 2011/130570 | 10/2011 |
| WO | WO 2011/135285 | 11/2011 |
| WO | WO-2011144888 A1 | 11/2011 |
| WO | WO-2013007973 A2 | 1/2013 |
| WO | WO 2013/136181 | 9/2013 |
| WO | WO 2013/171585 | 11/2013 |
| WO | WO 2013/175306 | 11/2013 |
| WO | WO 2014/099709 | 6/2014 |
| WO | WO-2014145014 A1 | 9/2014 |
| WO | WO 2016/103031 | 6/2016 |
| WO | WO-2016126560 A1 | 8/2016 |
| WO | WO 2016/174048 | 11/2016 |
| WO | WO 2016/182977 | 11/2016 |
| WO | WO 2017/079174 | 5/2017 |
| WO | WO 2017/153357 | 9/2017 |
| WO | WO 2017/186771 | 11/2017 |
| WO | WO 2017/191154 | 11/2017 |
| WO | WO-2017196888 A1 | 11/2017 |
| WO | WO-2018056060 A1 | 3/2018 |
| WO | WO-2018115461 A1 | 6/2018 |
| WO | WO-2018156730 A1 | 8/2018 |
| WO | WO-2018158250 A1 | 9/2018 |
| WO | WO-2018164803 A1 | 9/2018 |

OTHER PUBLICATIONS

Invitation to Pay Additional Fees and Partial Search Report, re PCT Application No. PCT/EP2017/055225, dated May 9, 2017.
International Preliminary Report on Patentability for Application No. PCT/EP2017/055225, dated Sep. 20, 2018, 14 pages.

\* cited by examiner

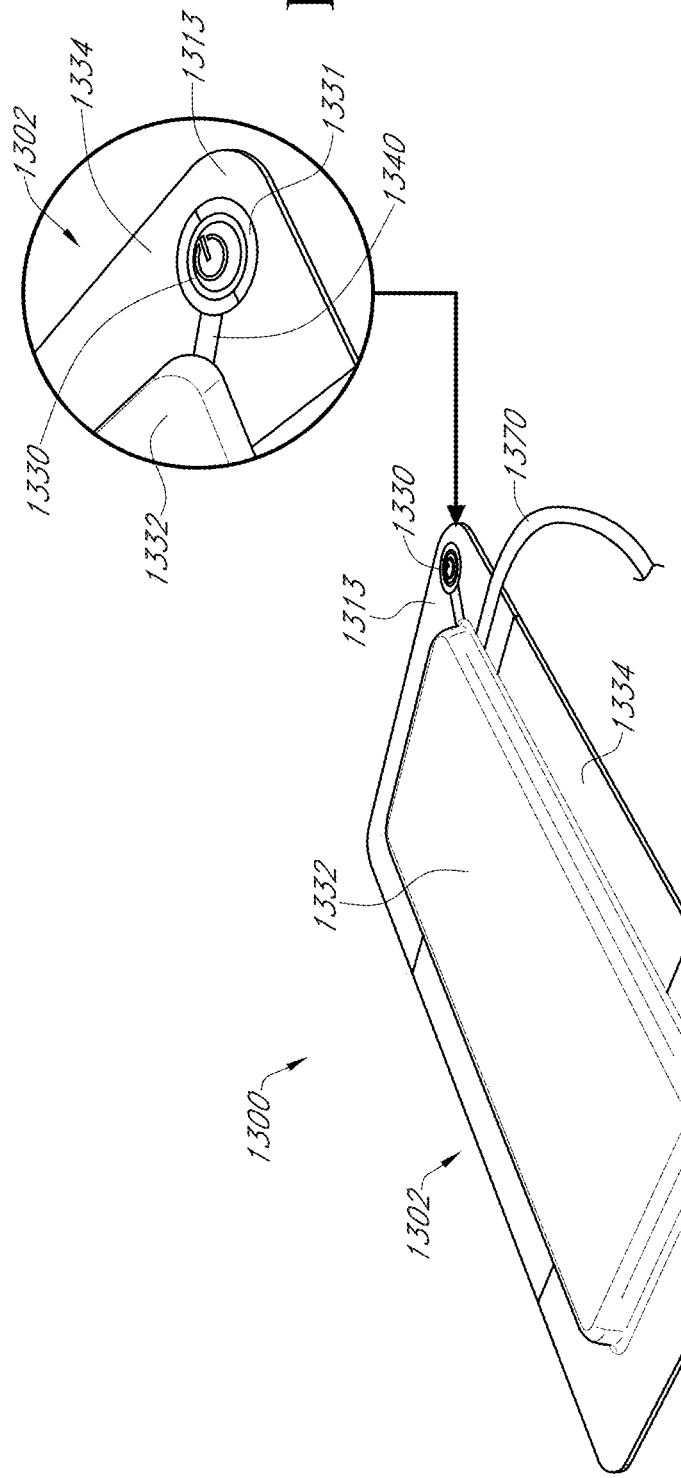

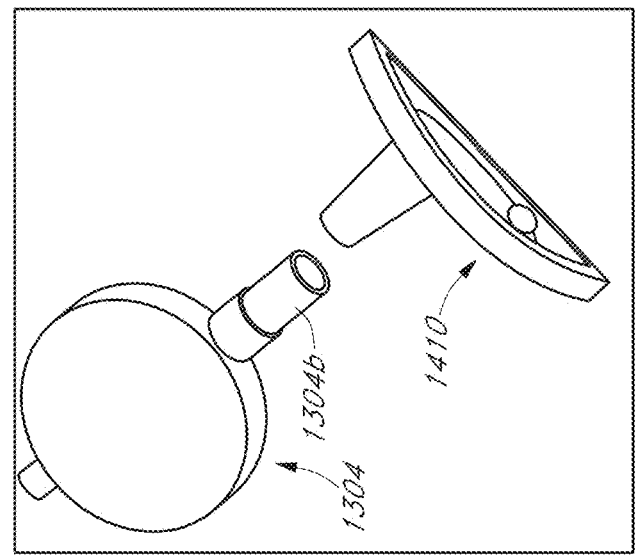
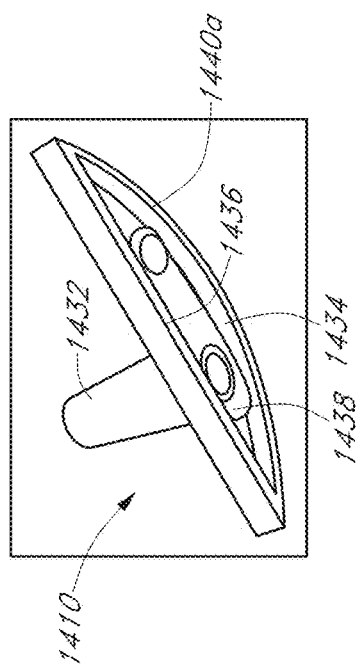
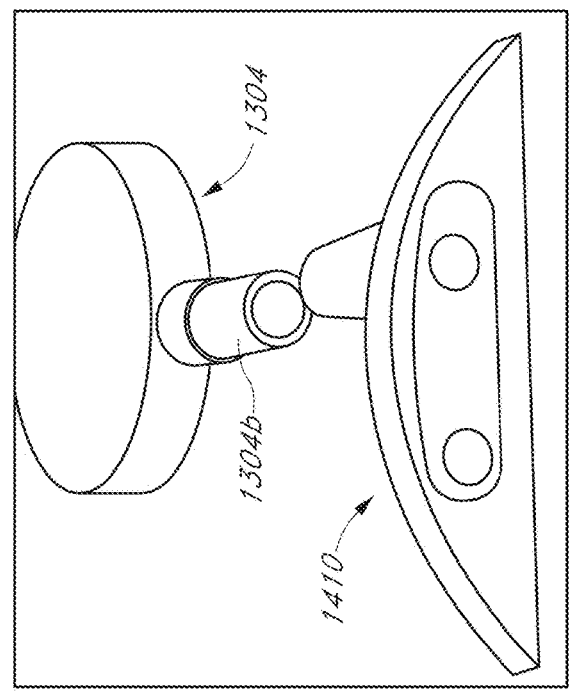
FIG. 36C
FIG. 36A
FIG. 36B

WOUND TREATMENT APPARATUSES AND METHODS WITH NEGATIVE PRESSURE SOURCE INTEGRATED INTO WOUND DRESSING

CROSS-REFERENCE TO RELATED APPLICATIONS

This application is a U.S. national stage application of International Patent Application No. PCT/EP2017/055225, filed on Mar. 6, 2017, which claims priority to U.S. Provisional Application No. 62/304790, filed Mar. 7, 2016, U.S. Provisional Application No. 62/305926, filed Mar. 9, 2016, U.S. Provisional Application No. 62/304910, filed Mar. 7, 2016, and U.S. Provisional Application No. 62/327537, filed Apr. 26, 2016, the entireties of each of which are hereby incorporated by reference.

BACKGROUND

Technical Field

Embodiments described herein relate to apparatuses, systems, and methods the treatment of wounds, for example using dressings in combination with negative pressure wound therapy.

Description of the Related Art

Prior art dressings for use in negative pressure have included a negative pressure source located in a remote location form the wound dressing. Further, when used, wound exudate may soak into the dressing, and the moisture from the wound has made it difficult to incorporate electronic components into the dressing.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein. In some embodiments, a negative pressure source is incorporated into a wound dressing apparatus so that the wound dressing and the negative pressure source are part of an integral or integrated wound dressing structure that applies the wound dressing and the negative pressure source simultaneously to a patient's wound. The negative pressure source and/or electronic components may be positioned between a wound contact layer and a cover layer of the wound dressing. The negative pressure source and/or electronic components may be separated and/or partitioned from an absorbent area of the dressing. A switch may be integrated with the wound dressing to control operation of the wound dressing apparatus. A connector may be direct air from an outlet of the negative pressure source to the environment. A non-return valve may inhibit back flow of air into the wound dressing. These and other embodiments as described herein are directed to overcoming particular challenges involved with incorporating a negative pressure source and/or electronic components into a wound dressing.

In some aspects, a wound dressing apparatus comprises a wound contact layer configured to be positioned in contact with a wound, a first area over the wound contact layer comprises a lower spacer layer and an absorbent layer, a second area over the wound contact layer comprising a plurality of spacer layers and a negative pressure source and/or electronic components positioned within or between the plurality of spacer layers, wherein the first area is positioned adjacent to the second area and separated by a partition, an upper spacer layer configured to cover the first area and the second area and to allow air to be communicated between the first area and second area around the partition, and a cover layer configured to cover and form a seal over the wound contact layer, the upper spacer layer, the first area, and the second area.

The apparatus of the preceding paragraph may also include any combination of the following features described in this paragraph, among others described herein. The plurality of spacer layers in the second area can include a third spacer layer beneath the negative pressure source and/or electronic components and a fourth spacer layer positioned above the negative pressure source and/or electronic components, wherein the fourth spacer layer comprises one or more cutouts or recesses configured to receive the negative pressure source and/or electronic components. The partition can include a non-porous dam. The apparatus can comprise one or more user interface components configured to allow a user to operate the negative pressure source and/or electronic components.

In some aspects, a wound dressing apparatus can comprise a wound dressing configured to be positioned over a wound site, a negative pressure source disposed on or positioned within the wound dressing, and a switch integrated with the wound dressing configured to control operation of the wound dressing apparatus.

The apparatus of the preceding paragraph may also include any combination of the following features described in this paragraph, among others described herein. The switch can be at least one of positioned within, disposed on, or embedded in the wound dressing. The wound dressing can comprise a wound dressing body and a wound dressing border, the wound dressing border extending along at least of a portion of a perimeter defined around the wound dressing body. The switch can be integrated with the wound dressing body or the wound dressing border. The switch can be at least one of positioned within, disposed on, or embedded in the wound dressing body or the wound dressing border. The wound dressing body and the wound dressing border can comprise a top layer and a bottom layer, the top layer comprising a cover layer and the bottom layer comprising a wound contact layer, the switch being integrated with the wound dressing proximally adjacent at least one of the top layer and the bottom layer. The wound dressing body or the wound dressing border can comprise a flexiboard layer beneath the switch to dissipate and/or inhibit the transfer of a compression force to the wound site when the switch is actuated. The switch can be configured to be actuated by pressing the switch in a first direction with a finger. The wound dressing can comprise a tab that extends from the wound dressing border, the switch being integrated with the tab. The switch can be at least one of positioned within, disposed on, or embedded in the tab. The tab can be configured to be lifted by a user so that the switch can be actuated by the user by applying force to the switch in two opposing directions on opposite or different sides of the tab. The wound dressing can comprise a joint between the tab and the wound dressing border to facilitate movement of the tab without applying force to the wound dressing body or the wound dressing border, the tab being configured to rotate about the joint when a user moves the tab. The apparatus can include one or more indicators configured to indicate one or more statuses of the wound dressing apparatus. The one or more indicators can comprise one or more visual indicators. The one or more visual indicators can comprise one or more light emitting diodes (LEDs). The one or more indicators can be configured to indicate a battery level of the wound dressing apparatus. The one or more indicators can extend around the switch. The one or more indicators can circumferentially extend around the switch. The switch can be positioned in a sub-flush position relative to the one or more indicators to inhibit accidental or inadvertent actuation of the switch. The switch can be selectively operable by a user to control operation of the negative pressure source. The switch can be selectively operable by a user to turn on and turn off the negative pressure source. The switch can be electrically connected to the negative pressure source. The negative pressure source can be a micro pump.

In some aspects, a wound dressing apparatus can comprise a wound dressing configured to be positioned over a wound site, a negative pressure source disposed on or positioned within the wound dressing, the negative pressure source comprising an inlet and an outlet, the negative pressure source being configured to apply negative pressure to the wound site via the inlet and being further configured to remove air from the wound dressing via the outlet, and a connector comprising first and second ends and a flow path therebetween, wherein the first end is in fluid communication with the outlet and the second end is open to an environment outside the wound dressing, wherein a portion of the flow path extends through an opening defined in the wound dressing, the flow path being configured to direct air from the outlet to the environment.

The apparatus of the preceding paragraph may also include any combination of the following features described in this paragraph, among others described herein. The opening in the wound dressing can be defined on a top layer of the wound dressing. The top layer can comprise a moisture vapor permeable film. The opening in the wound dressing can be defined between a top layer and a bottom layer of the wound dressing. The opening in the wound dressing can be defined through an edge of the wound dressing between a top layer and a bottom layer of the wound dressing. The top layer can comprise a moisture vapor permeable film and the bottom layer comprises a wound contact layer. The connector can comprise a spacer that extends between a first and second portion of the connector, the spacer being configured to resist collapse of the connector when the connector is compressed. The first and second portions of the connector can comprise the first and second ends of the connector. The spacer can be enveloped in a film to form a gas tight seal with the wound dressing. The spacer can comprise a length of 3D fabric material. The film can be a plastic film. The film can be Versapore film having a pore size diameter of about 2 μm. The connector can form a gas tight seal with the wound dressing. The connector can form a gas tight seal with the outlet of the negative pressure source. The connector can be configured to resist collapse, thereby inhibiting occlusion of the connector when the wound dressing is subjected to compressive forces. The connector can be configured to inhibit the ingress of water, foreign bodies, dirt, or bacteria through the opening in the wound dressing. The wound dressing apparatus further can comprise a tube interposed between the outlet and the connector, the tube being coupled to the outlet and the connector. The tube can be configured to extend the connector such that the connector is positioned outside of the wound dressing after the tube passes through the opening in the wound dressing.

In some aspects, a wound dressing apparatus can comprise a wound dressing configured to be positioned over a wound site, a negative pressure source disposed on or positioned within the wound dressing, the negative pressure source comprising an inlet and an outlet and being operable to apply negative pressure to the wound site, and a non-return valve in fluid communication with the outlet, the non-return valve being configured to inhibit back flow of air into the wound dressing.

The apparatus of the preceding paragraph may also include any combination of the following features described in this paragraph, among others described herein. The non-return valve can be configured to inhibit back flow of air into the wound dressing through the outlet. The non-return valve can be connected to the outlet. The non-return valve can comprise a first end in fluidic communication with the outlet and a second end in fluid communication with an exhaust component, the exhaust component being configured to direct air from the outlet to the environment. The first end of the non-return valve can be connected to the outlet and the second end of the non-return valve is connected to the exhaust component. The non-return valve is at least partially disposed in the outlet. The apparatus can include an exhaust system having first and second ends, wherein the exhaust system is interposed between the outlet and the non-return valve such that the first end is connected to the outlet and the second end is connected to the non-return valve. The apparatus can include an exhaust system, wherein the non-return valve is at least partially integrated with the exhaust system. The non-return valve can be at least partially integrated with the exhaust system at an end of the exhaust system. The non-return valve can be integrated with the wound dressing. The non-return valve can be positioned within and/or embedded in the wound dressing. The non-return valve can comprise a size configured to fit within the wound dressing. The non-return valve can have a height that is less than a thickness of the wound dressing. The non-return valve can have a low cracking pressure and a low resistance to out flow. The non-return valve can have a cracking pressure of less than 500 Pa for a nominal flow rate of about 1 mL/min through the apparatus. The non-return valve can have an out flow resistance of less than 30 mL/min as measured with a nominally fixed vacuum of 10.7 kPa below atmosphere. The non-return valve can provide a resistance to air flowing out of the wound dressing apparatus of less than 100 mL/min as measured with a nominally fixed vacuum of 10.7 kPa below atmosphere. The negative pressure source and the non-return valve together can allow air to leak into the wound dressing apparatus via the outlet at a negligible rate of less than 2.0 mL/min. The non-return valve can be a mechanical valve that is self-activated. The non-return valve can comprise a duckbill valve. The non-return valve can comprise a reed valve. The reed valve can comprise a 75 micron thick polyester reed valve. The non-return valve can comprise a cavity with an inlet port and an outlet port and a reed at least partially disposed in the cavity. The non-return valve can comprise a crescent shape. The crescent shape can be defined by a housing having a first curved surface that intersects a second surface. The second surface can be flat. The second surface can be curved, the second surface can have a radius of curvature that is greater than a radius of curvature of the first curved surface. The second surface can be semi-rigid or flexible such that it is configured to conform to a surface of the wound site. The non-return valve can comprise a crescent shape, wherein the reed can comprise a rectangular shape with circular ends. The non-return valve can comprise a crescent shape, wherein the reed can include a curved portion. The negative pressure source can be a micro pump. The apparatus can include a controller configured to control the operation of the micro pump to apply negative pressure to the wound site.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIGS. 28B-28C illustrate a perspective view of an embodiment of a wound dressing system with a switch embedded into a wound dressing border;

FIGS. 30C-3E show embodiments of wound dressings with a switch integrated into the wound dressing border;

FIGS. 36A-36C illustrate various views of embodiments of a non-return valve having a crescent shape for integration into a wound dressing;

DETAILED DESCRIPTION

Figure 1:
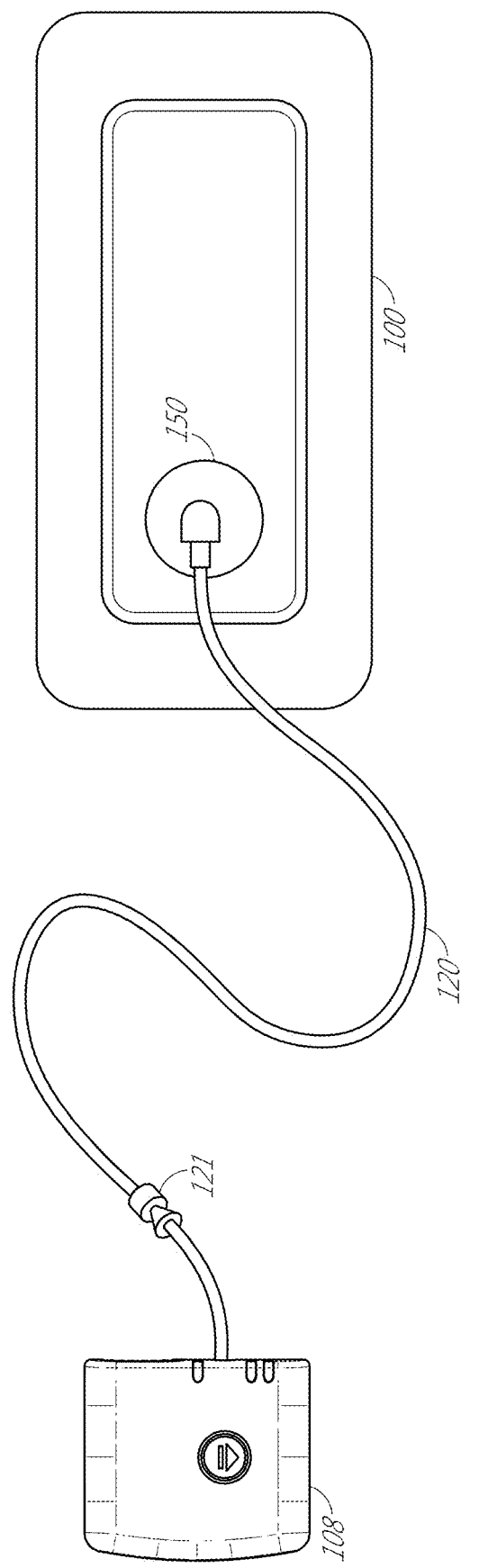
FIG. 1 illustrates an embodiment of a topical negative pressure wound treatment apparatus comprising a wound dressing in combination with a pump.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated and considered to be part of this specification, that is directed to embodiments, methods of manufacture, and wound dressing components and wound treatment apparatuses that may be used in combination or in addition to the embodiments described herein. Additionally, embodiments of the wound dressings, wound treatment apparatuses and methods described herein may also be used in combination or in addition to those described in U.S. Provisional Application No. 61/650,904, filed May 23, 2012, titled "APPARATUSES AND METHODS FOR NEGATIVE PRESSURE WOUND THERAPY," International Application No. PCT/IB2013/001469, filed May 22, 2013, titled "APPARATUSES AND METHODS FOR NEGATIVE PRESSURE WOUND THERAPY," and published as WO 2013/175306 on Nov. 28, 2013, U.S. patent application Ser. No. 14/418874, filed Jan. 30, 2015, published as U.S. Publication No. 2015/0216733, published Aug. 6, 2015, titled "WOUND DRESSING AND METHOD OF TREATMENT," U.S. patent application Ser. No. 14/418908, filed Jan. 30, 2015, published as U.S. Publication No. 2015/0190286, published Jul. 9, 2015, titled "WOUND DRESSING AND METHOD OF TREATMENT," U.S. patent application Ser. No. 14/658,068, filed Mar. 13, 2015, U.S. Application No. 2015/0182677, published Jul. 2, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21 2011, published as US2011/0282309, titled "WOUND DRESSING AND METHOD OF USE," and which is hereby incorporated by reference in its entirety, including further details relating to embodiments of wound dressings, the wound dressing components and principles, and the materials used for the wound dressings.

FIG. 1 illustrates an embodiment of a TNP wound treatment comprising a wound dressing 100 in combination with a pump 108. As stated above, the wound dressing 100 can be any wound dressing embodiment disclosed herein including without limitation dressing embodiment 100 or have any combination of features of any number of wound dressing embodiments disclosed herein. Here, the dressing 100 may be placed over a wound, and a conduit 120 may then be connected to the port 150, although in some embodiments the dressing 100 may be provided with at least a portion of the conduit 120 preattached to the port 150. Preferably, the dressing 100 is provided as a single article with all wound dressing elements (including the port 150) pre-attached and integrated into a single unit. The wound dressing 100 may then be connected, via the conduit 120, to a source of negative pressure such as the pump 108. The pump 108 can be miniaturized and portable, although larger conventional pumps may also be used with the dressing 100. In some embodiments, the pump 108 may be attached or mounted onto or adjacent the dressing 100. A connector 121 may also be provided so as to permit the conduit 120 leading to the wound dressing 100 to be disconnected from the pump, which may be useful for example during dressing changes.

Figure 2:
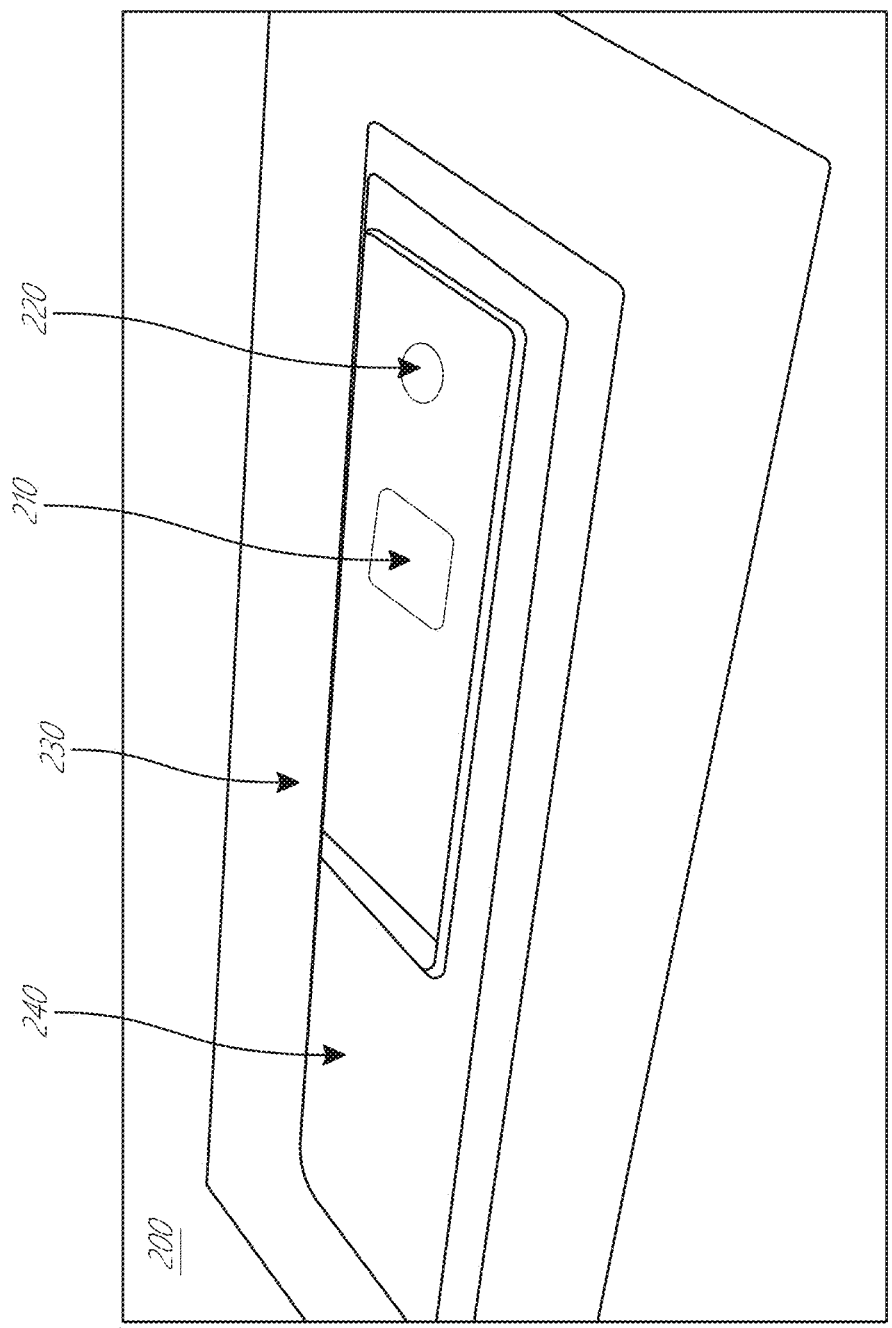
FIG. 2 illustrates an embodiment of a source of negative pressure and battery integrated on top of a dressing layer.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. As is illustrated in FIG. 2, the source of negative pressure and battery can be included within the integrated dressing 200. Although FIG. 2 illustrates the source of negative pressure and battery 210 placed on top of the dressing layer 240 (such as an absorbent layer), the source of negative pressure and one or more components can be incorporated into the dressing differently. The source of negative pressure and the one or more components need not all be incorporated into the dressing in the same manner. For example, a pressure sensor can be positioned below (or closer to the wound) the layer 240 while the source of negative pressure can be positioned on top of the layer 240. FIGS. 6A-6D illustrate alternative arrangements for incorporating the negative pressure source and the one or more components into the dressing. The integrated dressing 200 illustrated in FIG. 2 includes a cover layer 230 that includes for securing the dressing to skin surrounding the wound. The cover layer 230 can be formed of substantially fluid impermeable material, such as film. The cover layer can include an adhesive for securing the dressing to the surrounding skin or wound contact layer.

In some embodiments, the dressing can include the power source and other components, such as electronics, on and/or incorporated into the dressing and can utilize a wound contact layer and a first spacer layer within the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound. The first spacer layer assists in distributing negative pressure over the wound site and facilitating transport of wound exudate and fluids into the wound dressing. Further, an absorbent layer (such as layer 240) for absorbing and retaining exudate aspirated from the wound can be utilized. In some embodiments, the absorbent includes a shaped form of a superabsorber layer with recesses or compartments for the pump, electronics, and accompanying components. These layers can be covered with one layer of a film or cover layer (or a first cover layer). The first cover layer can include a filter set that can be positioned within one of the recesses. The filter can be configured to align with one of the at least one recesses of the absorbent layer, and the filter can include hydrophobic material to protect the pump and/or other components from liquid exudates. The filter can block fluids while permitting gases to pass through. The pump, electronics, switch and battery can be positioned on top of the first cover layer. Another section of spacer, a second spacer, can be positioned above and/or surrounding the pump. In some embodiments, the second spacer can be smaller than the first spacer used above the wound contact layer. A section of top film or cover layer (or a second cover layer) is positioned over the top of the second spacer with a second filter associated with or positioned within the second cover layer. In some embodiments, the first and second cover layer can be made of the same material. In some embodiments, the first and second cover layers can be made of different material.

A second filter can be alternative or additionally used. For example, filter 220 can be constructed from antibacterial and/or antimicrobial materials so that the pump can exhaust gases into the atmosphere. Filter 220 can also help to reduce noise produced by the pump.

In certain embodiments, the first and second cover layers include a moisture vapor permeable material that protects the pump and electronic components from liquid exudate removed from the wound and other liquids, while allowing gases through. The pump and electronics can be pouched between the fluid impermeable membranes or cover layers with the only input and output being a filter on each side of the pump. The membranes and filter can protect the electronics from liquid from both sides. In some embodiments, the dressing and integrated electronics pouch can be used in the shower and/or can be in contact with liquid without impeding the operation of the pump and dressing.

In some embodiments, in addition to or instead of one or more batteries, one or more alternative energy generators (such as RF energy harvester, thermal energy harvester, and the like) can be included into the pump to provide an alternative to traditional power sources. Examples of energy harvesters are described in U.S. Provisional Application No. 62/097,272, filed on Dec. 29, 2014 and U.S. Provisional Application No. 62/172,704, filed on Jun. 8, 2015, and titled "Negative Pressure Wound Therapy Apparatus and Methods for Operating the Apparatus," the disclosures of which are incorporated by reference in their entireties.

Figure 3:
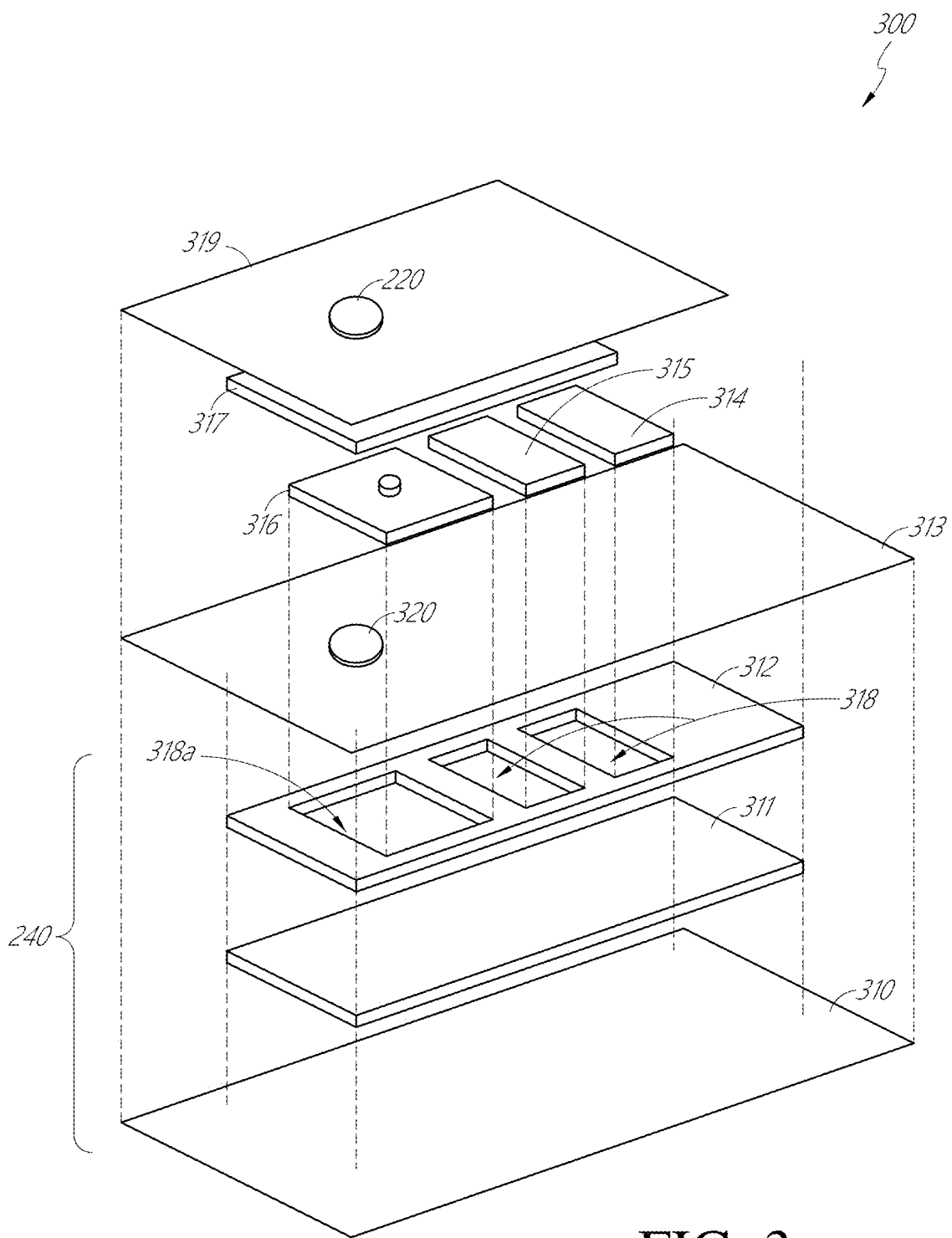
FIG. 3 illustrates an embodiment of layers of a wound dressing with integrated pump and electronic components.

FIG. 3 illustrates the layers of a wound dressing 300 with integrated pump and electronic components, such as a controller configured to control the pump, according to some embodiments. The dressing layer 240 includes a wound contact layer 310, a spacer layer 311, and an absorbent layer 312. In some embodiments, the spacer layer 311 can be formed at least partially from a three dimensional (3D) fabric. In certain embodiments, a superabsorbent material can be used in the absorbent layer 312. The absorbent layer 312 can include one or more recesses 318 (and 318a) within the layer to accommodate placement of the pump, electronics, and/or power source. A moisture vapor permeable top film or first cover layer 313 is positioned above the absorbent layer 312. The cover layer 313 can include a filter 320. The filter can be positioned in line with and above a recess 318a in the absorbent layer 212.

A pump 316, electronics package 315, and power source 314 (such as a battery) can be positioned above the cover layer 313 as shown in FIG. 3. The pump 316, electronics package 315, and power source 314 can be positioned on top of the cover layer 313 and at least partially depressed into the corresponding recesses 318 (and 318a) in the absorbent layer 312. For example, the pump 316 can be at least partially depressed in the recess 318a. A packing layer 317 can be positioned above and/or surrounding the pump 316, electronics package 315, and power source 314. The packing layer 317 can be formed from spacer material and/or absorbent material. The packing layer 317 can include 3D spacer. In some embodiments, the packing layer 317 additionally or alternatively can include a superabsorbent material. A second moisture vapor permeable top film or second cover layer 319 can be positioned over and seal the packing layer 317, pump 316, electronics package 315, and power source 314. The second cover layer 319 can also include a second filter 220.

In some embodiments, the operation of the pump can vary depending on the environmental humidity level. It can be advantageous to provide mechanisms to drive moisture out of the dressing or otherwise limit or control the humidity of the dressing. In some embodiments, a chamber generated by the layers above the pump can be used to act as a pressurized sink for gases (such as gases exhausted by the pump), thereby increasing the relative humidity (or RH) and delta RH across the outer membrane, which in turn can increase the rate of evaporation.

Figure 4:
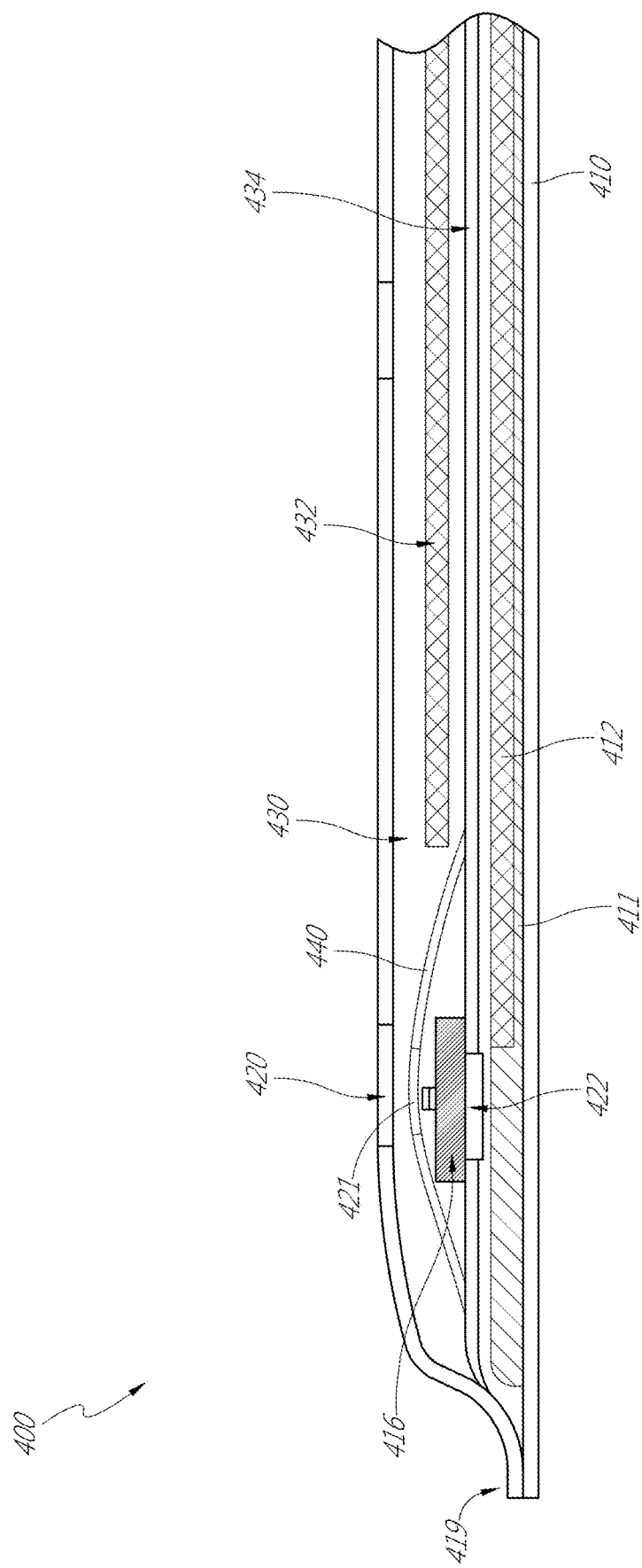
FIG. 4 illustrates an embodiment of a cross-section of an integrated wound dressing.

FIG. 4 illustrates a cross-section of an integrated wound dressing 400 showing the various layers according to some embodiments. The dressing 400 includes three filters 420, 421, 422. First filter 422 can be provided in the first wound contact layer below the pump and electronic components similar to the first filter 320 in the first cover layer 313 as described with reference to FIG. 3. The dressing 400 can include a second filter 421 positioned above a pump 416 as is shown in FIG. 4. In operation, the pump 416 inflates chamber 430 with gases removed from the wound. After inflation, chamber 430 can provide both bolstering and cushioning of the dressing 400. As shown in FIG. 4, an optional superabsorber 432 can be included in the chamber 430 above a moisture vapor permeable film or cover layer 434 and below the moisture vapor permeable top film or second cover layer 419. In such embodiments, the superabsorber 432 can draw fluid through the cover layer 434, and the increased pressure in chamber 430 can facilitate an increased evaporation to atmosphere. A third filter 420 can be positioned within or adjacent to the second moisture vapor permeable top film or second cover layer 419. Filter 420 can function similar to filter 220 illustrated in FIG. 2

In some embodiments, the pump can include a piezoelectric transducer that causes negative pressure to be supplied to the wound. In certain embodiments, a secondary device (such as a secondary piezoelectric device) can be used to generate atomisation of the fluid in the dressing, either accelerating evaporation of the water portion of the wound fluid or firing it through the moisture vapor permeable (MVP) top film where it can then evaporate. This can reduce or eliminate the effect of environmental humidity on the capability of the dressing to evaporate water.

Figure 5:
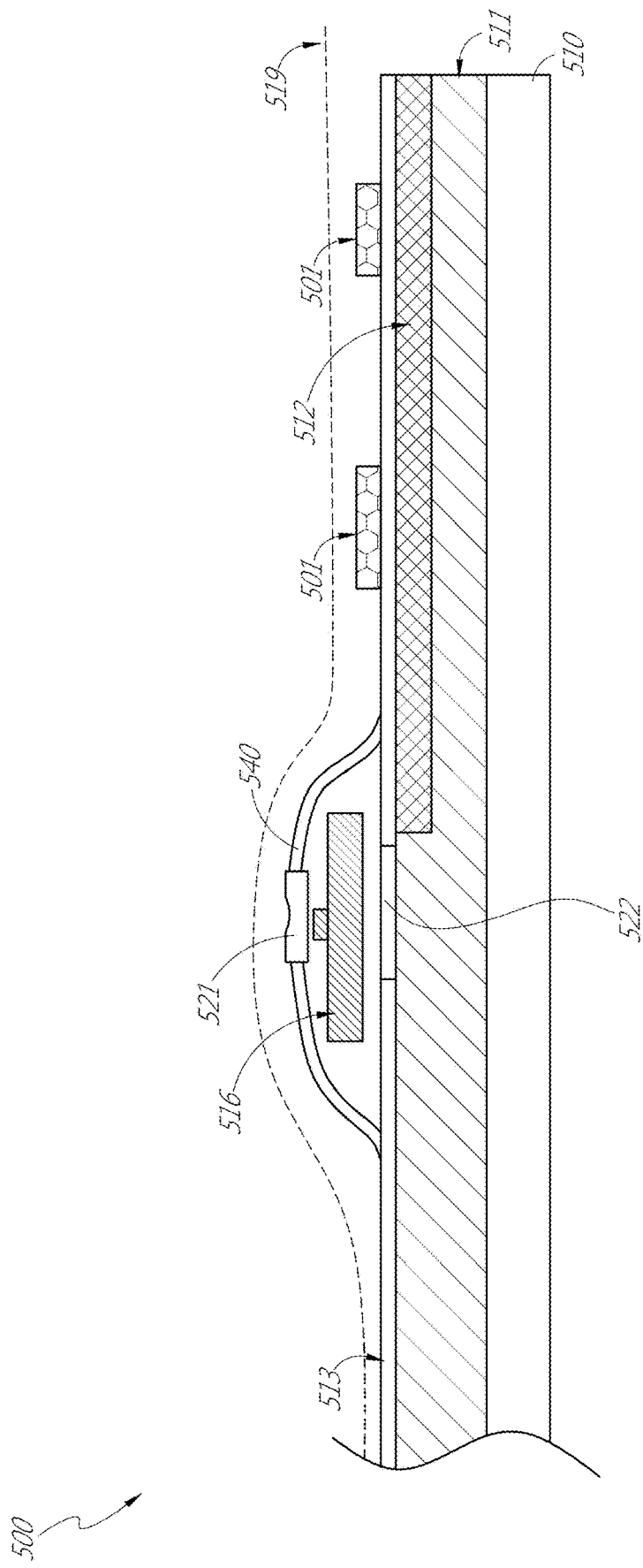
FIG. 5 illustrates an embodiment of a cross-section of an integrated wound dressing with ultrasonic oscillation.

FIG. 5 illustrates a cross-section of an integrated wound dressing 500 according to some embodiments. In the illustrated dressing 500, a top layer or second cover layer 519 is optional. In some embodiments, one or more ultrasonic oscillators 501 can be used to atomize water from the superabsorber and/or absorbent layer 512 or from between the top film or first cover layer 513 and the optional top film or second cover layer 519. In some embodiments, oscillation can be provided by a separate component such as a pump 516. In such embodiments, the one or more ultrasonic oscillators 501 would not be included in the dressing. The dressing 500 includes a wound contact layer 510 and a spacer layer 511.

In some embodiments, the electronics and/or associated components can be contained in single or multiple sealed pockets or pouches. The pockets or pouches can include the pump, electronics, and/or power source(s) (such as batteries) with or without a spacer layer padding. The packets may be designed to allow easy separation of the electronics from the dressing for disposal.

Figure 6A:
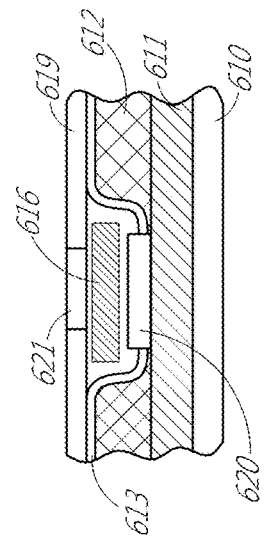
FIGS. 6A-6D illustrates embodiments of a pump pouch or pockets according to some embodiments.
Figure 6B:
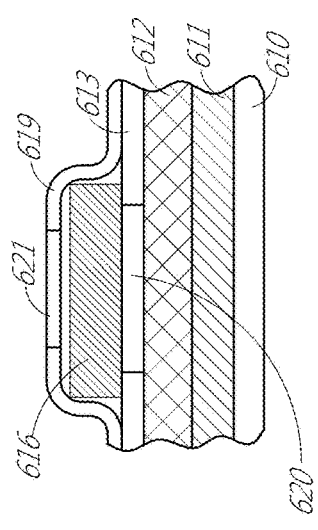

FIGS. 6A-6D illustrates embodiments of a pump pouch or pockets according to some embodiments. FIG. 6A illustrates an integrated wound dressing in which a pump 616 is placed on top of an absorbent layer. Electronics and power source(s) can be similarly placed. FIG. 6B illustrates an integrated wound dressing in which a pump 616 is positioned above the first cover layer 613 in a recess of the absorbent layer 612. This positioning is similar to that illustrated in FIG. 3. Electronics and power source(s) can be similarly placed.

Figure 6C:
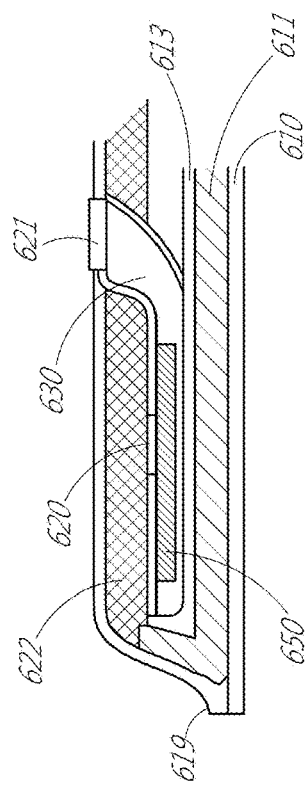
Figure 6D:
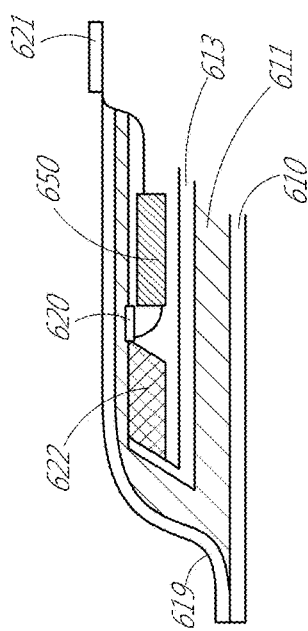

FIGS. 6C-6D illustrate embodiments of wound dressings comprising a pump and electronics package 650. The package 650 can also include power source(s). The pump and electronics package 650 can be positioned in the dressing as described with reference to FIG. 3. In other embodiments, the pump and electronics packages 650 can be positioned in alternative positions than what is described with reference to FIG. 3. For example, as depicted in FIG. 6C, the dressing can comprise a wound contact layer 610, a spacer layer 611, a moisture vapor permeable film or first cover layer 613 positioned above the contact layer 610 and spacer layer 611. The pump and electronics package 650 can be positioned above the first cover layer 613. Additionally, the absorbent layer 622 can be positioned above the first cover layer 613 and adjacent to the pump and electronics package 650. A second cover layer 619 can be positioned above the absorbent layer 622 and can seal at the perimeter of the second cover layer 619 to the wound contact layer 610 at the perimeter of the wound contact layer 610. Filter 620 can be located adjacent to the pump and electronics package 650. The filter 620 can be a hydrophobic filter configured to protect the pump and electronics package from exposure to fluid. Second filter 621 can be located on the second cover layer 619. The second filter can be located at a position adjacent to an outlet or exhaust of the pump system. Additionally or alternatively, the exhaust of the pump can be gaseously connected to the filter 621 positioned proximate to the exhaust. The gaseous connection can include one or more conduits and/or chambers.

FIG. 6D illustrates an embodiment of a wound dressing with pump and electronics package 650 positioned within the dressing. The dressing can include a wound contact layer 610 and spacer layer 611. A moisture vapor permeable film or first cover layer 613 can be positioned above the wound contact layer 610 and the spacer layer 611. The pump and electronics package 650 can be positioned above the first cover layer 613. An absorbent layer 622 can be provided above the pump or electronics package 650. A filter 620 can be provided between the pump and electronics package 650 and the absorbent layer 622 as shown in FIG. 6D. The filter 620 can protect the pump and electronics package 650 from exposure to fluid. An additional filter or second filter 621 can be provided on a second moisture vapor permeable film or second cover layer 619. The filter 621 can be located at a position adjacent to an outlet or exhaust of the pump system or proximate to the exhaust (and connected to the exhaust via one or more conduits and/or chambers). For example, as is illustrated, a chamber 630 can gaseously connect the pump exhaust and the filter 621. In some embodiments, the chamber 630 can function similar to the chamber 430 of FIG. 4. Additionally or alternatively, the chamber 630 can be configured as a silencer to mute noise produced by the pump. The second cover layer 619 can be positioned above the absorbent layer 622 and can seal at the perimeter of the second cover layer 619 to the wound contact layer 610 at the perimeter of the wound contact layer 610.

In some embodiments, a circumference port can be used to bring fluid to the uppermost spacer layer first before being drawn down into the superabsorbent layer and pump. In some embodiments, a full circumference port or multiple circumferential ports can be used. The circumference ports can be used at the perimeter of the wound dressing. This can make the fluid behaviour independent of the direction the dressing is applied in. Without this feature, the capacity can be lower if the port is positioned at the bottom portion of the applied dressing.

In some embodiments, the whole pump pouch can be generated as a specific layer that can be brought into the factory as a reel and/or folded raw material, allowing the manufacture of a full system using the machinery used to manufacture the layers of a wound dressing. The pump and other components can be placed into their respective compartments in the dressing.

In some embodiments, one or more of the following pump additions can be added to the wound dressing with an integrated pump. The pressure sensor can be added onto a substrate of the pump (for example, ceramic substrate). A pressure fuse can be utilized on the pump substrate to discontinue operation of the pump if the pressure generated exceeds an acceptable threshold. Additionally, the pump can be designed for specific pressures. The pump can be designed to disable provision of negative pressure if fluid enters the pump itself.

Figure 7:
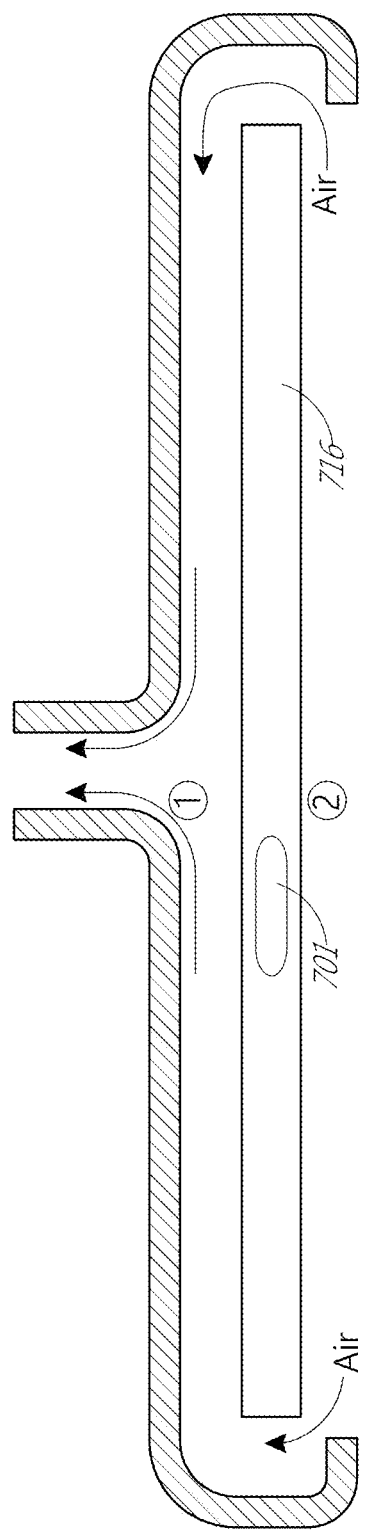
FIG. 7 illustrates an embodiment of a pressure fuse that can be used to discontinue operation of the pump if the pressure exceeds an acceptable (or safe) threshold pressure.

FIG. 7 illustrates a pressure fuse that can be used to discontinue operation of the pump if the pressure exceeds an acceptable (or safe) threshold pressure according to some embodiments. As illustrated in FIG. 7, a void or bubble 701 (labeled as "3") is provided within or adjacent to a piezo element 716 (labeled as "4") of a pump. The void or bubble 701 includes gas, such as gas stored at a pressure exceeding the operating pressure of the pump. For example, if the pressure at region 2 in FIG. 7 exceeds a pressure threshold (e.g., falls below −200 mmHg or another suitable threshold value), then the void or bubble 701 bursts and thereby stops operation of the pump. For example, if the bubble 701 ruptures, the piezo element will become inoperative and the pump will no longer work. In other embodiments, the wiring to the piezo element or pump can run across the surface of the bubble (and/or inside the bubble). In such embodiment, bursting of the bubble could sever the wire and thereby stop or discontinue operation of the pump. The illustrated and described embodiments are not limited to pumps operated by piezoelectric transducers. For example, a void or bubble can be used to deactivate or render inoperative voice coil pumps, diaphragm pumps, etc.

Further elements can be incorporated into the device to increase the usability of this device. For example, one or more of speaker(s) and/or vibration indicator(s) can be included. The pump can be operated via a controller. One or more user interface elements for operating the pump can be included.

Figure 8:
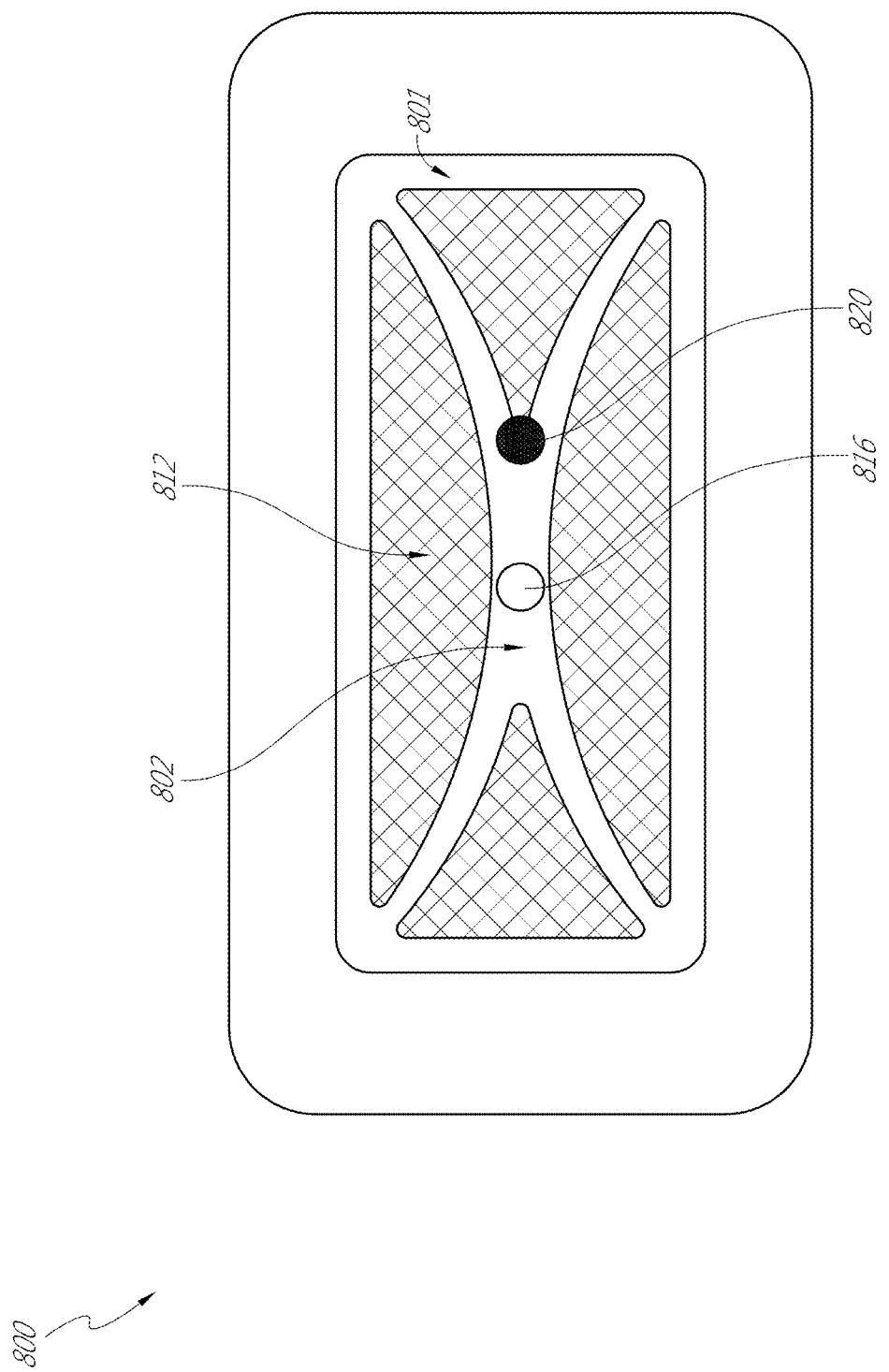
FIG. 8 illustrates an embodiment of an integrated wound dressing with the pump and electronics package incorporated within the dressing.

FIG. 8 illustrates an integrated wound dressing 800 with the pump and electronics package incorporated within the dressing according to some embodiments. The dressing is similar to that described with reference to FIGS. 3-7, except that the dressing 800 includes a different spacer layer and absorbent layer arrangement. The spacer layer comprises a channel 801 that forms a ring about the wound dressing. The absorbent layer 812 is surrounded by the spacer channel 801. There are additional channels 802 formed in the absorbent layer. The channels 801 and 802 form chambers that can facilitate evaporation of fluid as is explained above in connection with FIG. 4.

Figure 9B:
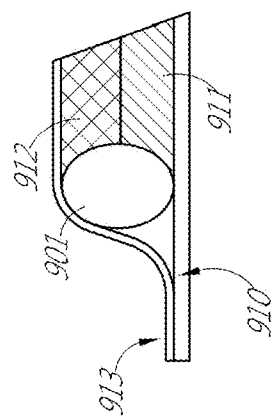
FIGS. 9A-9B illustrate another embodiment of an integrated wound dressing.
Figure 9A:
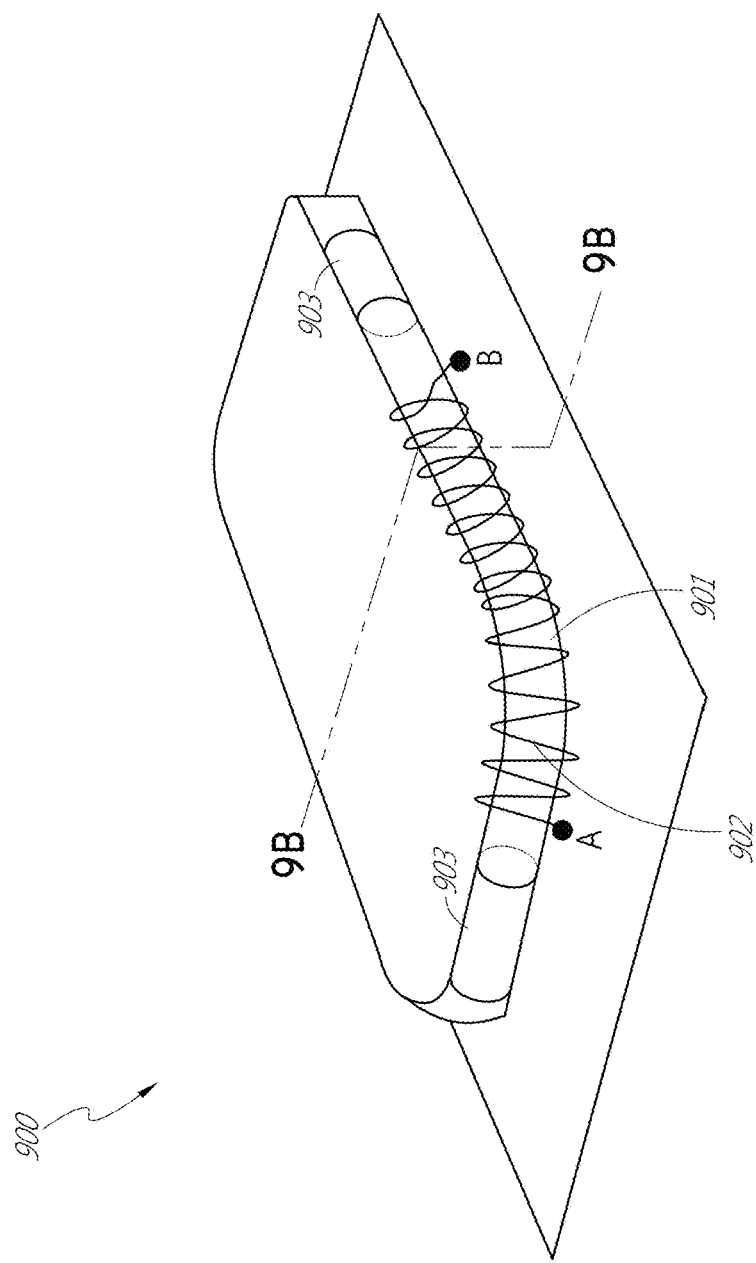

FIGS. 9A-9B illustrate integrated wound dressing 900 according to some embodiments. As illustrated in FIG. 9A, the integrated wound dressing 900 comprises a tube 901 filled with magnetic fluid (or a solid magnet 901). As illustrated in FIG. 9B, the tube 901 can be positioned on the perimeter of the spacer layer 911 and/or absorbent layer 912, and the tube 901 can run along or across the dressing 900. FIG. 9A also illustrates a coil of wire 902 excited by sinusoidal or other potential difference between points A and B. That is, the pump is actuated by electromagnetic field (for example, the pump can be a voice coil pump). The dressing further comprises one or more pump chambers 903 positioned on the dressing as illustrated in FIG. 9A. Each of the pump chambers 903 can include one or more one-way valves. In some embodiments, the pump chambers can have an additional membrane or piston positioned between the magnetic field and chamber.

As shown in FIG. 9B, the wound dressing can include a wound contact layer 910 and a moisture vapor permeable top film or cover layer 913. The perimeter of the cover layer 913 can seal to the perimeter of the wound contact layer enclosing the components of the wound dressing apparatus.

Figure 10:
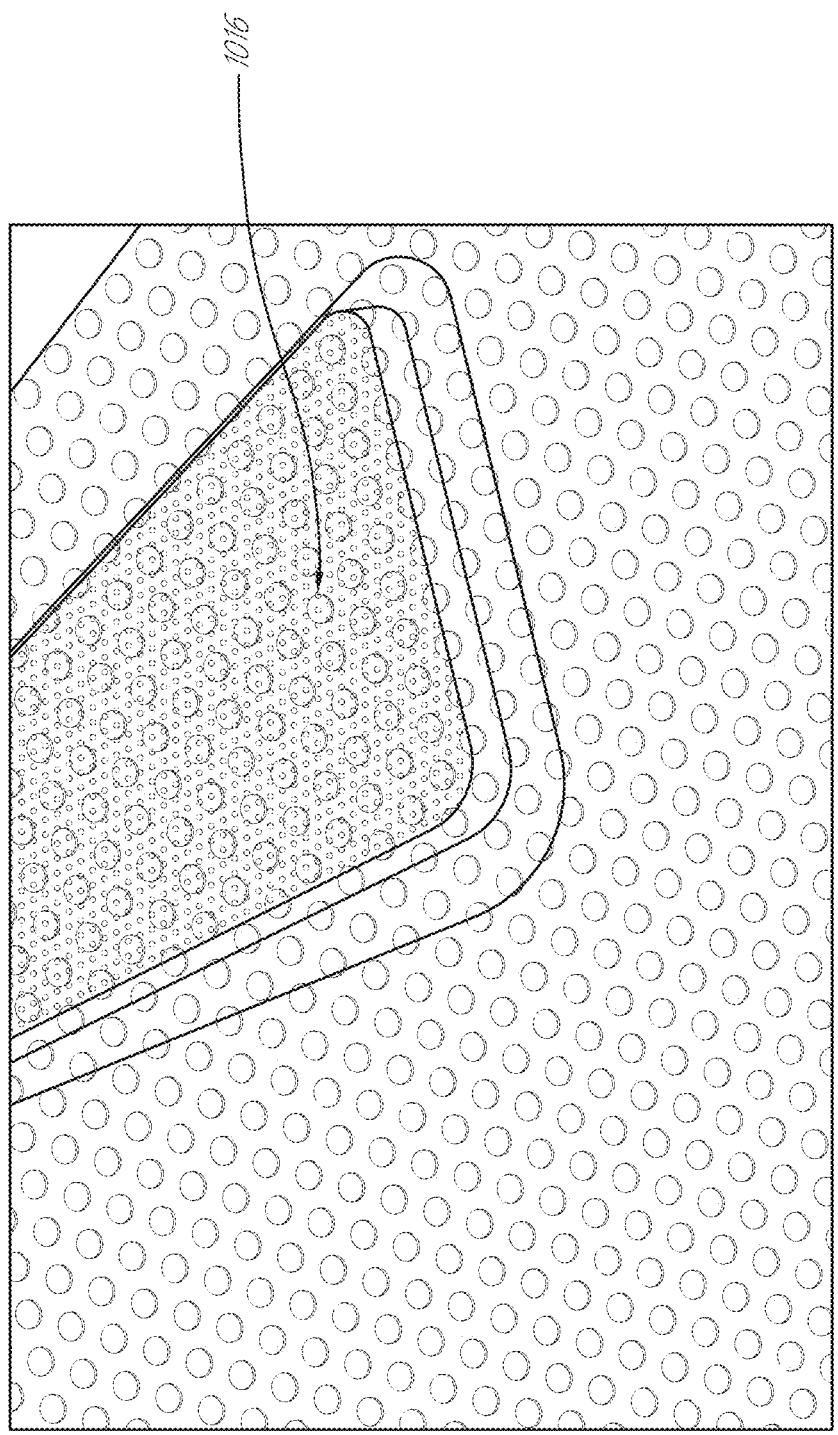
FIG. 10 illustrates a close up view of one end of an embodiment of an integrated wound dressing.

FIGS. 10-12 show embodiments of integrated dressings. FIG. 10 illustrates a close up view of one end of the wound dressing. The pump 1016 is visible as a dark spot under the top layer.

Figure 11A:
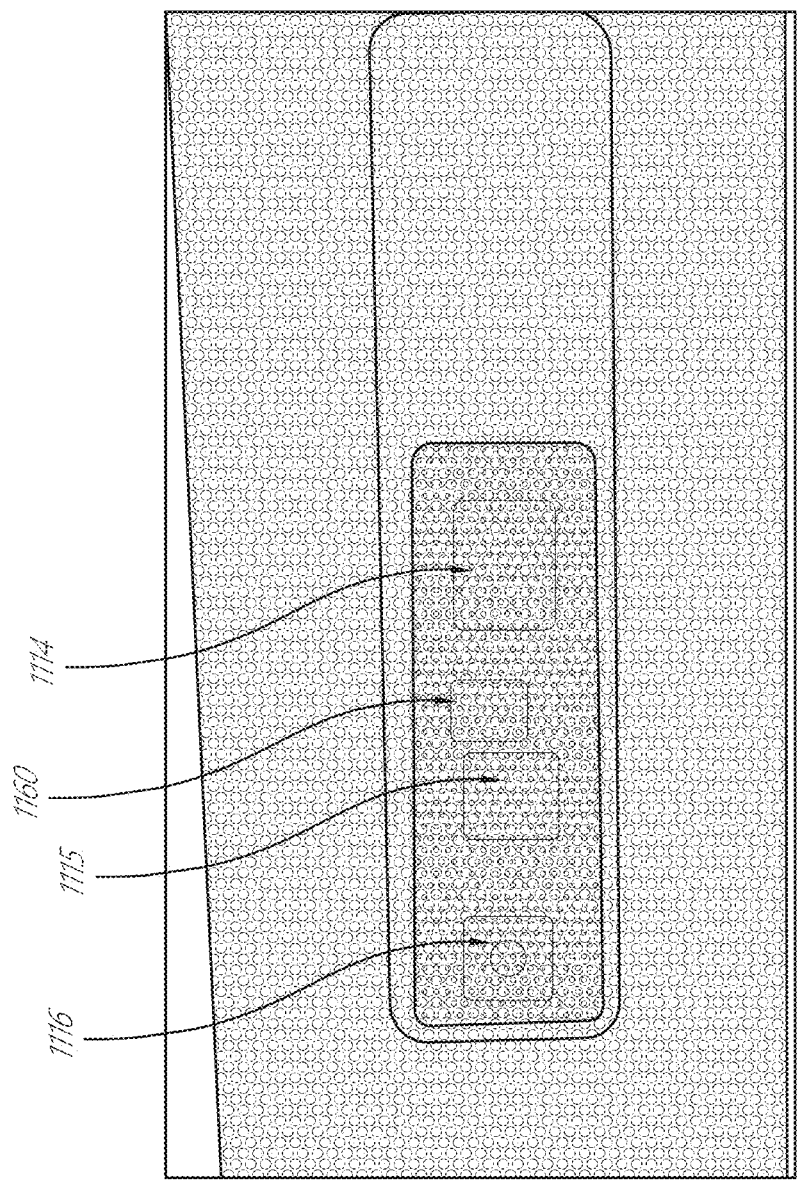
FIG. 11A shows a top view of an embodiment of a wound dressing where the pump and associated components are visible.

FIG. 11A shows a top view of a wound dressing where the pump and associated components are visible. The pump 1116, electronics package 1115, switch 1160 for operating the pump (e.g., turning the pump on/off), and power source 1114 are visible from the top of the dressing.

Figure 11B:
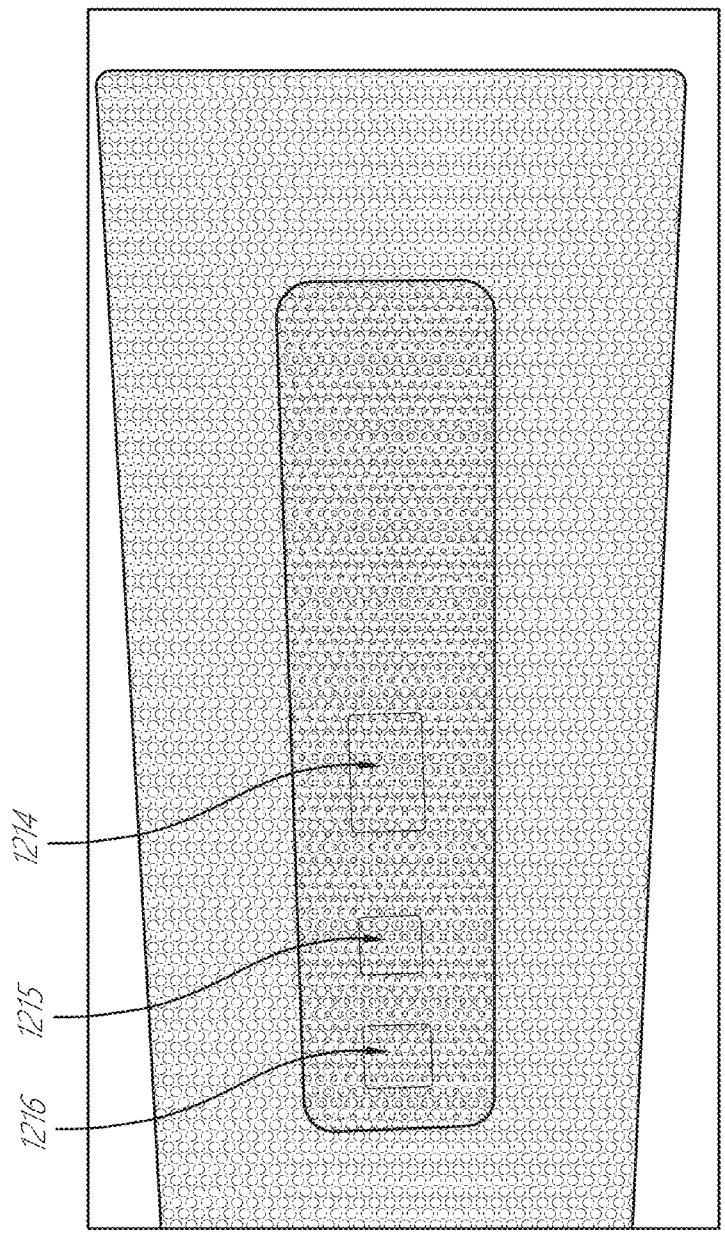
FIG. 11B shows a bottom view of an embodiment of a wound dressing where recesses for the pump and associated components are visible.

FIG. 11B shows a bottom view of a wound dressing where recesses for the pump and associated components are visible. Recess 1216 can be a pump recess, recess 1215 can be an electronics package recess, and recess 1214 can be a power source recess.

In some embodiments, the pump and/or other electronic components can be configured to be positioned adjacent to or next to the absorbent and/or transmission layers so that the pump and/or other electronic components are still part of a single apparatus to be applied to a patient, but the pump and/or other electronics are positioned away from the wound site.

Figure 12A:
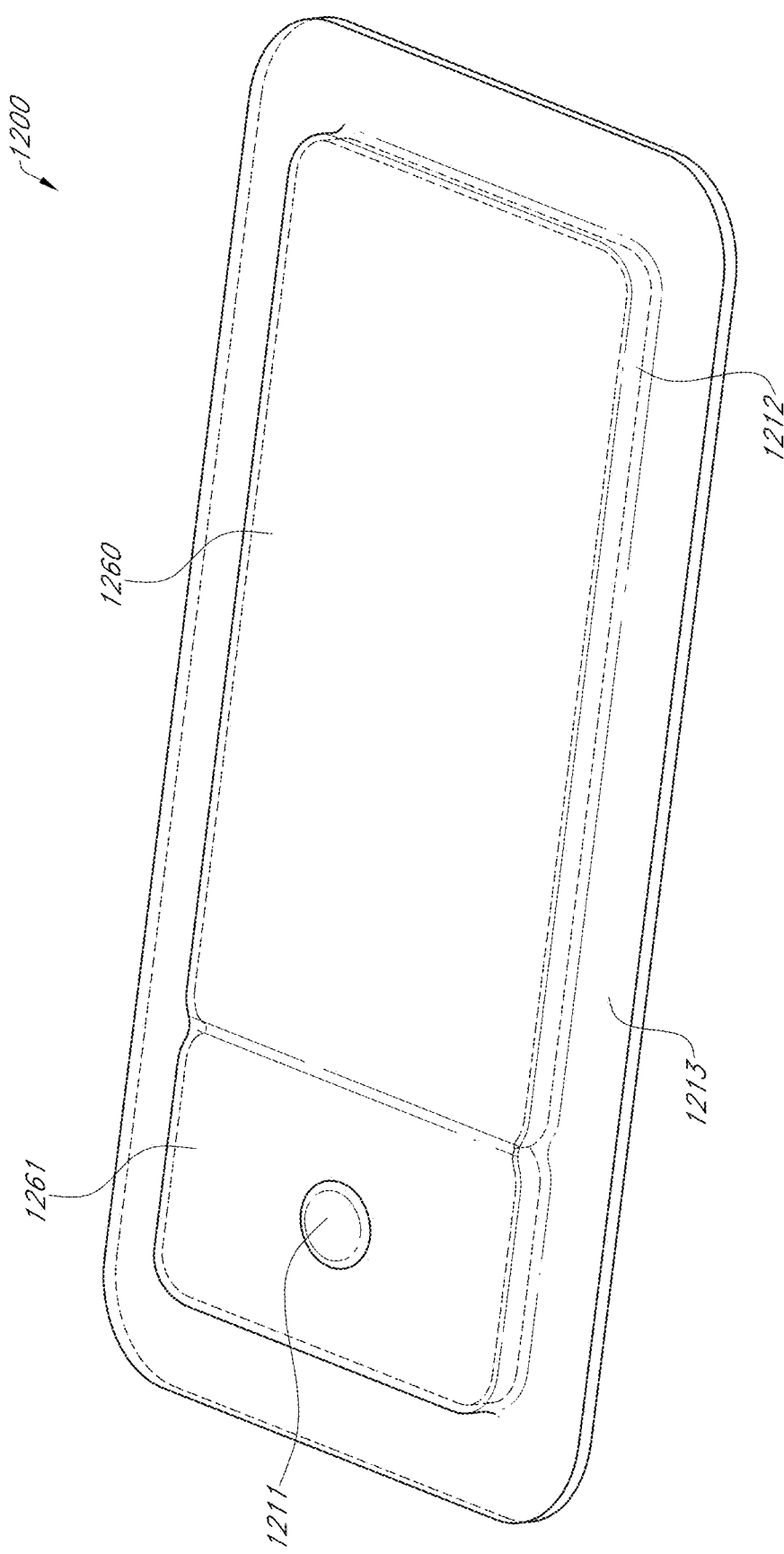
FIGS. 12A-12B illustrate an embodiment of a wound dressing incorporating the source of negative pressure and/or other electronic components within the wound dressing.
Figure 12B:
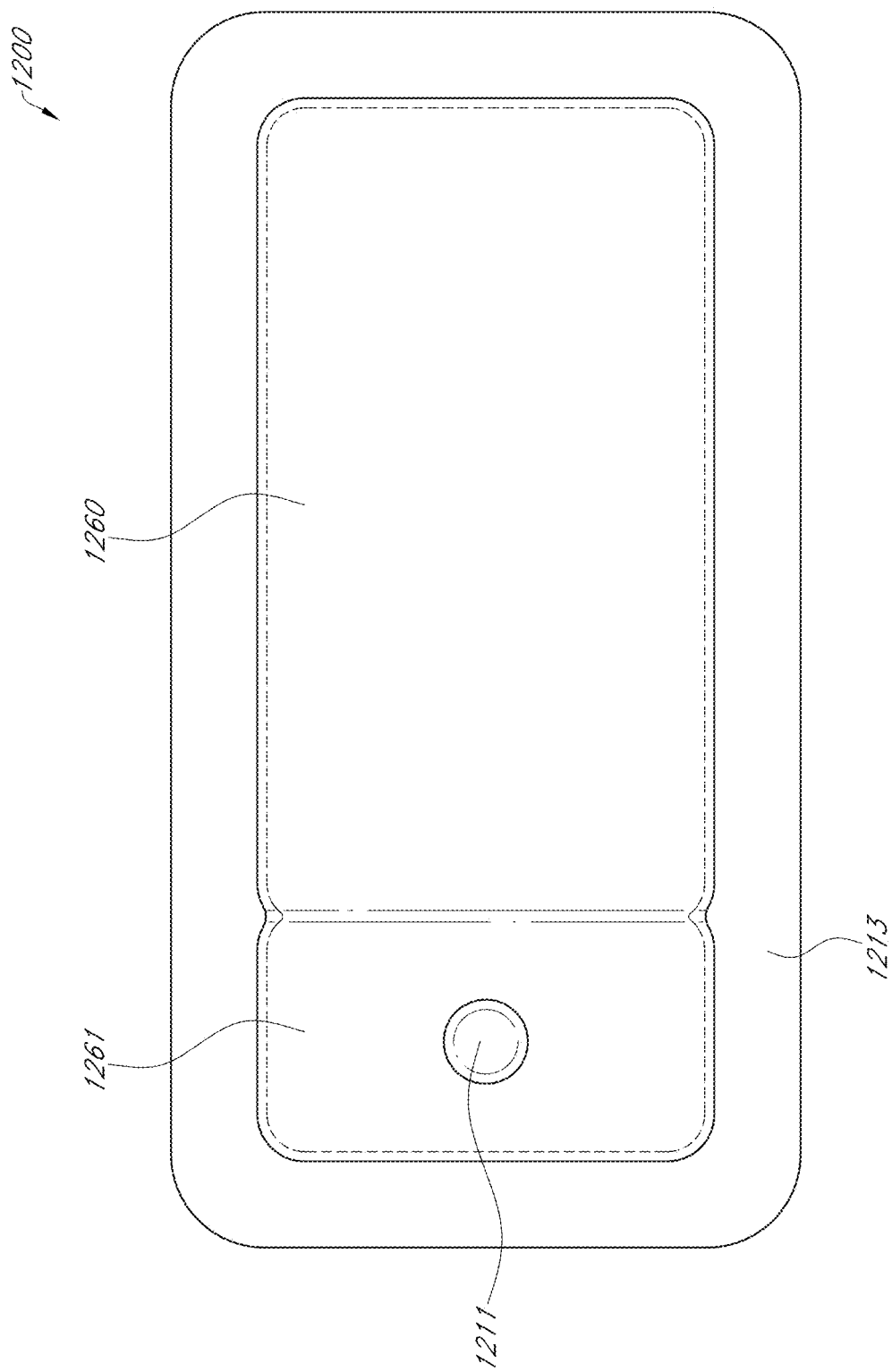

In some embodiments, the pump and/or other electronic components can be configured to be positioned adjacent to or next to the absorbent and/or transmission layers so that the pump and/or other electronic components are still part of a single apparatus to be applied to a patient with the pump and/or other electronics positioned away from the wound site. FIGS. 12A-12B illustrates a wound dressing incorporating the source of negative pressure and/or other electronic components within the wound dressing. FIGS. 12A-12B illustrates a wound dressing 1200 with the pump and/or other electronics positioned away from the wound site. The wound dressing can include an electronics area 1261 and an absorbent area 1260. The dressing can comprise a wound contact layer (not shown) and a moisture vapor permeable film or cover layer 1213 positioned above the contact layer and other layers of the dressing. The wound dressing layers and components of the electronics area as well as the absorbent area can be covered by one continuous cover layer 1213 as shown in FIGS. 12A-12B.

The electronics area 1261 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 1261 can include a button or switch 1211 as shown in FIG. 12A-12B. The button or switch 1211 can be used for operating the pump (e.g., turning the pump on/off).

The absorbent area 1260 can include an absorbent material 1212 and can be positioned over the wound site. The electronics area 1261 can be positioned away from the wound site, such as by being located off to the side from the absorbent area 1260. The electronics area 1261 can be positioned adjacent to and in fluid communication with the absorbent area 1260 as shown in FIGS. 12A-12B. In some embodiments, each of the electronics area 1261 and absorbent area 1260 may be rectangular in shape and positioned adjacent to one another.

In some embodiments, additional layers of dressing material can be included in the electronics area 1261, the absorbent area 1260, or both areas. In some embodiments, the dressing can comprise one or more spacer layers and/or one or more absorbent layer positioned above the contact layer and below the wound cover layer 1213 of the dressing.

The dressing can comprise a wound contact layer (not shown), a spacer layer (not shown), an absorbent layer 1212, a moisture vapor permeable film or cover layer 1213 positioned above the wound contact layer, spacer layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound. The first spacer layer assists in distributing negative pressure over the wound site and facilitating transport of wound exudate and fluids into the wound dressing. In some embodiments, the spacer layer can be formed at least partially from a three dimensional (3D) fabric. Further, an absorbent layer (such as layer 1212) for absorbing and retaining exudate aspirated from the wound can be utilized. In some embodiments, a superabsorbent material can be used in the absorbent layer 1212. In some embodiments, the absorbent includes a shaped form of a superabsorber layer. The wound dressing layers of the electronics area and the absorbent layer can be covered by one continuous cover layer 1213. In some embodiments, the cover layer can include a moisture vapor permeable material that prevents liquid exudate removed from the wound and other liquids from passing through, while allowing gases through.

Figure 13A:
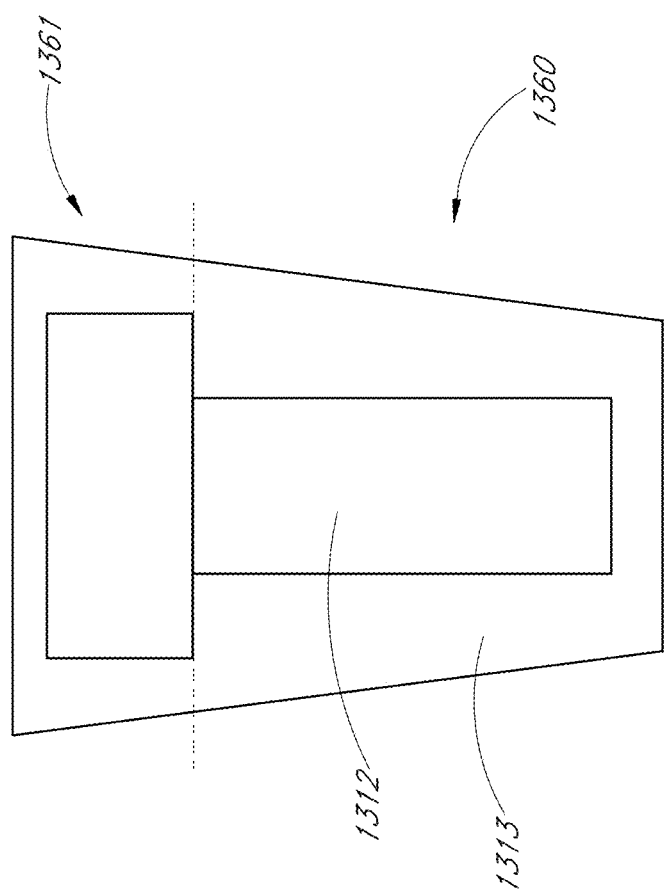
FIG. 13A illustrates an embodiment of a wound dressing with the pump and/or other electronics positioned away from the wound site.

FIG. 13A illustrates a wound dressing with the pump and/or other electronics positioned away from the wound site. The wound dressing can include an electronics area 1361 and an absorbent area 1360. The absorbent area 1360 can include an absorbent material 1312 and can be positioned over the wound site. The electronics area 1361 can be positioned away from the wound site, such as by being located off to the side from the absorbent area 1360. The electronics area 1361 can be positioned adjacent to and in fluid communication with the absorbent area 1360. In some embodiments, each of the electronics area 1361 and absorbent area 1360 may be rectangular in shape, and positioned adjacent to one another to form a T-shape. In such an embodiment, each of the areas 1360 and 1361 are elongated with longitudinal axes that are perpendicular or substantially perpendicular to one another. As shown in FIG. 13A, the top portion of the T can be where the electronics would be located, and the bottom of the T can be placed on the wound.

Figure 13B:
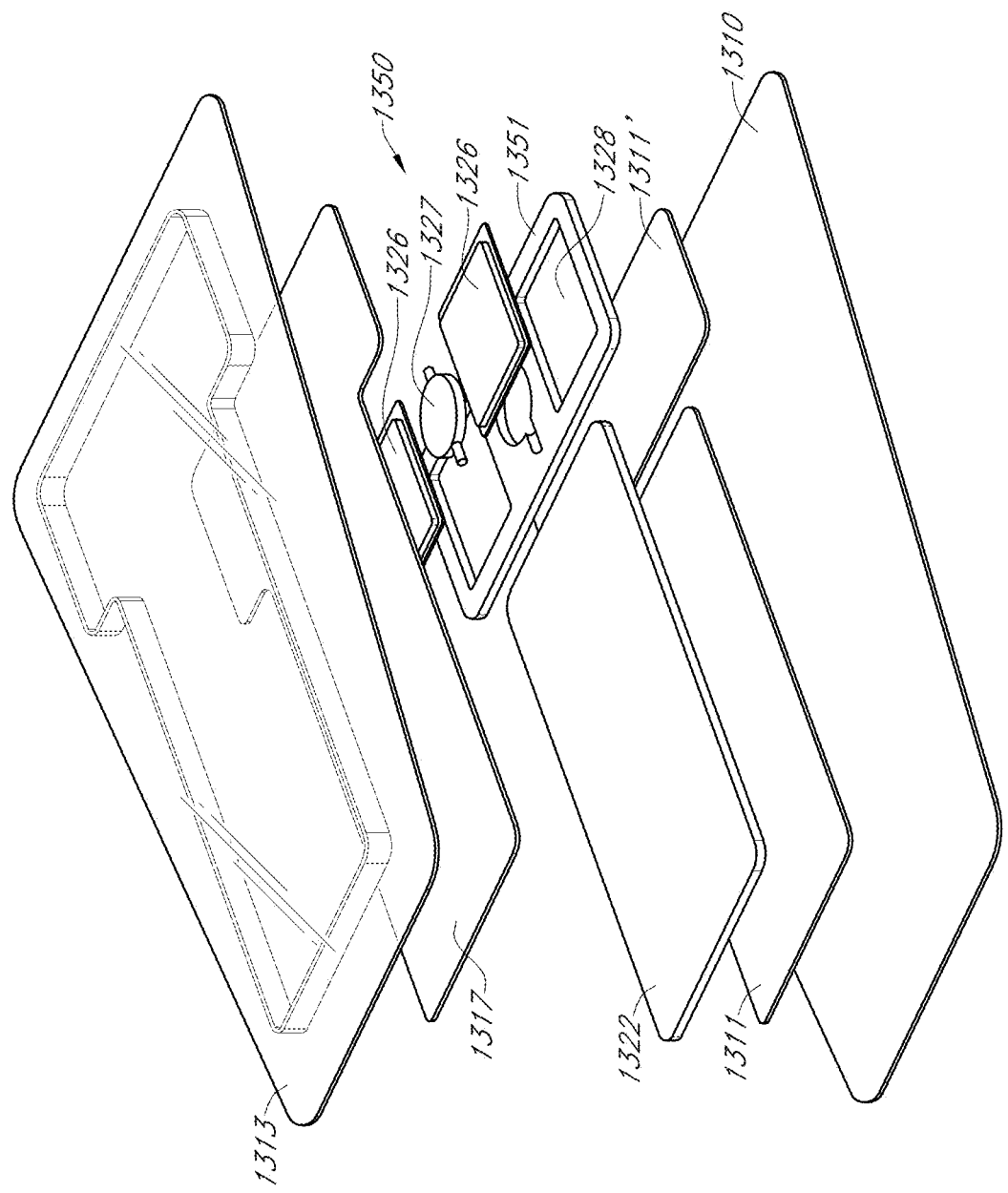
FIG. 13B illustrates an embodiment of layers of a wound dressing with the pump and electronic components offset from the absorbent area of the dressing.

FIG. 13B illustrates an embodiment of layers of a wound dressing with the pump and electronic components offset from the absorbent area of the dressing. As illustrated in FIG. 13B, the dressing can include a wound contact layer 1310 for placing in contact with the wound. Lower spacer layers 1311 and 1311' are provided above the wound contact layer 1310. In some embodiments, the spacer layer 1311 can be a separate layer from spacer layer 1311' as shown in FIG. 13B. The lower spacer layers 1311 and/or 1311' can assist in distributing pressure evenly to the wound surface and/or wicking fluid away from the wound. An absorbent layer 1322 can be positioned above the lower spacer layer 1311. A dressing layer 1351 can include cutouts or recesses 1328 for embedding the electronic components 1350 within the layer 1351. In some embodiments, the cutouts or recesses 1328 can be sized and shaped to embed a pump 1327, power source 1326, and/or other electronic components. In some embodiments, the layer 1351 can include multiple spacer layers stacked together. In some embodiments, the layer 1351 can include multiple spacer layers pieced together to surround the electronic components 1350. An upper spacer layer can be provided above the absorbent layer 1322, layer 1351, and/or electronic components 1350. A cover layer or backing layer 1313 can be positioned over the upper spacer layer. The backing layer 1313 can form a seal to the wound contact layer 1310 at a perimeter region enclosing the spacer layers 1311, 1311', and 1317, the absorbent layer 1322, layer 1351, and electronic components 1350. In some embodiments, the backing layer 1313 can be a flexible sheet of material that forms and molds around the dressing components when they are applied to the wound. In other embodiments, the backing layer 1313 can be a material that is preformed or premolded to fit around the dressing components as shown in FIG. 13B.

Figure 14:
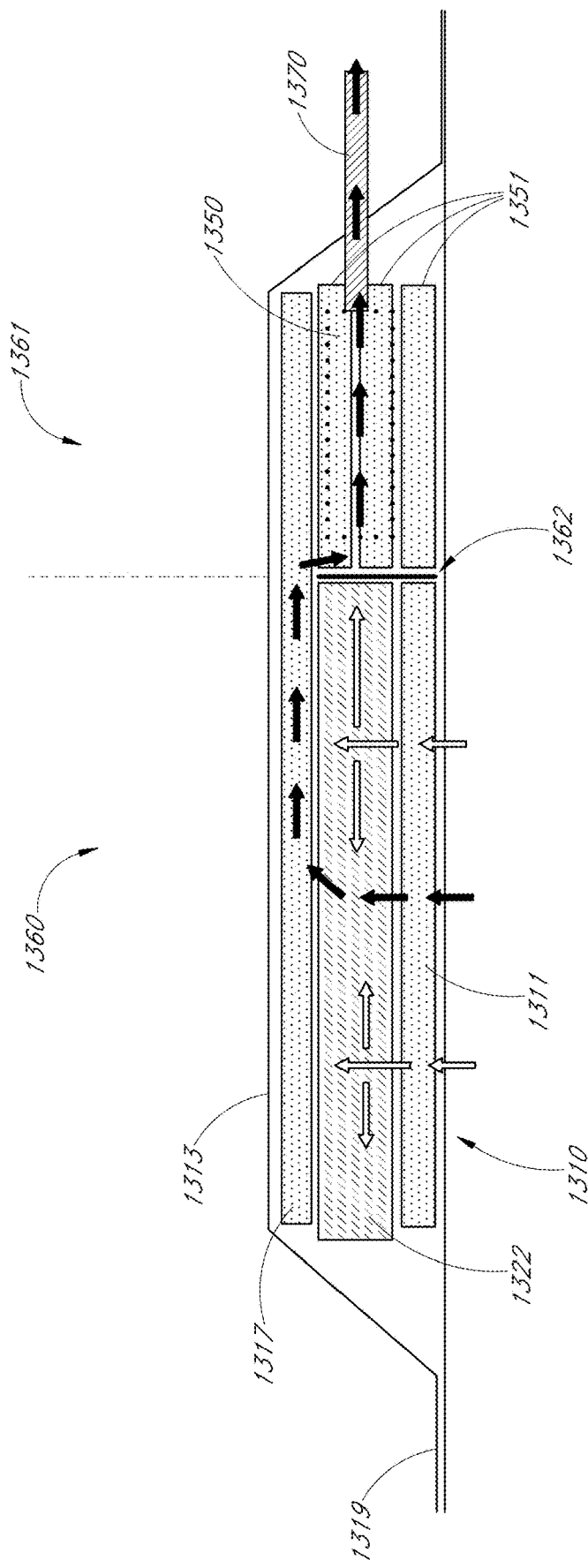
FIG. 14 illustrates a side cross-sectional view of an embodiment of a wound dressing with the pump and electronic components offset from the absorbent area of the dressing positioned over the wound.

FIG. 14 illustrates an embodiment of a wound dressing with the pump and electronic components offset from the absorbent area of the dressing positioned over the wound. The wound dressing can comprise a wound contact layer 1310 and a moisture vapor permeable film or cover layer 1313 that enclose an absorbent area 1360 and an electronics area 1361. The cover layer 1313 can seal at the perimeter of the cover layer 1319 to the wound contact layer 1310 at the perimeter of the wound contact layer. The dressing can comprise an upper spacer layer or first spacer layer 1317 that includes a continuous layer of spacer material positioned below the cover layer 1313 and above the layers of the absorbent area and the layers of the electronics area. The continuous layer of spacer material or upper spacer layer 1317 can enable an air pathway between the two areas of the dressing as illustrated by black directional arrows in FIG. 14.

The absorbent area 1360 of the dressing can comprise a second spacer layer 1311 or lower spacer layer and an absorbent layer 1322 positioned above the wound contact layer 1310. The second spacer layer 1311 can allow for an open air path over the wound site. The absorbent layer 1322 can comprise a super absorber positioned in the absorbent area 1360 of the dressing. The absorbent layer 1322 can retain wound fluid within thereby preventing fluid passage of wound exudates into the electronics area 1361 of the dressing. The wound fluids can flow through the wound contact layer 1310, to the lower spacer layer 1311, and into the absorbent layer 1322. The wound fluids are then spread throughout the absorbent layer 1322 and retained in the absorbent layer 1322 as shown by the white directional arrows for wound fluids in FIG. 14.

The electronics area 1361 of the dressing can comprise a plurality of layers of spacer material 1351. In some embodiments, the electronic components 1350 embedded within the plurality of layers of spacer material 1351. The layers of spacer material can have recesses or cut outs to embed the electronic components within whilst providing structure to prevent collapse. The electronic components 1350 can include a pump, power source, controller, and/or an electronics package, although any suitable electronics component is appreciated. In some embodiments, a bather and/or partition can be provided between the absorbent area 1360 and the dressing layers surrounding the electronic components in the electronics area 1361. A partition 1362 can optionally be positioned between the absorbent area 1360 and the electronics area 1361. The partition 1362 can separate the absorbent layer 1322 and lower air flow spacer layer 1311 from the electronic housing segment of the dressing in the electronic area. The partition 1362 can prevent wound fluid (e.g., wound exudate) from entering the electronic housing section of the dressing. In some embodiments, the partition can be a non-porous dam or other structure. The non-porous dam 1362 can comprise a cyanoacrylate adhesive bead or a strip of silicone. The air pathway through the dressing is shown in FIG. 14 by directional arrows. The air flows through the wound contact layer 1310, the lower spacer layer 1311, and the absorbent layer 1322 and into the first spacer layer 1317. The air can travel horizontally through the first spacer layer 1317 over and around the partition 1362 into the electronics area of the dressing as illustrated by the black directional arrows in FIG. 14.

A pump exhaust 1370 can be provided to exhaust air from the pump to the outside of the dressing. The pump exhaust can be in communication with the electronics area 1361 and the outside of the dressing. In some embodiments, the pump exhaust 1370 can be a flexible fluidic connector that comprises a 3D material that allows for pressure to be applied without collapse of the exhaust port as described in more detail herein. Examples of an application where additional disclosure relating to the 3D material can be found include US Publication No. 2015/0141941, titled "Apparatuses and Methods for Negative Pressure Wound Therapy" published on May 21, 2015. The disclosure of this patent is hereby incorporated by reference in its entirety.

Figure 15:
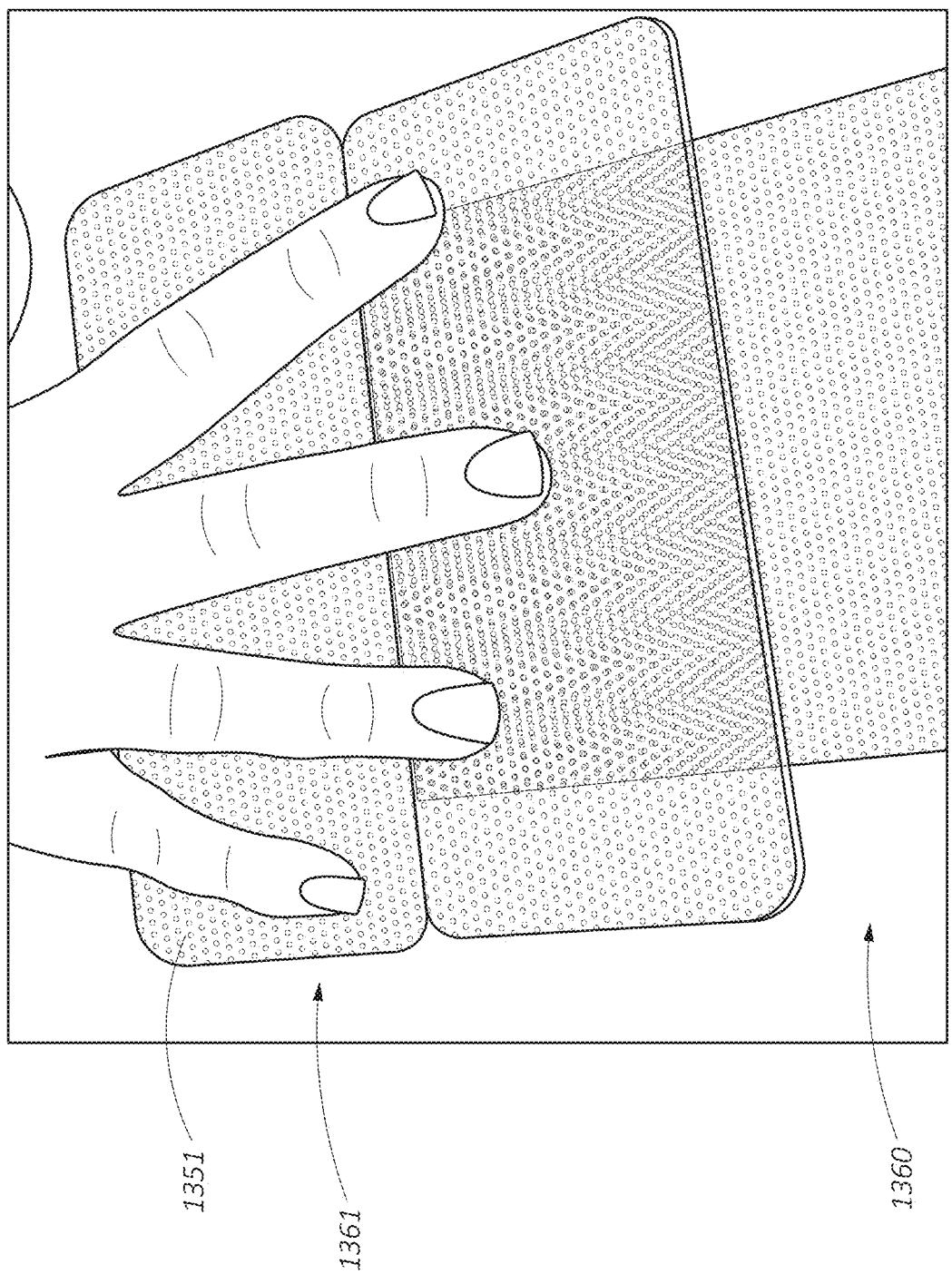
FIGS. 15-27 show embodiments of the wound dressing with the electronic components offset from the absorbent material of the dressing.

FIGS. 15-27 show embodiments of the wound dressing with the electronic components 1350 offset from the absorbent material 1322 of the dressing. FIGS. 15-27 show the wound dressing similar to the dressing described with reference to FIG. 14. In FIG. 15 the dressing is shown with the portion of the upper or first spacer layer 1317 over the electronic area 1361 folded back and exposing an underlying spacer layer of the plurality of spacer layers 1351 in the electronics area 1361.

Figure 16:
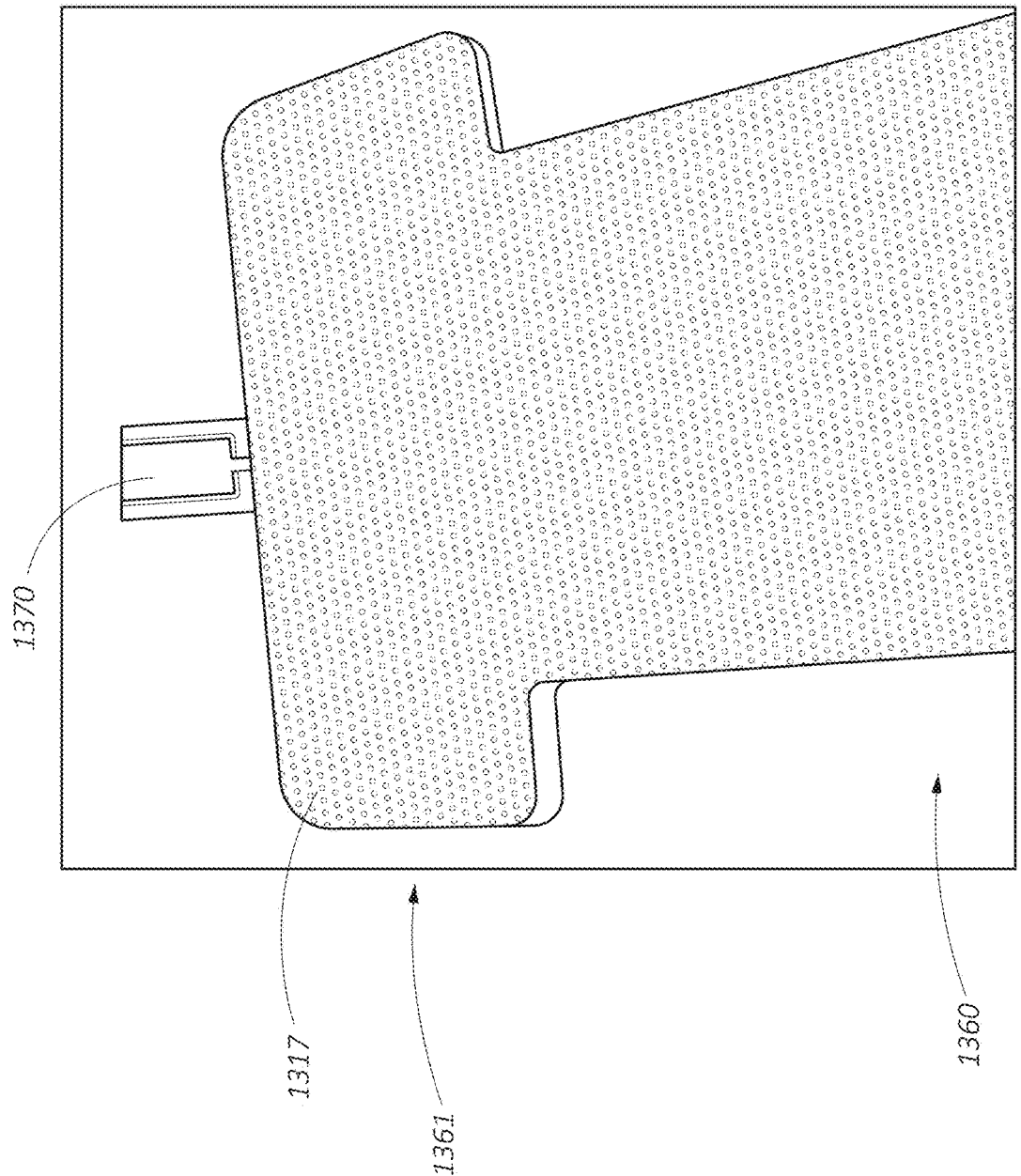
Figure 17:
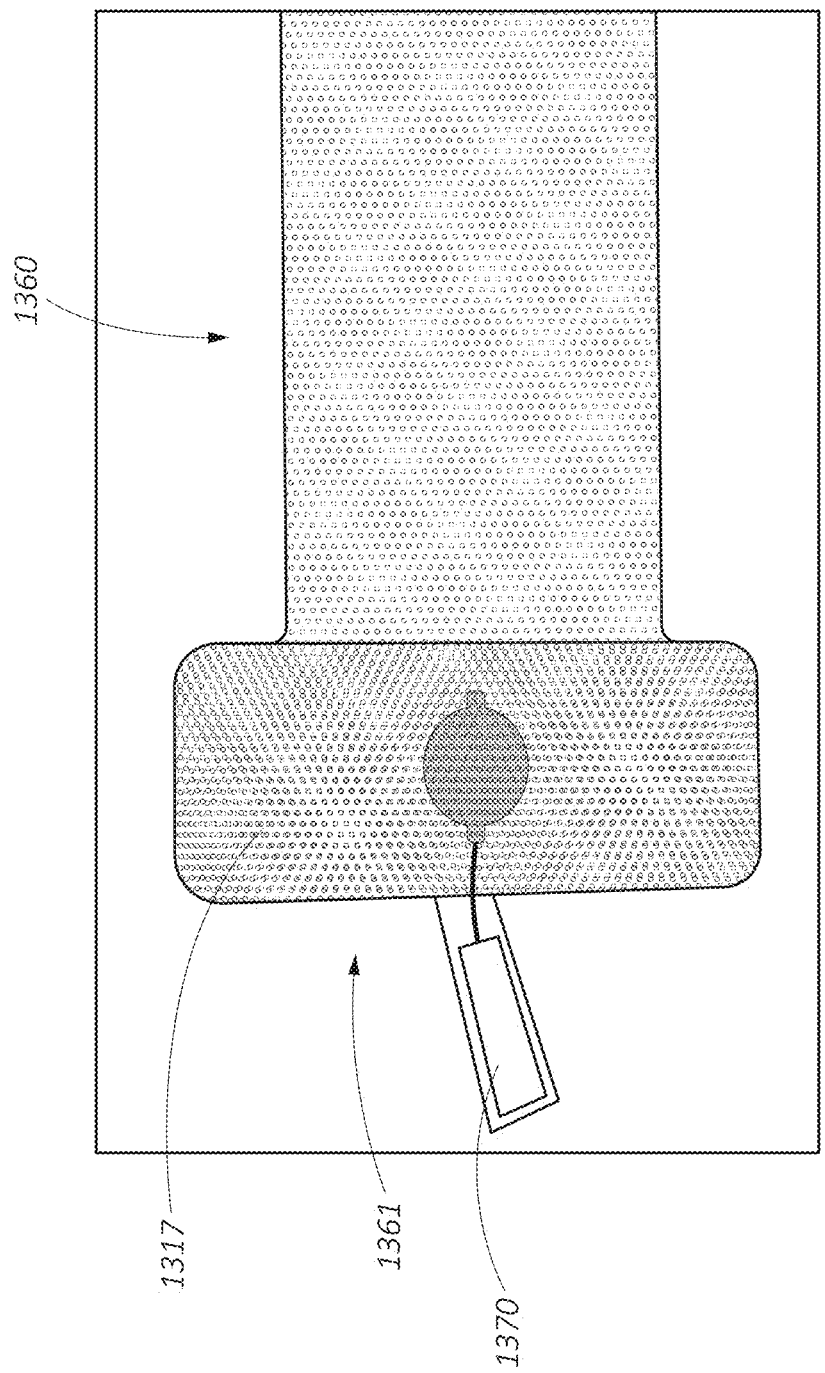

FIGS. 16 and 17 show a top view of the wound dressing with the electronic components 1350 offset from the absorbent layer 1322 with the continuous upper or first spacer layer 1317 shown over the absorbent area 1360 and the electronics area 1361.

Figure 18:
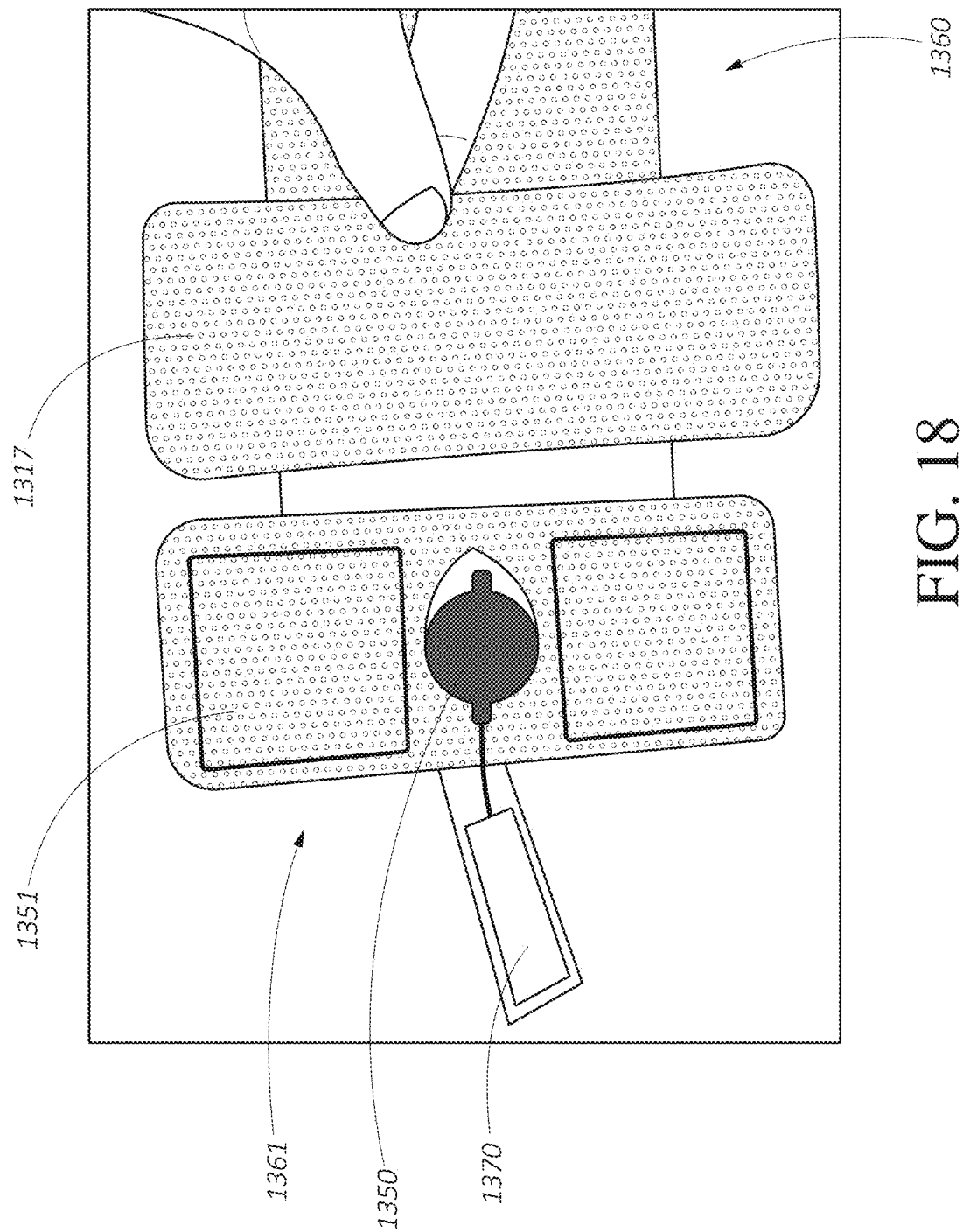
Figure 19:
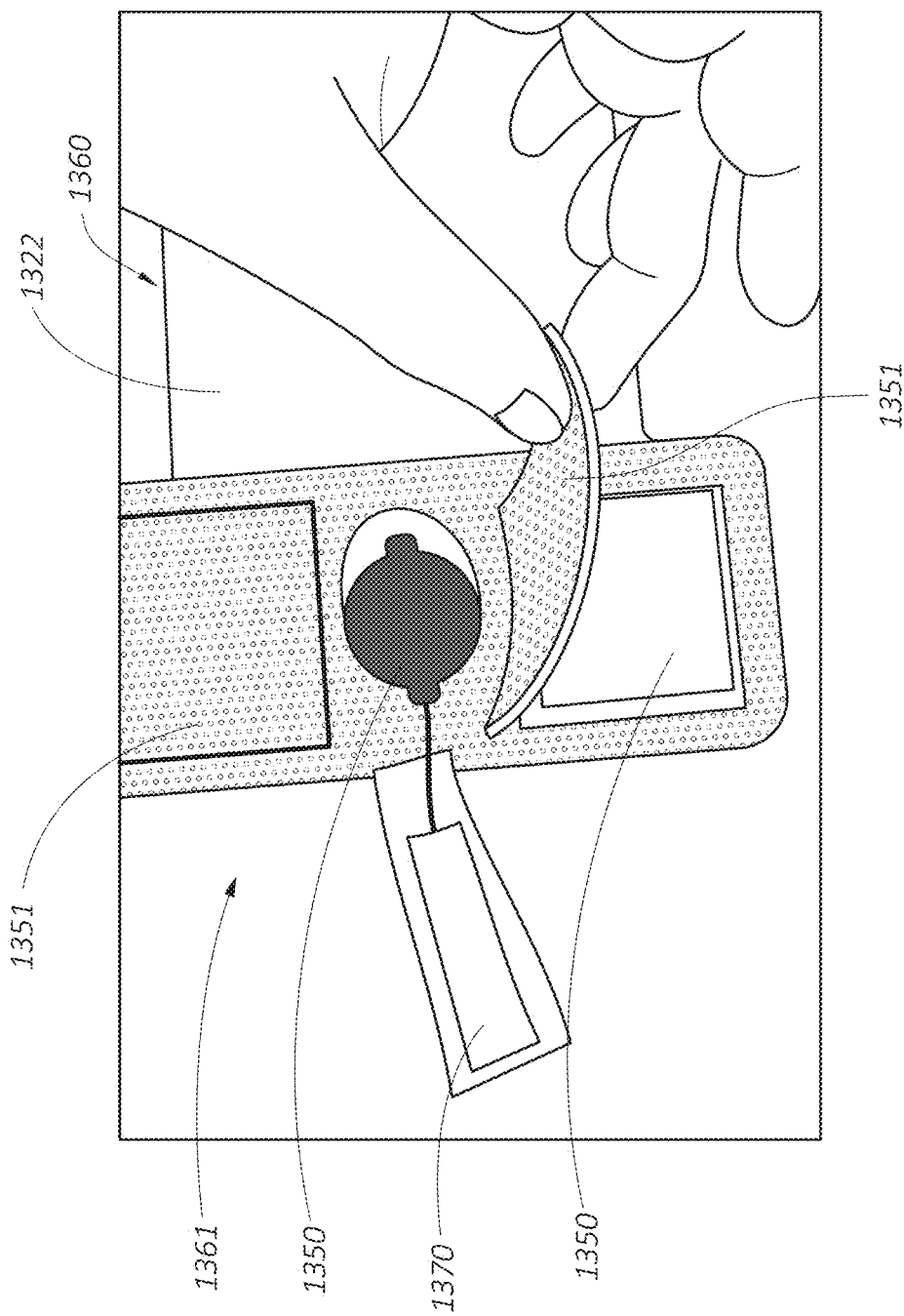
Figure 20:
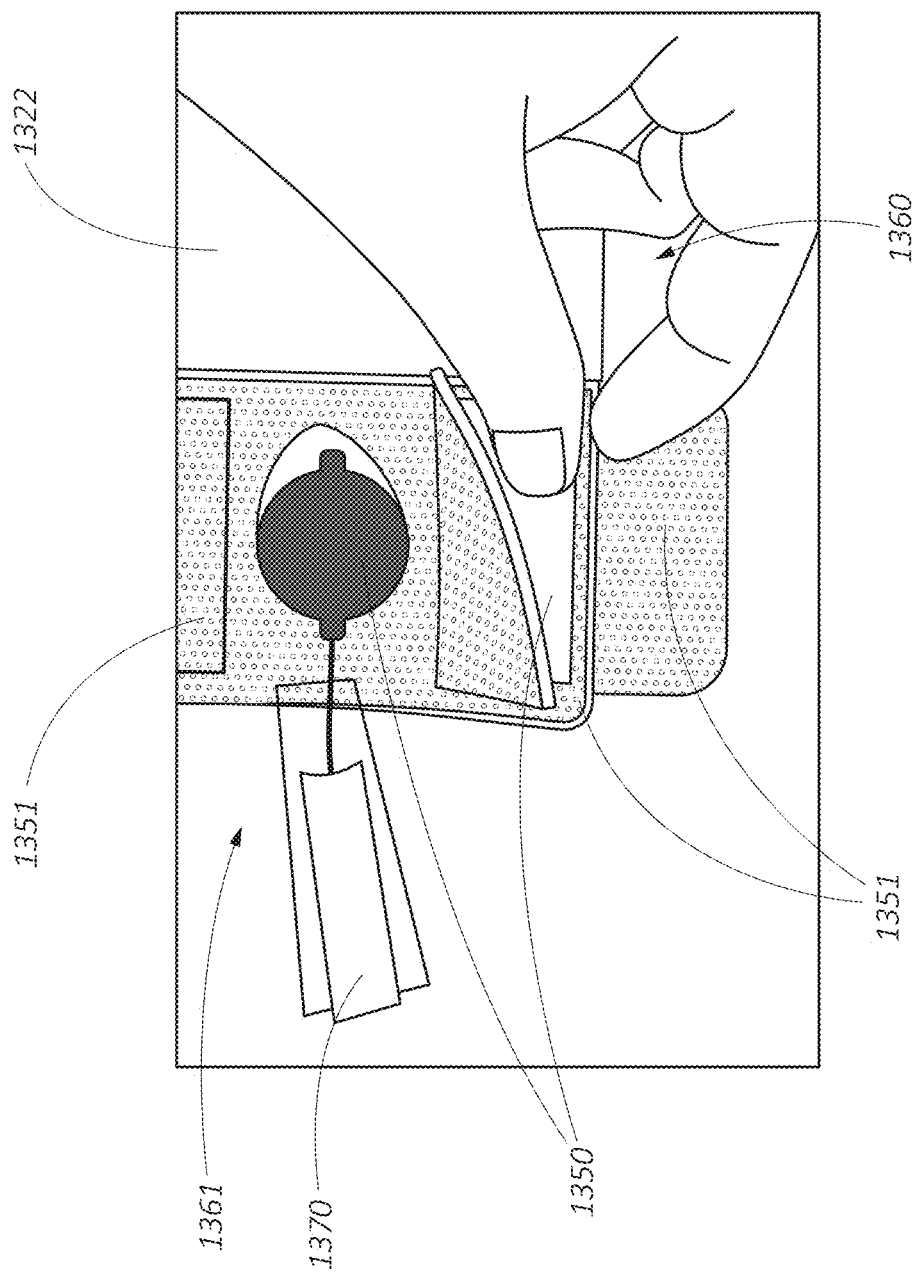

FIG. 18 shows the dressing with a portion of the top or first spacer layer 1317 over the electronic area folded back and exposing underlying spacer layer 1351 in the electronics area and the electronic components 1350. FIG. 19 shows one of the plurality of spacer layers 1351 being removed and exposing the underlying electronic components 1350. FIG. 20 shows one of the plurality of spacer layers 1351 with recesses in spacer layer with an electronic component embedded within the recess.

Figure 21:
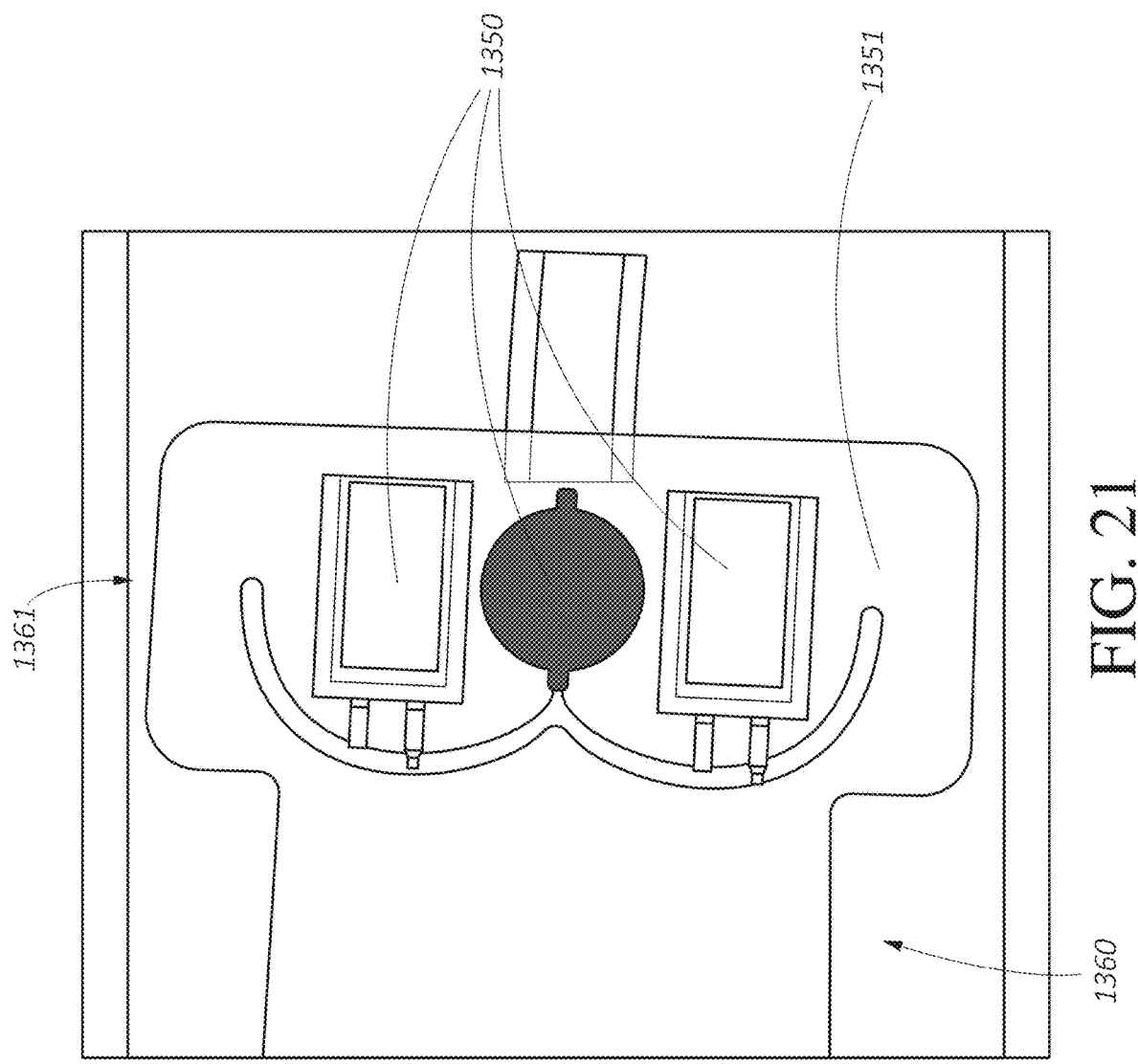
Figure 22:
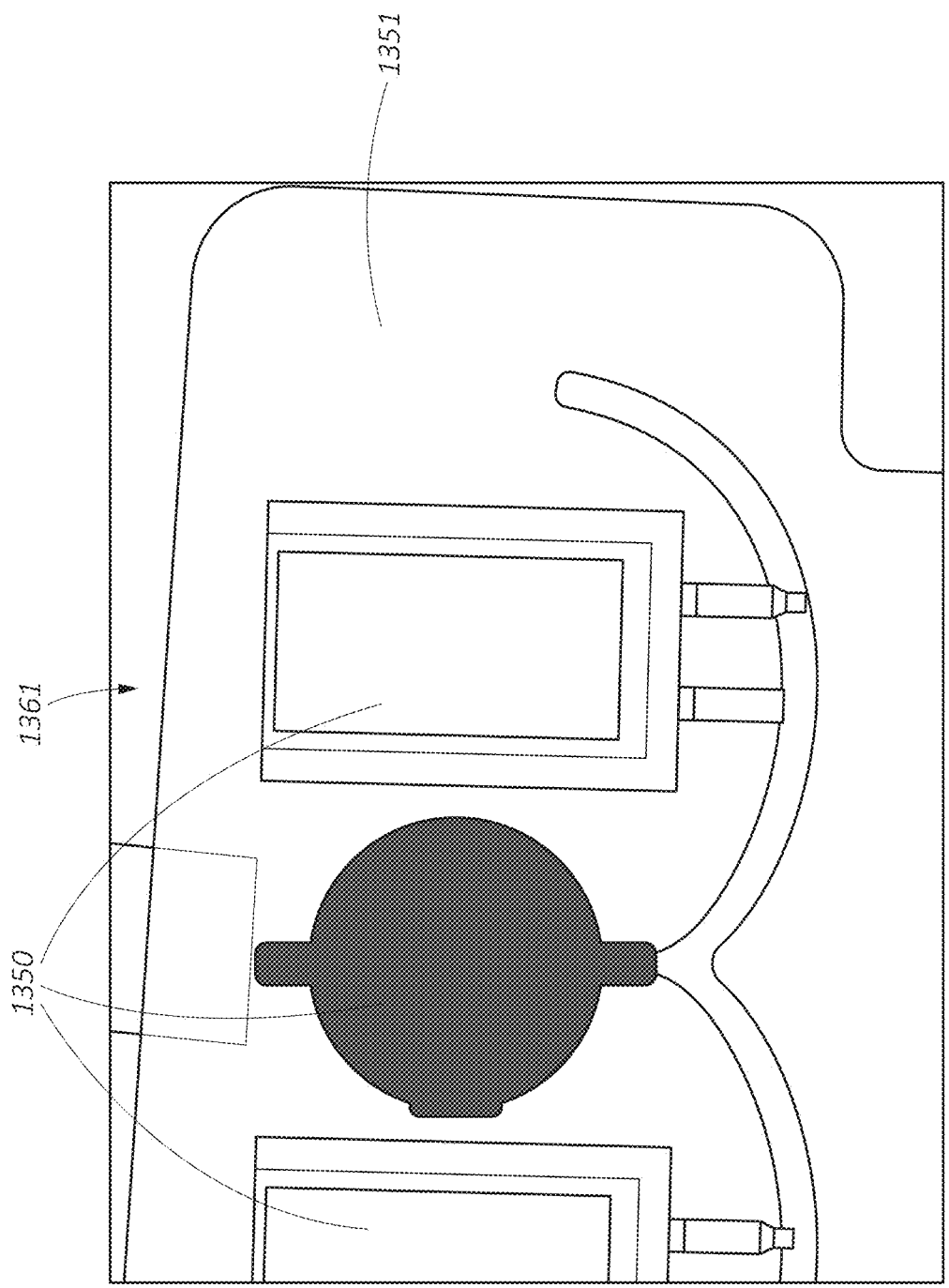
Figure 23:
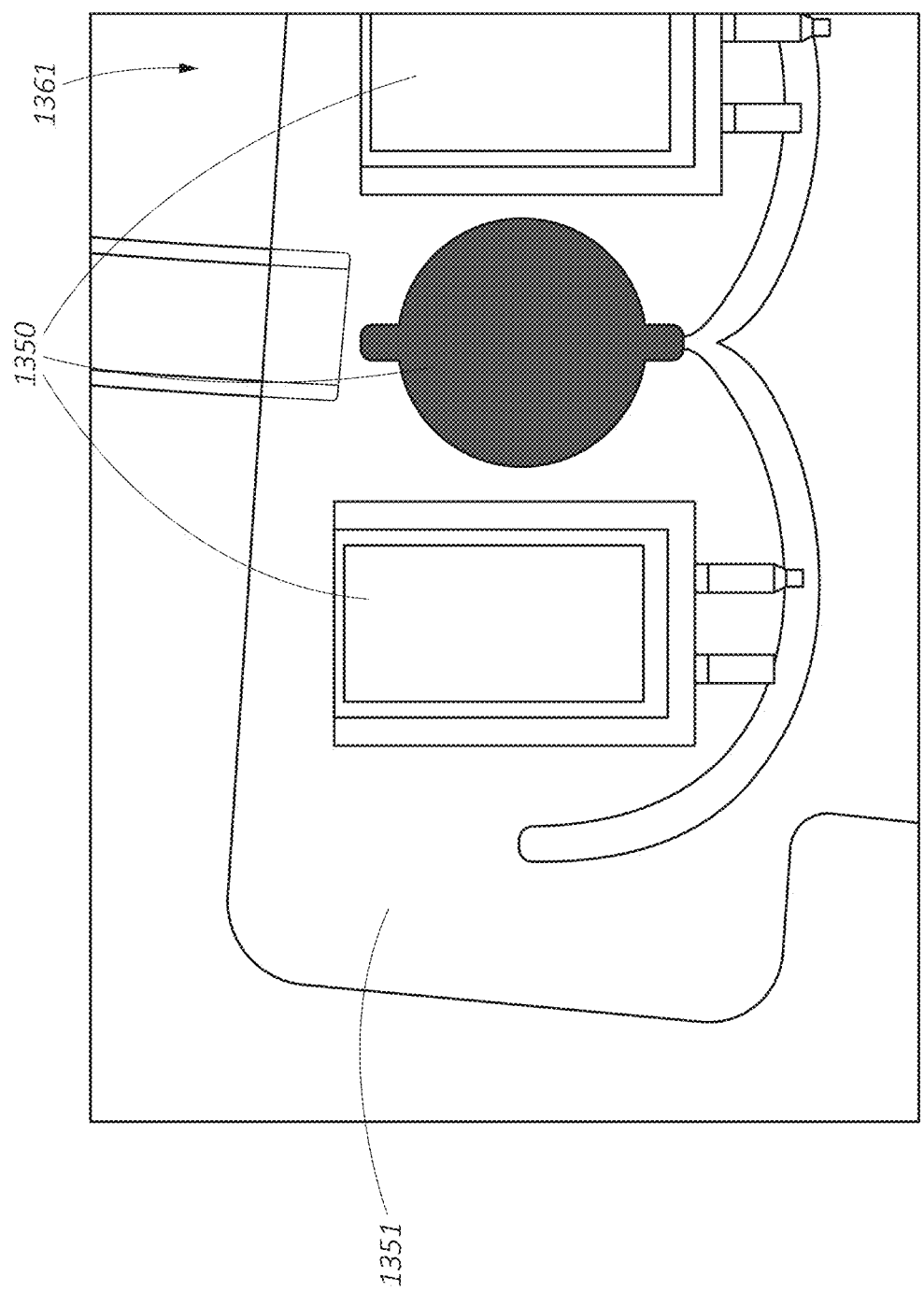
Figure 24:
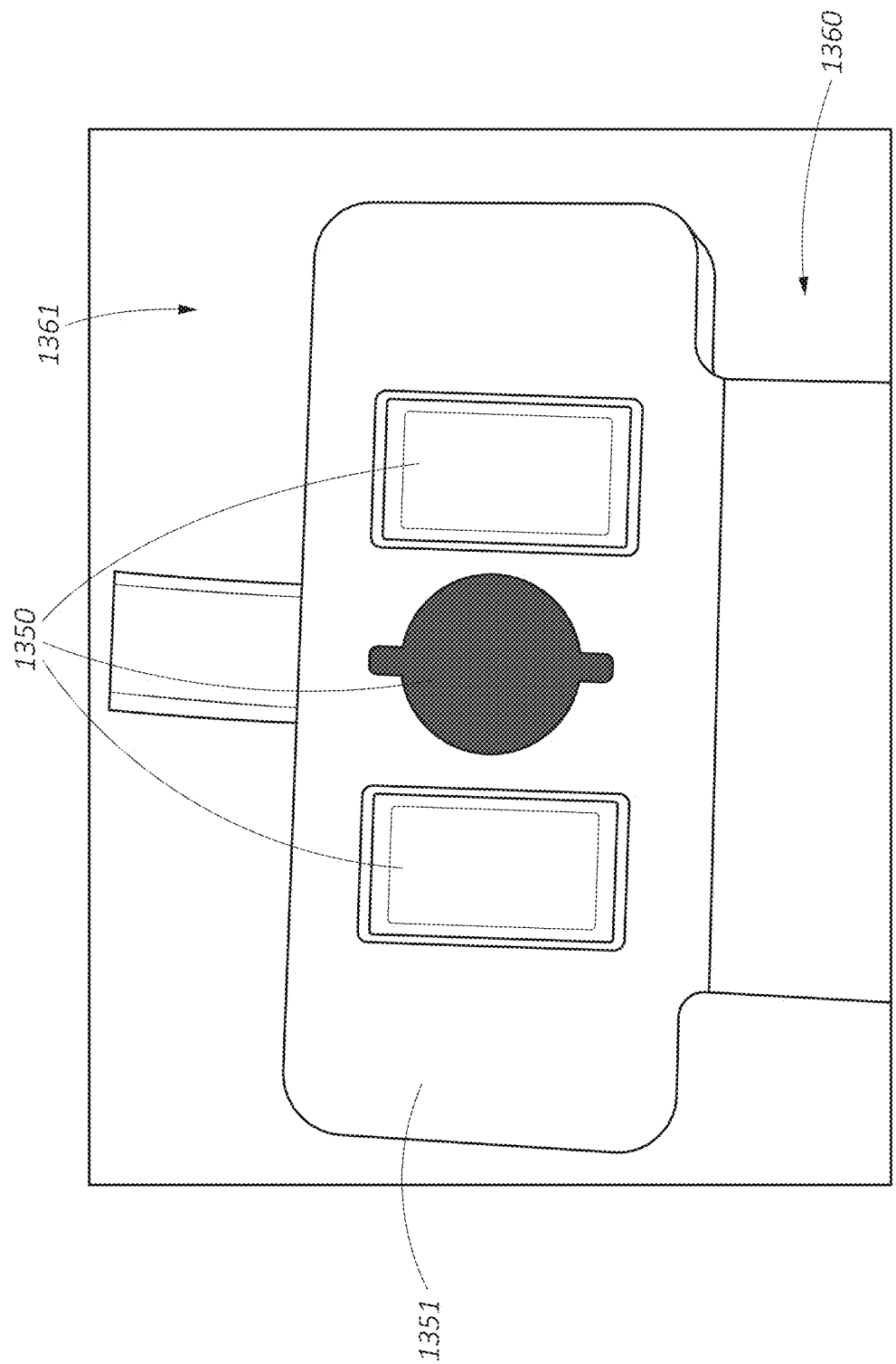
Figure 25:
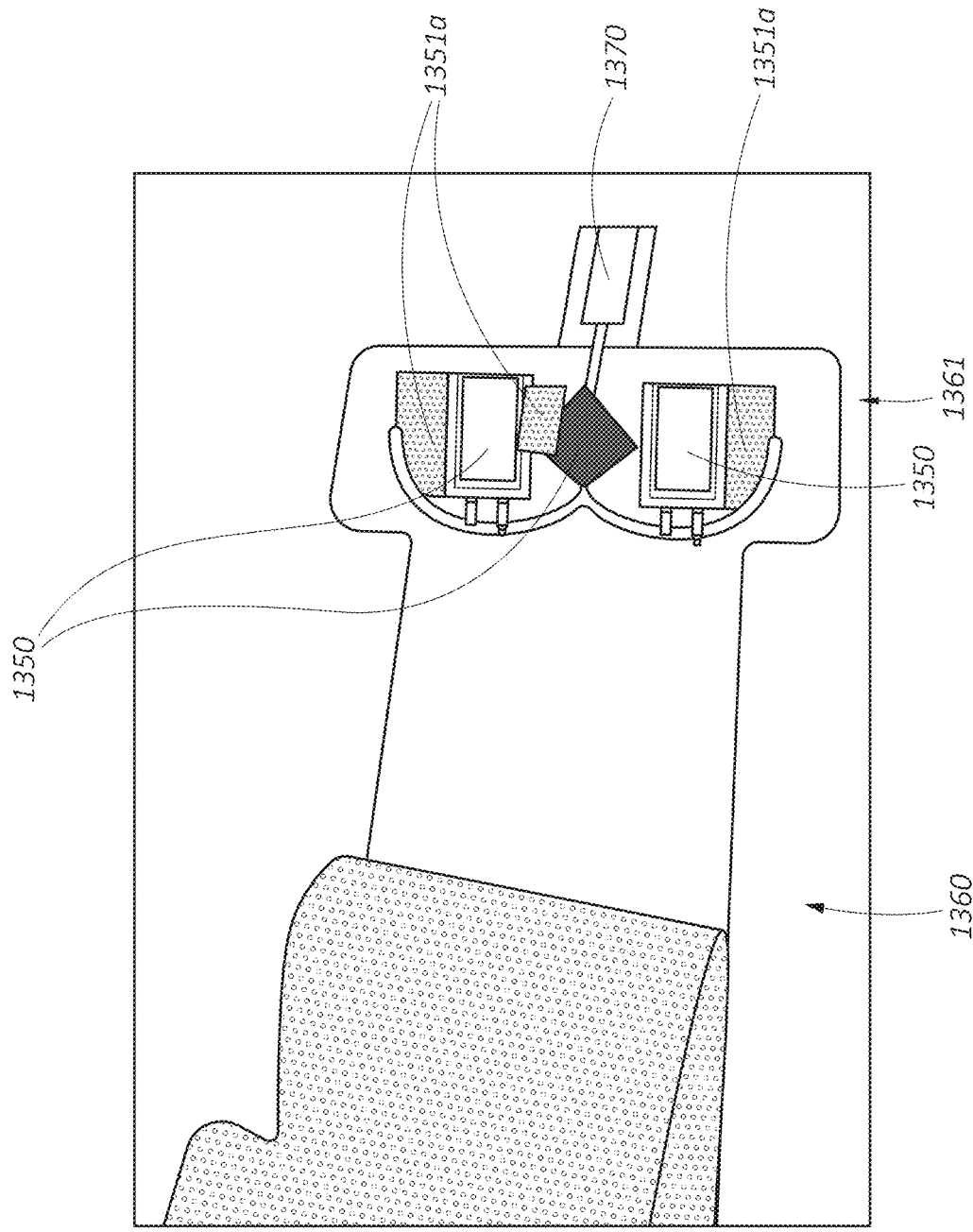
Figure 26:
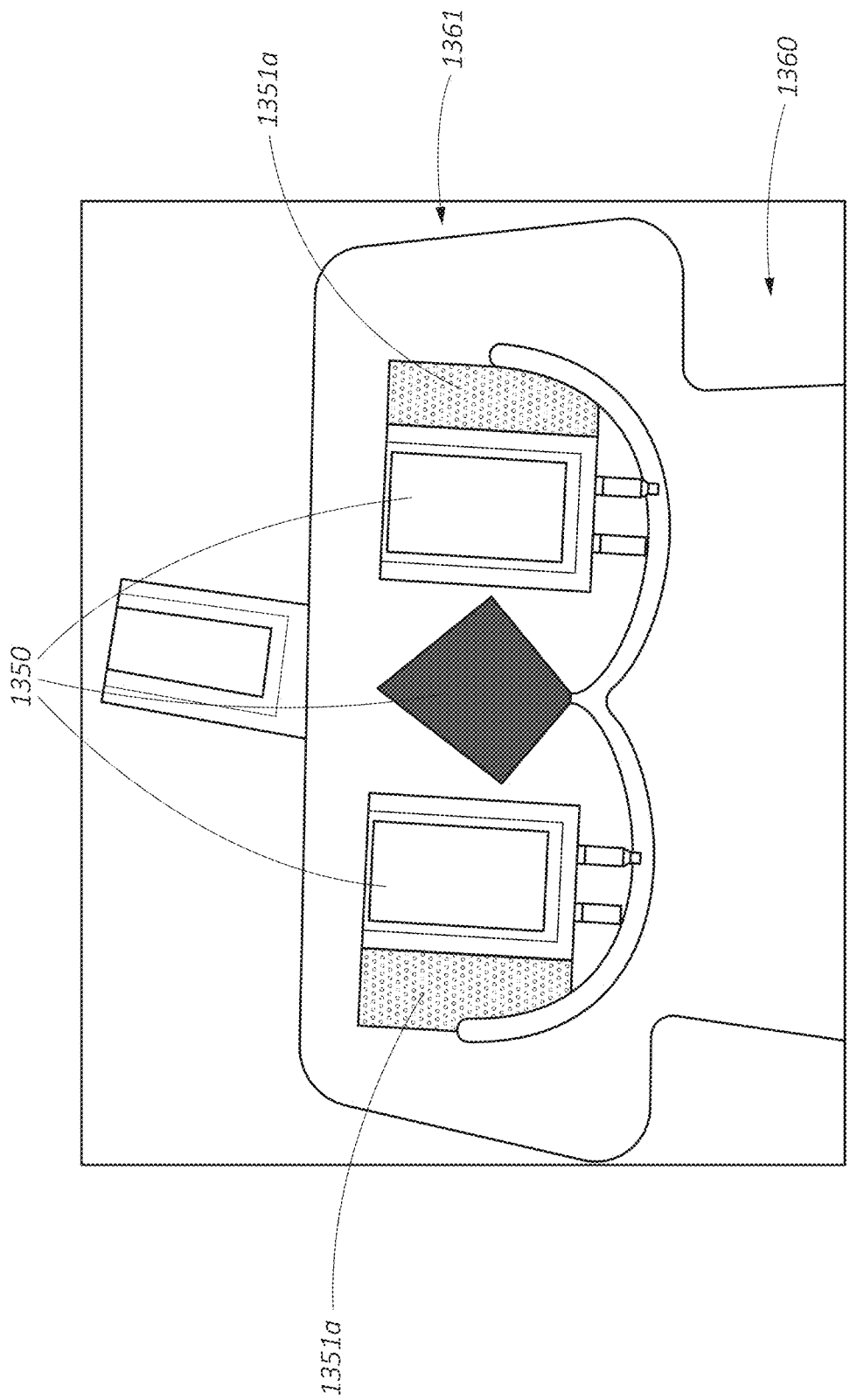
Figure 27:
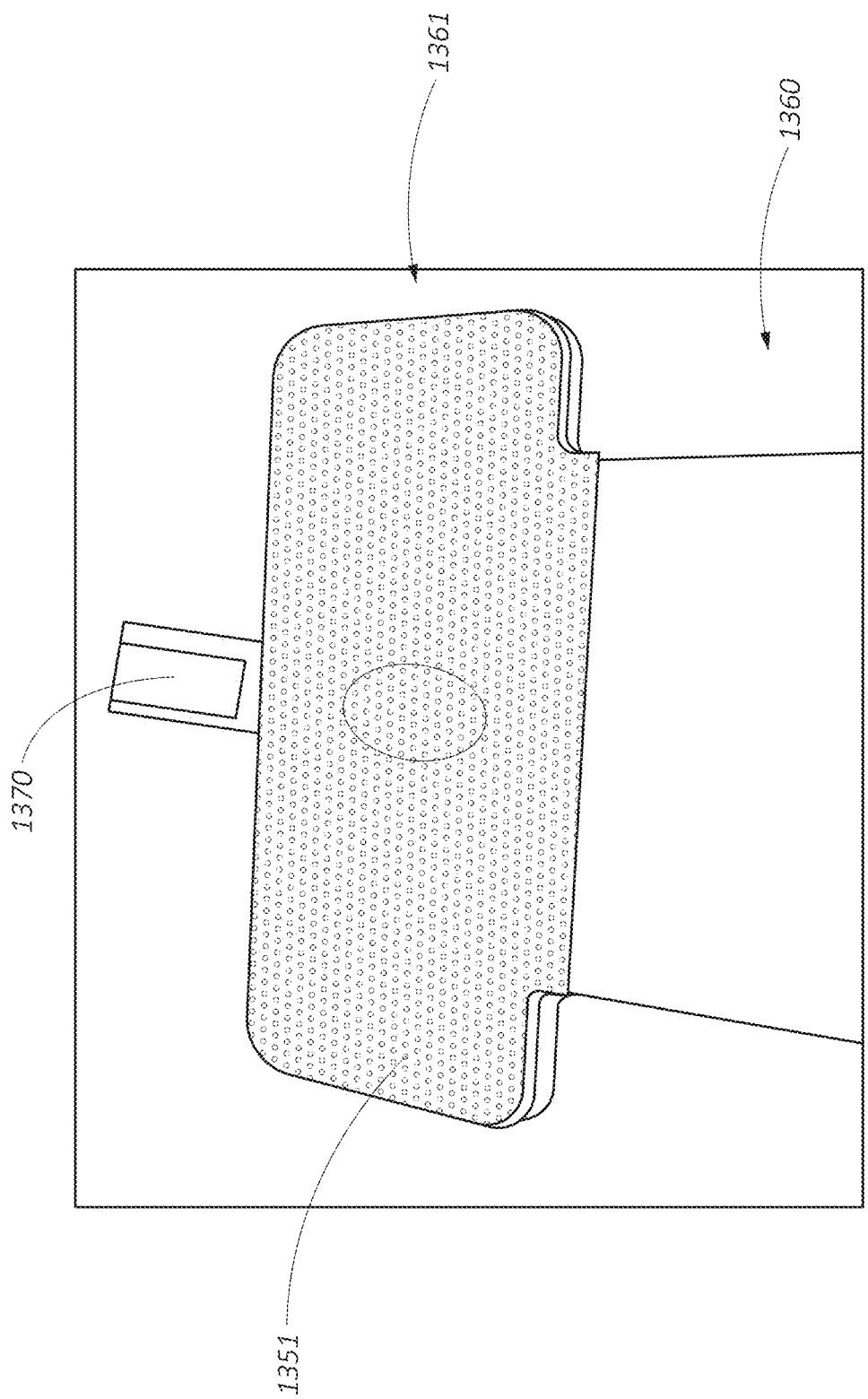

FIGS. 21-23 shows the wound dressing with the electronic components 1350 exposed and the recessed spacer layers removed. At least one of the plurality of transmission layers 1351 are provided below the electronic components 1350 for cushioning as shown in FIGS. 21-23. FIG. 24 shows an embodiment of a wound dressing with a spacer layer 1351 with recesses provided around the electronic components 1350. FIGS. 25-26 show the wound dressing with pieces of spacer material 1351a placed around the electronic components 1350. FIG. 27 shows the wound dressing with the pieces of spacer material 1351a and an additional layer of spacer material 1351 provided over it. In some embodiments, the dressing material in the electronics area can be a material that has the same compressibility as the absorbent material. This can allow for the electronics area to have a uniform surface with the absorbent area when compressed.

The dressings described in FIGS. 13-27 incorporate electronic components in a portion of the dressing offset from the portion of the dressing placed over the wound. Components can be incorporated into the dressing to provide a barrier that stops liquid from entering into the area near the electronics. One of those methods described with reference to FIG. 14 includes the use of a partition or non-porous dam positioned between a portion of the electronics area and the absorbent area. In some embodiments, the dressing can be composed of two separate pouches and a port that connects the two pouches with a filter over the negative pressure port. For example, the dressing can include an electronics pouch and a dressing pouch and the wound dressing can utilize a fluidic connector positioned between the two pouches. The two pouches can be connected or enclosed by a wound contact layer and wound cover layer sealed around the two pouches thereby incorporating the pouches into one dressing unit. In some embodiments, the fluidic connector in communication with the two pouches can be a flexible fluidic connector that comprises a 3D material that allows for pressure to be applied without collapse of the connector. Examples of an application where additional disclosure relating to the fluidic connector can be found include US Publication No. 2015/0141941, titled "Apparatuses and Methods for Negative Pressure Wound Therapy" published on May 21, 2015. The disclosure of this patent is hereby incorporated by reference in its entirety.

In some embodiments, the absorbent components and electronics components can be overlapping but offset. For example, a portion of the electronics area can overlap the absorbent area, for example overlapping the superabsorber layer, but the electronics area is not completely over the absorbent area. Therefore, a portion of the electronics area can be offset from the absorbent area and only provided over the cushioning spacer layers.

Figure 28A:
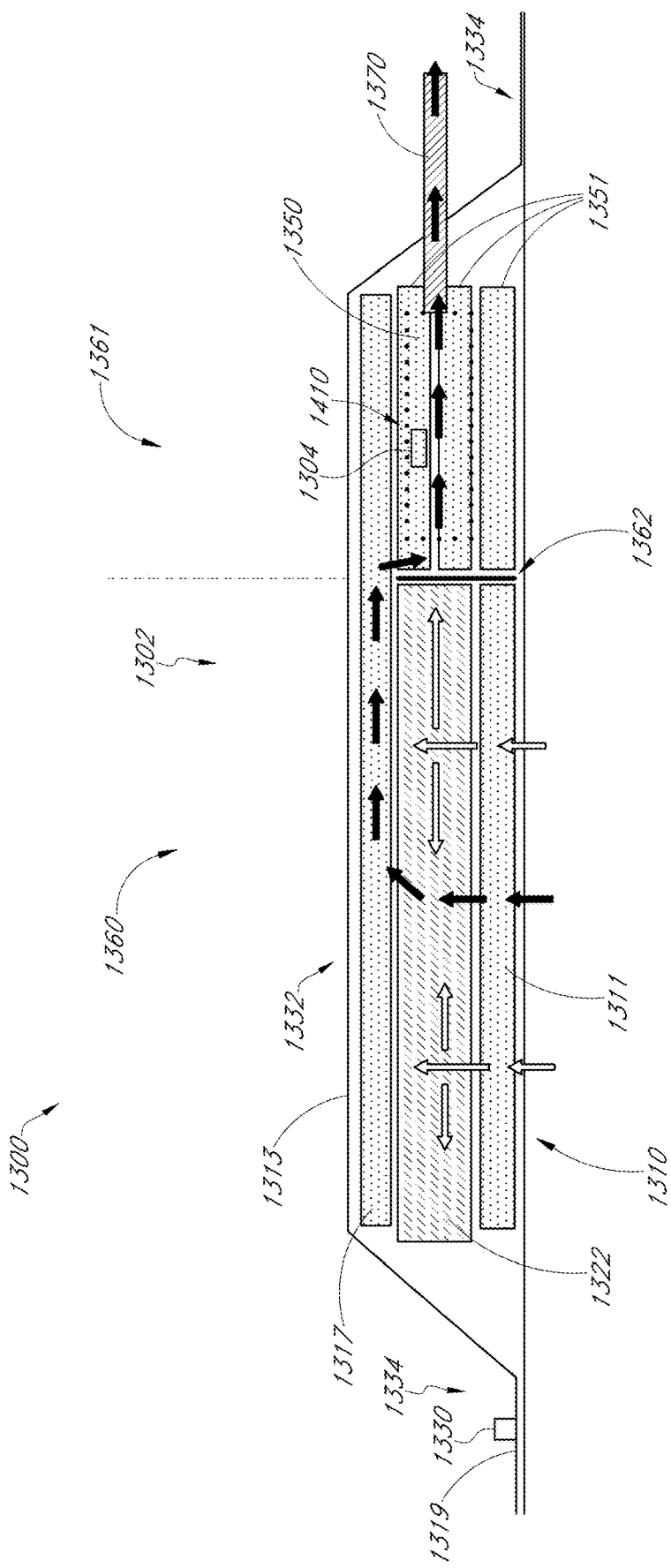
FIG. 28A illustrates a side cross-sectional view of an embodiment of a wound dressing system.

FIG. 28A is a side cross-sectional view of a wound dressing system 1300, according to some embodiments. FIG. 28A illustrates a cross-sectional view of the wound dressing system with components of the wound dressing system similar to the wound dressing system as illustrated in FIG. 14. Unless otherwise noted, reference numerals and like-named components in FIG. 28A refer to components that are the same as or generally similar to the components of FIG. 14. As shown in FIG. 28A, the wound dressing system 1300 can include a wound dressing 1302 with one or more embedded (also referred to as integrated) electronic components 1350. The wound dressing 1302 can include a wound dressing body 1332 and a wound dressing border 1334. The wound dressing border 1334 can extend around at least a portion of the perimeter of the wound dressing body 1332. For example, in some embodiments, the wound dressing border 1334 can extend around the entire perimeter of the wound dressing body 1332. The wound dressing border 1334 can extend away from the wound dressing body 1332 any suitable distance (also referred to as the border length), such as, for example, a distance in the range of about 0.5 cm to about 3.0 cm, although any suitable distance is contemplated, including distances shorter than 0.5 cm or longer than 3.0 cm. Different portions of the wound dressing border 1334 can have different border lengths. For example, for wound dressings 1302 that have generally rectangular shapes, the border lengths of the four corners can be longer relative to the border lengths of the four straight portions of the wound dressing border 1334. The wound dressing 1302 can include an absorbent area 1360 and an electronics area 1361. In some embodiments, the electronic components 1350 can be positioned within the wound dressing 1302 in the electronics area 1361, although it should be appreciated that the electronic components 1350 can be integrated with the wound dressing 1302 in any suitable arrangement (e.g., disposed on and/or positioned within the wound dressing 1302, among others). The electronic components 1350 can optionally include a pump 1304, a power source, a controller, and/or an electronics package, although any suitable electronic component is appreciated. The pump 1304 can be in fluidic communication with one or more regions of the wound dressing 1302, such as, for example, the absorbent area 1360 of the dressing. The absorbent area 1360 and the electronics area 1361 of the wound dressing 1302 can have any suitable arrangement. For example, FIG. 28A illustrates an embodiment of the wound dressing 1302 in which the electronics area 1361 is offset from the absorbent area 1360.

As shown in FIG. 28A, the wound dressing system 1300 can include a switch 1330 to control the operation of the wound dressing system 1300. The switch 1330 can be integrated with the wound dressing 1302. For example, in some embodiments, the switch 1330 can be integrated with the wound dressing body 1332 or the wound dressing border 1334. The switch can be positioned within, disposed on, and/or embedded in the wound dressing body 1332 or the wound dressing border 1334, although it should be appreciated that the switch 1330 can be integrated with any suitable part of the wound dressing 1302. For example, as described in more detail below, in some embodiments, the switch 1330 can be positioned over a flexiboard layer and/or positioned on a tab. The flexiboard layer and/or tab can allow for the switch 1330 to be actuated (e.g. activated, deactivated, and/or selected) without causing trauma or discomfort to users' wound sites. Accordingly, even when users actuate the switch 1330 with compressive and/or shear forces (e.g., from pushing down on the switch or pressing on the switch in a plurality of directions), the flexiboard layer and/or tab advantageously inhibits or reduces the amount of force transferred to users' wound sites. For example, the flexiboard layer can absorb and/or dissipate forces before they reach the wound site.

The switch can be electrically connected to one or more of the electrical components 1350 of the wound dressing system 1300. For example, in some embodiments, the switch 1330 can be electrically connected to the pump 1304, a power source, a controller, and/or an electronics package, although any suitable electronic component is appreciated. In some embodiments, the switch can be wired and/or be in wireless communication with one or more of the electrical components 1350. The switch 1330 can be selectively operable to control one or more of the electrical components 1350. For example, in some embodiments, the switch can be actuated by users to turn on and turn off the pump 1304 and/or a power source. In some embodiments, the switch 1330 can be selectively operable by users to control one or more operating conditions of the pump 1304 (e.g., to toggle through a plurality of operating states or levels of the pump 1304) in addition to or instead of powering on and powering off the wound dressing system 1300. For example, the switch 1330 can be electrically connected to a controller of the wound dressing system 1300 such that users can control various features of the pump 1304, including, for example, the negative pressure level delivered by the pump 1304 (e.g., pressure levels in the range of about −40 mmHg to −150 mmHg, among others), the type of pressure wave delivered by the pump 1304 (e.g., sinusoidal, sawtooth, and the like), and/or the operating mode of the pump 1304 (e.g., continuous or intermittent). For example, in some embodiments, one press of the switch 1330 can turn on the pump 1304 and cause the pump 1304 to deliver a target pressure of −40 mmHg, two presses of the switch 1330 after the pump 1304 has been turned on can cause the pump 1304 to deliver a target pressure of −80 mmHg, and holding the switch 1330 down for a predetermined amount of time (e.g., 2 seconds) can cause the pump 1304 to turn off Other actuation combinations for controlling the wound dressing system 1300 with the switch 1330 are also appreciated. In some embodiments, a plurality of switches can be integrated with the wound dressing 1302 to control the wound dressing system 1300.

FIG. 28B is a perspective view of a wound dressing system 1300 with a switch 1330 embedded into a wound dressing border 1334, according to some embodiments. FIG. 28C also includes a magnified partial perspective view of the corner of the wound dressing system 1300 that includes the switch 1330. Unless otherwise noted, reference numerals and like-named components in FIG. 28B and 28C refer to components that are the same as or generally similar to the components of FIG. 28A. As shown in FIG. 28B, the wound dressing system 1300 can include an exhaust system 1370 to exhaust air from a pump embedded in the wound dressing 1302 to the outside of the wound dressing 1302 (e.g., to the environment). The exhaust system 1370 can be similar to the exhaust system described in more detail below.

As shown in FIG. 28B and 28C, the switch 1330 can optionally be positioned on a corner of the wound dressing border 1334. However, it should be appreciated that the switch 1330 can be integrated with the wound dressing border 1334 or the wound dressing body 1332 at any suitable location. In some embodiments, the switch 1330 can optionally be positioned in a sub-flush position relative to the cover layer 1313 to inhibit or prevent accidental and/or inadvertent actuation of the switch 1330 (e.g., from a user laying on the wound dressing 1302). For example, a bottom surface of the switch 1330 can be positioned below a top surface of the cover layer 1313 (e.g., so that the height of the switch 1330 does not extend past a plane defined by the wound dressing border 1334).

The partially magnified perspective view of the corner in FIG. 28C shows that the wound dressing system 1300 can include one or more indicators 1331. The one or more indicators 1331 can extend (e.g., circumferentially extend) around at least a portion of the perimeter of the switch 1330. The one or more indicators 1331 can indicate one or more statuses of the wound dressing system 1330, such as, for example, battery level (e.g., above 30% remaining and 30% or less remaining), pressure level (e.g., a first pressure level and a second pressure level), operating problems (e.g., a leak and/or a blockage condition), among any other suitable statuses. In some embodiments, the one or more indicators 1331 can include one or more visual indicators, audio indicators, tactile indicators, and the like. For example, in some embodiments, the one or more indicators 1331 can include one or more light emitting diodes (LEDs). The one or more indicators can include an array of LEDs. In some embodiments, one or more LEDs can, for example, flash or illuminate in a particular color to indicate a particular operating status. For example, the one or more LEDs can flash to indicate the presence of an operating problem (e.g., a leak and/or a blockage condition), illuminate in a solid color to indicate a battery level (e.g., illuminate solid green for a battery level above a threshold percentage (e.g., 30%) and illuminate solid orange for a battery level at or below the threshold percentage). In some embodiments, the switch 1330 can be used to power on and power off one or more electrical components of the wound dressing system 1300, such as, for example, a pump, a power source, a controller, and/or an electronics package, among others. For example, the switch 1330 can be electrically connected to one or more such electrical components via a wire conduit 1340 shown in the partially magnified perspective view in FIG. 28C. The wire conduit 1340 can pass between layers of the dressing. For example, in some embodiments, the wire conduit 1340 can be positioned between the cover layer 1313 and a bottom wound contact layer (not shown).

Figure 29B:
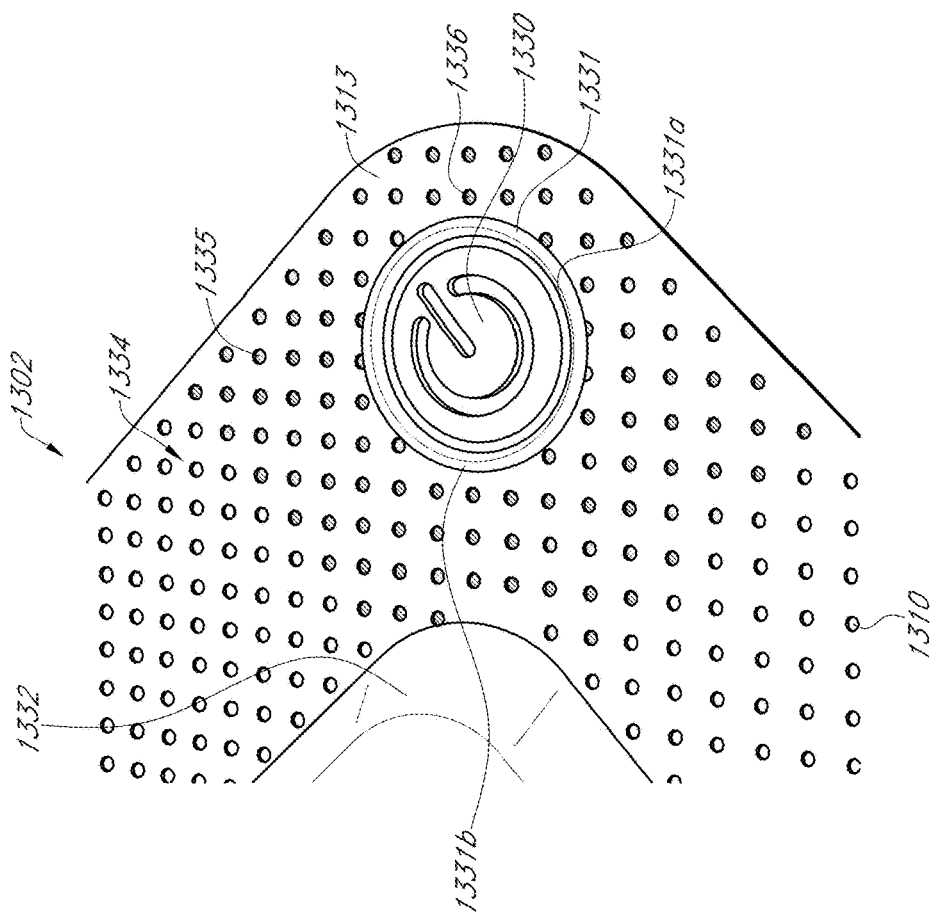
FIGS. 29A and 29B illustrate two views of a switch integrated with a wound dressing.
Figure 29A:
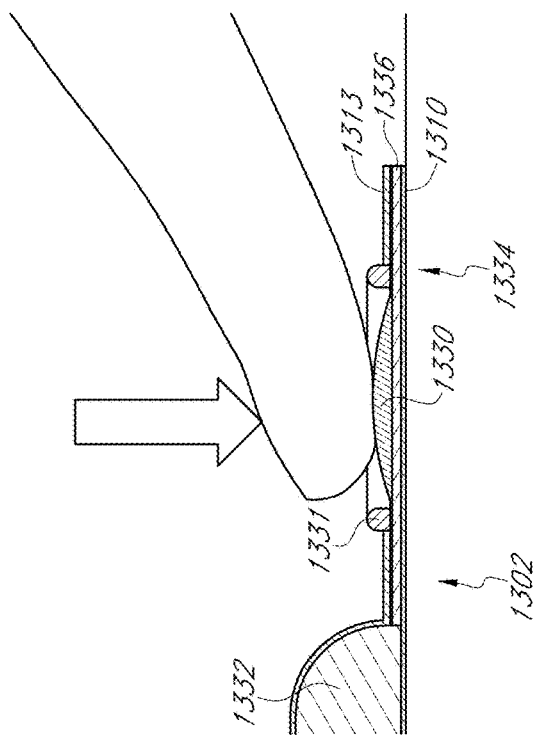

FIGS. 29A and 29B are two views of the switch 1330 of FIGS. 28B and 28C integrated with a wound dressing 1302, according to some embodiments. FIG. 29A is a perspective view of the switch 1330 positioned above a flexiboard layer 1336 and FIG. 29B is a side cross-sectional view of the switch 1330 positioned above the flexiboard layer 1336. Unless otherwise noted, reference numerals and like-named components in FIGS. 29A and 29B refer to components that are the same as or generally similar to the components of FIGS. 28A-28C. As shown in FIG. 29A, the cover layer 1313 of the wound dressing 1302 can include a plurality of holes 1335 (also referred to as breathing pores) to allow air to circulate through the wound dressing border 1334. The flexiboard layer 1336 can be positioned below the cover layer 1313 and the switch 1330 so that when the switch 1330 is actuated (e.g., the switch is pressed, or a force is applied to it) the flexiboard layer 1336 inhibits or reduces the amount of force transferred to the wound site and surrounding tissue. The flexiboard layer 1336 can be any suitable rigid, semi-rigid, and/or semi-flexible material capable of dissipating compression forces on the wound dressing 1302. The extent of the flexiboard layer 1336 in FIG. 29A is shown by the plurality of holes 1335 in the cover layer 1313 that are shaded. The wound contact layer 1310 is shown in FIG. 29A by the plurality of holes 1335 in the cover layer 1313 that are not shaded. In some embodiments, the flexiboard layer 1336 can extend outward from the center of the switch 1330 in the range of about 0.5 cm to 3.0 cm, although any suitable distance is appreciated, including distances shorter than 0.5 cm and distances greater than 3.0 cm. In some embodiments, the one or more indicators 1331 can include a first indicator 1331a and a second indicator 1331b, although any suitable number is appreciated.

FIG. 29B is similar to FIG. 29A except that FIG. 29B is a side cross-sectional view of the switch 1330 of FIG. 28B and 28C embedded in the wound dressing border 1334. As shown in FIG. 29B, the switch 1330 can be positioned above a flexiboard layer 1336. The flexiboard layer 1336 can extend a distance away from a center of the switch 1330. In some embodiments, the flexiboard layer 1336 can extend the width of the wound dressing border 1334 (e.g., the width defined between the wound dressing body 1332 and the outer edge of the wound dressing border 1334). In some embodiments, the one or more indicators 1331 can be positioned adjacent the switch 1330 (e.g., can extend around or can extend circumferentially around the switch 1330). A cover layer 1313 can be positioned around the one or more indicators 1331 and the switch 1330 and on top of the flexiboard layer 1336. The flexiboard layer 1336 can be positioned above the wound contact layer 1310. As shown in FIG. 29B, the switch 1330 can be positioned in a sub-flush position relative to the one or more indicators 1331 to reduce the likelihood of accidental/inadvertent actuation of the switch 1330. A forefinger is shown depressing the switch 1330. In some embodiments, the switch 1330 can be actuated by pressing the switch 1330 in a first direction with a forefinger (e.g., a downward direction).

Figure 30B:
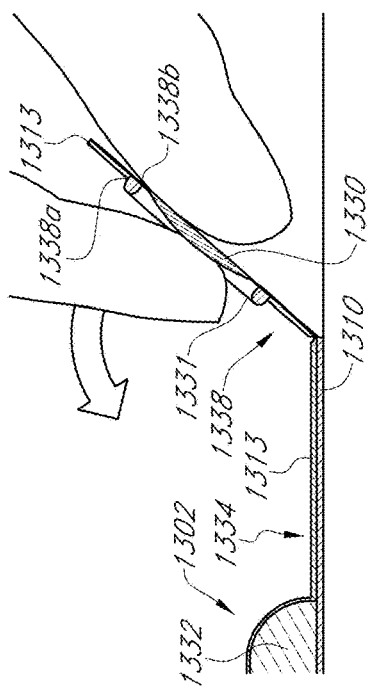
FIGS. 30A and 30B illustrate two views of a switch integrated with a tab that extends away from a wound dressing border.
Figure 30A:
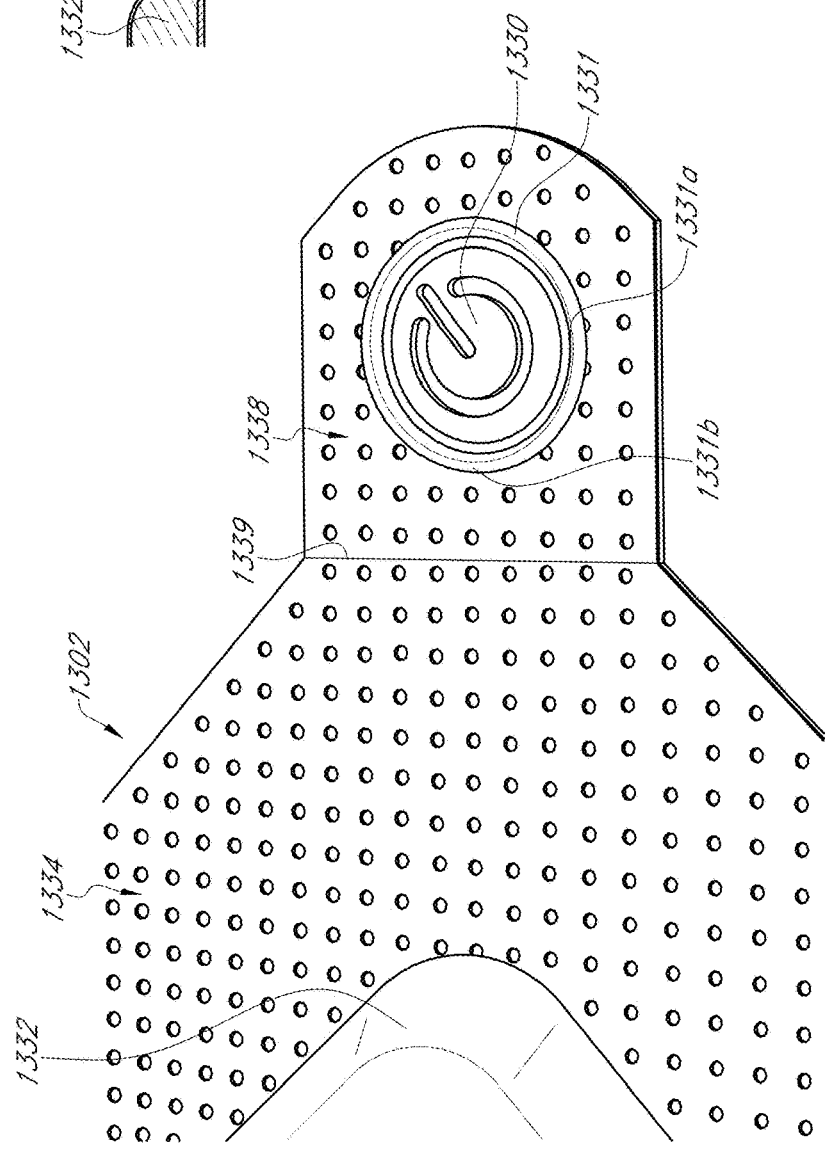

FIGS. 30A and 30B are two views of a switch 1330 integrated with a tab 1338 that extends away from a wound dressing border 1334, according to some embodiments. FIG. 30A is a perspective view of the switch 1330 positioned on the tab 1338 and FIG. 30B is a side cross-sectional view of the switch 1330 positioned on the tab 1338, with the tab 1338 lifted at an angle relative to a plane of the wound dressing 1302. Unless otherwise noted, reference numerals and like-named components in FIGS. 30A and 30B refer to components that are the same as or generally similar to the components of FIGS. 28A-29B. As shown in FIG. 30A, the tab 1338 can be attached to a peripheral edge of the wound dressing border 1334, although any other suitable location is appreciated, such as, for example, the middle of the wound dressing border 1334 or an edge of the wound dressing body 1332, among others. The wound dressing 1302 can optionally include a joint 1339 (also referred to as a seam, a crease, and/or a border) where the tab 1338 and the wound dressing border 1334 attach (or otherwise come together). The joint 1339 can advantageously allow the tab to pivot (also referred to as rotate) about the joint 1339 (e.g., like a hinge) so that users can optionally move the tab 1338 before actuating the switch 1330. In some embodiments, the tab 1338 can have a rest position in which it abuts up against the wound dressing border 1334 (e.g., extends along the same plane as the wound dressing border 1334), the wound dressing body, and/or the patient before a user moves the tab 1338. In some embodiments, the tab 1338 can be lifted about the joint 1339 (e.g., so that it extends at an angle relative to the wound dressing border 1334 and is not in contact with the patient's skin) so that no force is transferred to the patient's body when the switch 1330 is actuated. For example, in some embodiments, the switch 1330 can be actuated by applying a force to the switch 1330 in two opposing directions, such as, for example, on first and second sides of the tab 1338a, 1338b (e.g., by pressing the switch with two fingers, as shown in FIG. 30B). The tab 1338 can therefore allow users to lift up the tab 1338, which advantageously inhibits (e.g., prevents) trauma to the wound and surrounding tissue by actuating the switch 1330, as shown by the two fingers in FIG. 30B (e.g., between a thumb and a forefinger). FIG. 30B shows that the switch 1330 and the one or more indicators 1331 can be attached to the underside of the cover layer 1313. In some embodiments, a flexiboard 1336 can optionally be attached to the tab 1338, such as, for example, below the switch 1330. In some embodiments, the electrical connection between the switch 1330 and the pump in the wound dressing can be positioned between the cover layer 1313 and the wound contact layer 1310, although any suitable arrangement is appreciated. As shown in FIG. 30B, the switch 1330 can be positioned in a sub-flush position relative to the one or more indicators 1331 to reduce the likelihood of accidental/inadvertent actuation of the switch 1330.

Figure 30C:
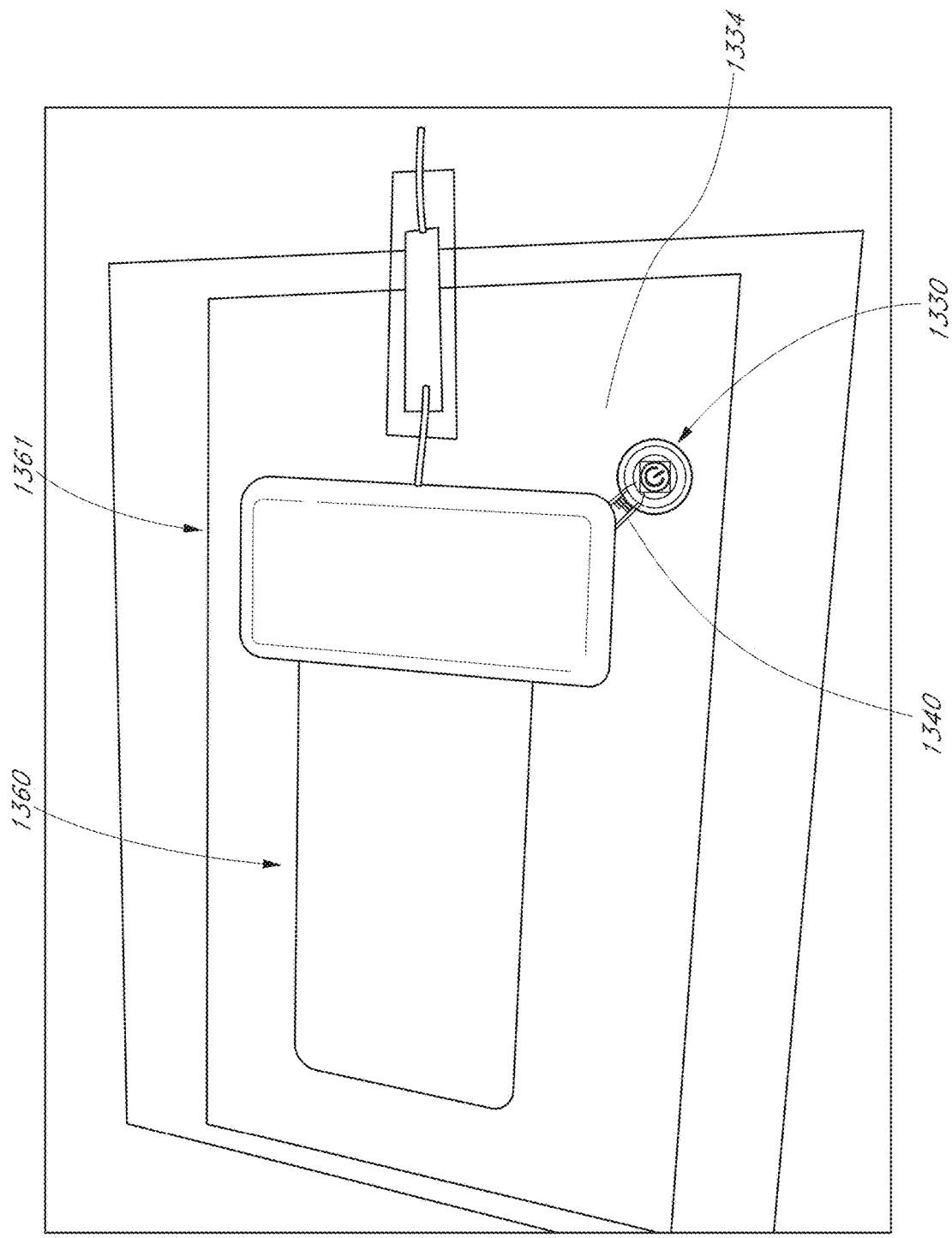
Figure 30D:
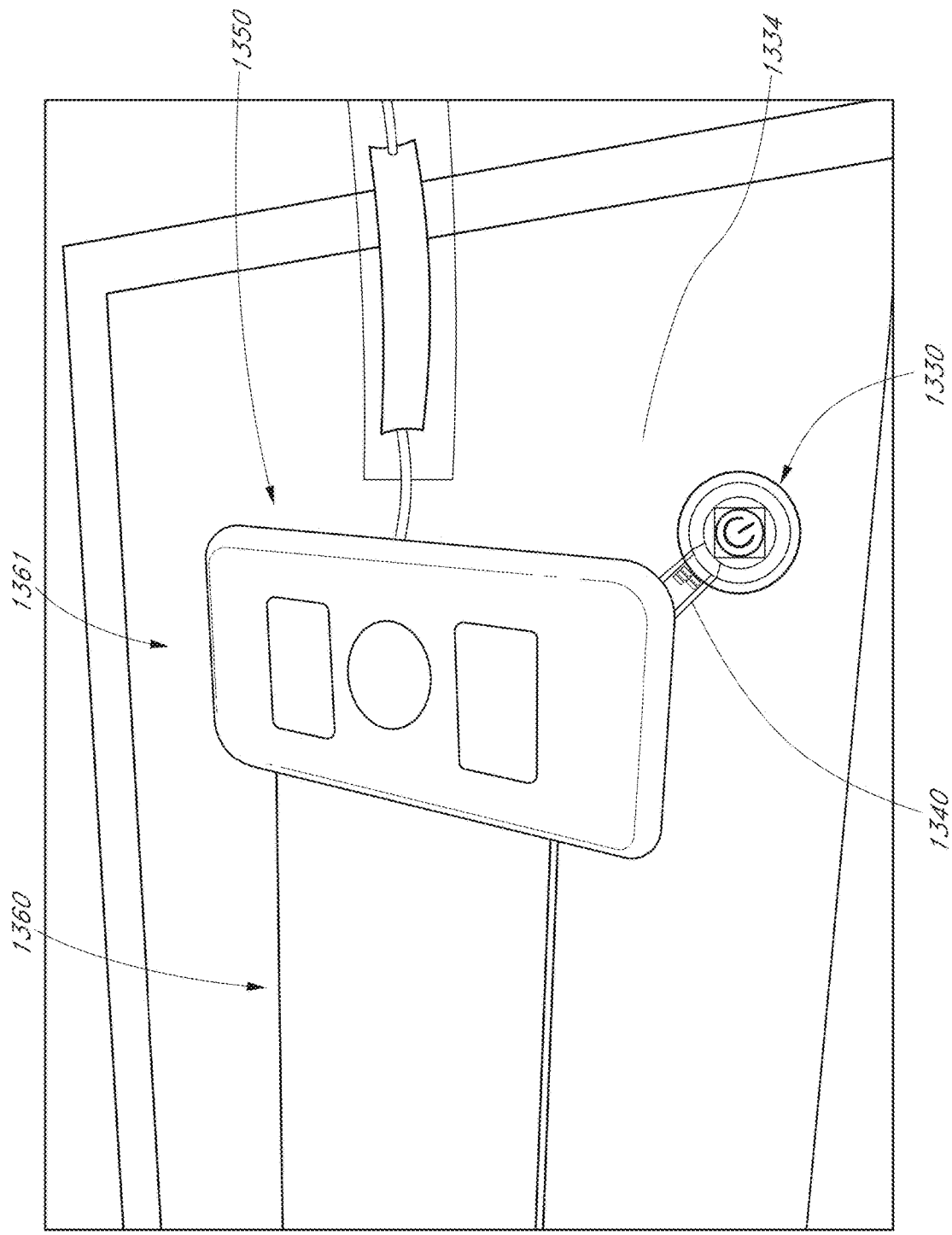
Figure 30E:
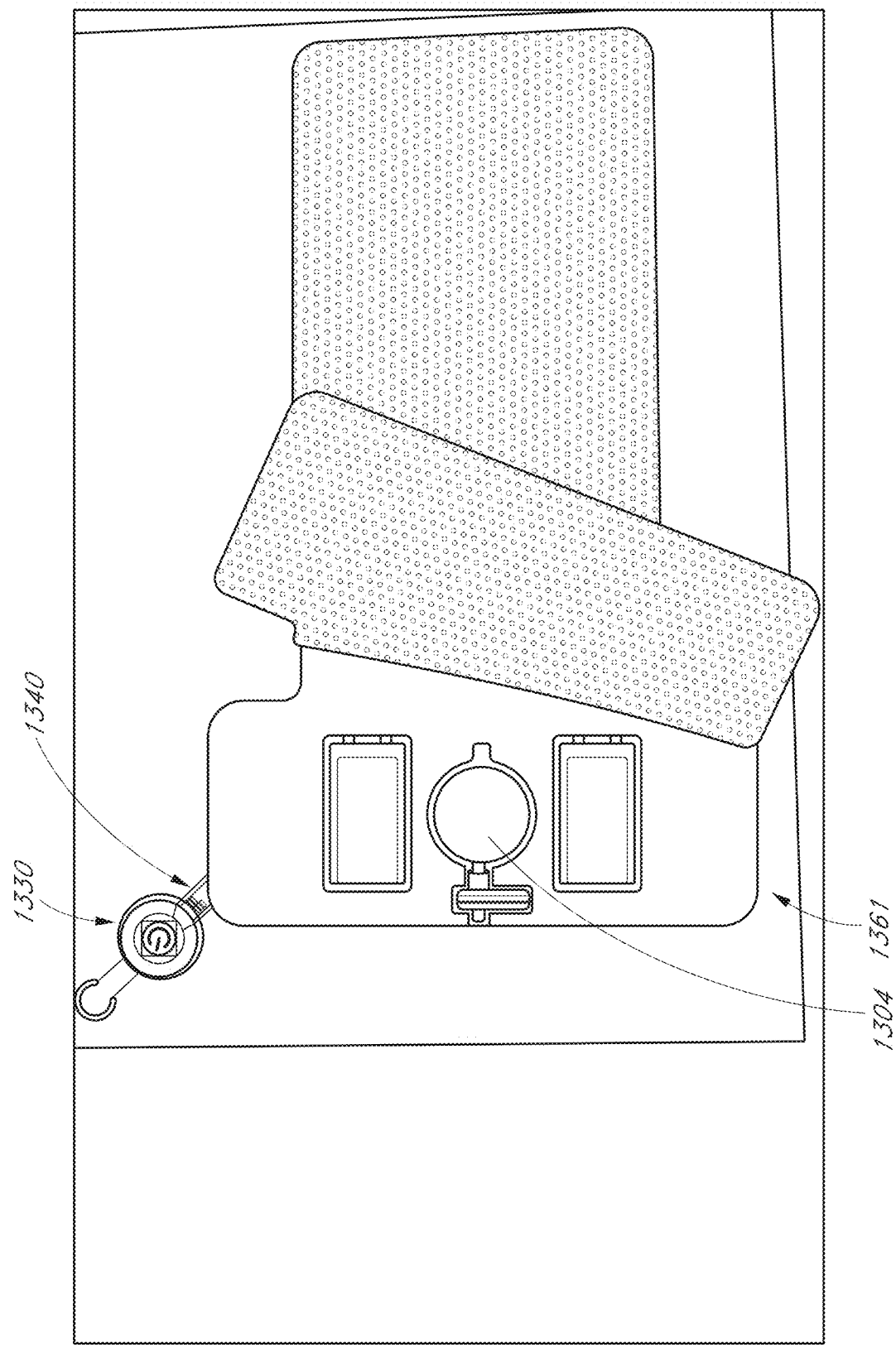

FIGS. 30C-3E show embodiments of wound dressings with a switch 1330 integrated into the wound dressing border 1334. In some embodiments, the switch 1330 can be electrically connected to one or more such electrical components via a wire conduit 1340 shown in FIGS. 30C-3D. The wire conduit 1340 can pass between layers of the dressing. For example, in some embodiments, the wire conduit 1340 can be positioned between a backing or cover layer and a bottom wound contact layer. FIG. 30A illustrates a wound dressing with integrated switch at the wound dressing boarder before negative pressure is applied. FIG. 30D illustrates a wound dressing with integrated switch at the wound dressing boarder after negative pressure is applied. As shown in FIG. 30D, when negative pressure is applied, the wound dressing components are pulled downward and an imprint of the electronic components 1350 is visible in the electronics area of the dressing. FIG. 30E shows the wound dressing components with the backing layer and wound contact layer removed. The switch 1330 is shown adjacent to the dressing layers of the electronics area 1360 and the wire conduit and/or electrical connections 1340 are shown extending from the switch to the electronics area 1360 of the dressing.

As described previously, FIG. 11 illustrates a top view of a wound dressing system with a switch 1160 embedded within a wound dressing body, according to some embodiments. The pump 1116, electronic components 1115, and switch 1160 for operating the pump (e.g., turning the pump on/off), and power source 1114 are visible from the top of the wound dressing. As shown in FIG. 11A, a dressing layer can be positioned over the switch 1160 to keep it sterile.

As shown in FIG. 28A, the negative pressure wound therapy system 1300 can include an exhaust system 1370 (also referred to as a dressing exhaust or a pump exhaust) to exhaust air from the pump 1304 to the outside of the wound dressing 1302 (e.g., to the environment). In some embodiments, the exhaust system 1370 can be in communication with the electronics area 1361 and the environment outside of the dressing 1302. As described in more detail below, in some embodiments, the exhaust system 1370 can be a flexible fluidic connector (also referred to as a flexible port) that includes a 3D material that allows for pressure (e.g., a compression force applied via compression of the wound dressing 1302) to be applied to the exhaust system 1370 without causing the collapse of its exhaust port. Accordingly, even when the wound dressing 1302 and exhaust system 1370 is subjected to a compression force (e.g., from the patient laying on the wound dressing 1302), the exhaust system 1370 advantageously exhausts air from the wound site while inhibiting the collapse and occlusion of the exhaust pathway. Examples of an application where additional disclosure relating to the 3D material can be found include US Publication No. 2015/0141941, titled "Apparatuses and Methods for Negative Pressure Wound Therapy" published on May 21, 2015. The disclosure of this patent is hereby incorporated by reference in its entirety.

Figure 31A:
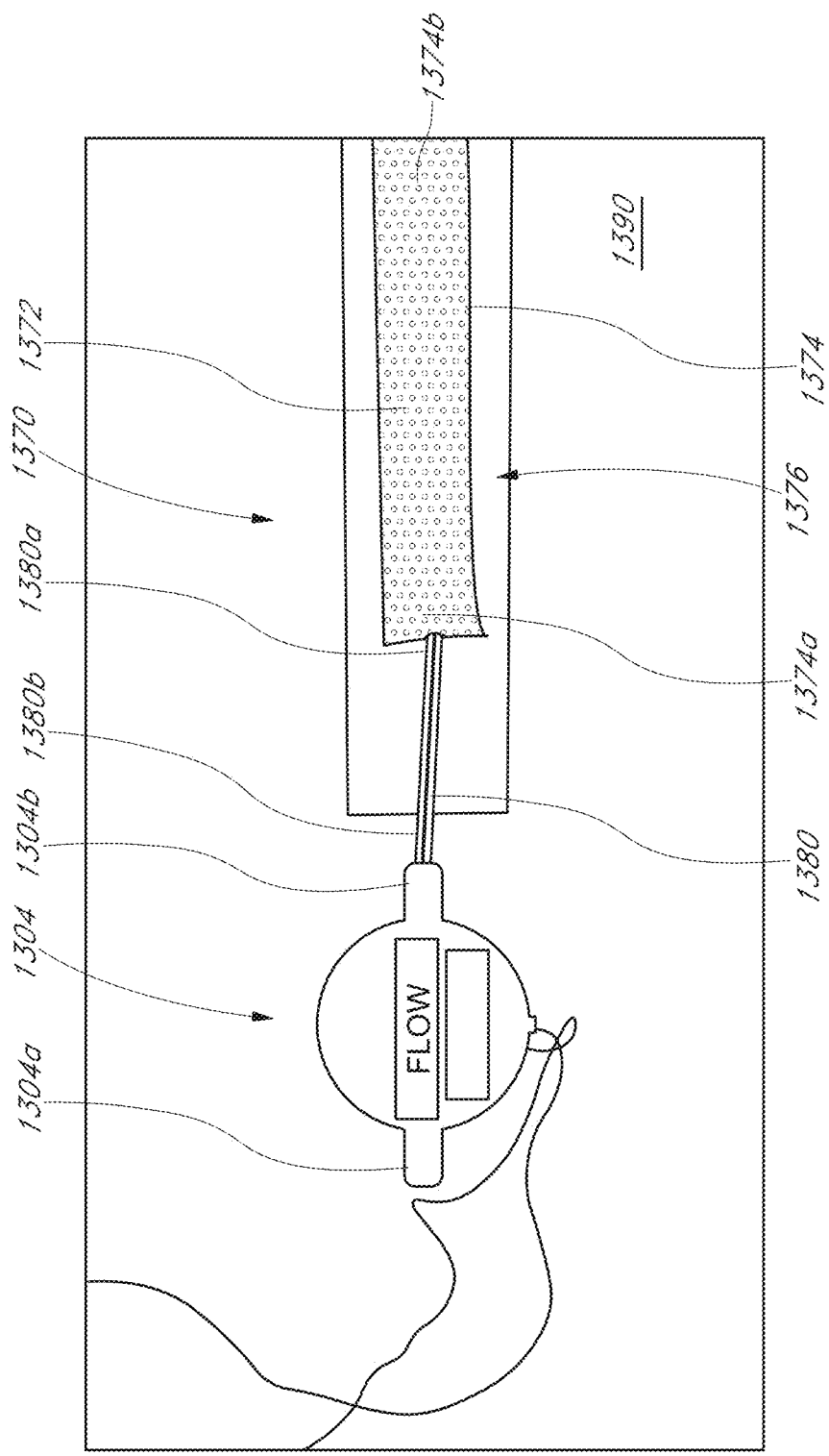
FIG. 31A is a top view of an embodiment of an exhaust system coupled to an outlet of a pump.

FIG. 31A is a top view of the exhaust system 1370 of FIG. 28A shown coupled to an outlet of a pump 1304, according to some embodiments. The wound dressing 1302 has been removed for purposes of illustration. The pump 1304 includes an inlet 1304a and an outlet 1304b. As shown in FIG. 31A, the exhaust system 1370 can include a connector 1376 including a spacer 1372 enveloped (also referred to as embedded) in a film 1374. In some embodiments, the film 1374 can define a chamber and the spacer 1372 can be positioned within the chamber. The connector 1376 can define a flow path through which gas (e.g., air) exhausted from the pump 1304 can flow through. The flow path can include a portion of the chamber. In some embodiments, the flow path can include the entire chamber. Advantageously, the spacer 1372 can resist collapse of the connector 1376 when the connector 1376 is compressed, thereby inhibiting the flow path of the connector 1376 from becoming occluded. The spacer 1372 can be any suitable 3D material capable of resisting compression in at least one direction, thereby enabling effective transmission of exhaust air therethrough. In some embodiments, the spacer 1372 can be flexible and capable of returning to its original shape after being deformed. In some embodiments, the 3D material can be constructed from antibacterial and/or antimicrobial filter materials so that the pump 1304 can exhaust filtered gases into the atmosphere. In some embodiments, the spacer 1372 can be freely movable within the film 1374. In some embodiments, the spacer 1372 can be freely movable within a chamber defined between top and bottom layers of the film 1374. Any suitably sized spacer 1372 is appreciated.

The film 1374 can be a clear plastic film, although any suitable material is appreciated, such as, for example, a Versapore film having a pore size diameter of about 2 μm. The film 1374 can be flexible. One or more edges of the film 1374 can provide a gas tight seal. The gas tight seal(s) can prevent air from the environment from leaking into the connector 1376. In some embodiments, the film 1374 can include top and bottom layers of a clear plastic film (or other suitable material, e.g., Versapore). One or more edges of the top and bottom layers can be thermally bonded to each other to provide a gas tight seal that can prevent air from the environment from leaking into the connector 1376. It should be appreciated that the gas tight seal along one or more edges (also referred to as one or more portions along a perimeter) of the connector 1376 can be sealed with any suitable process for any suitable film 1374 material. In some embodiments, the spacer 1372 can be freely movable within a chamber defined between the top and bottom layers of the film 1374.

As described above, the connector 1376 can define a flow path through which exhaust gas can flow. For example, in some embodiments, the flow path through the connector 1376 can extend between a first opening 1374a and a second opening 1374b of the film 1374. The portion of the flow path extending between the first and second openings 1374a, 1374b can include one or more channels defined within the connector 1376. In some embodiments, the one or more channels can define a generally tubular flow path that flows around the outside of the spacer 1372 but on the inside of the film 1374. For example, in some embodiments, the one or more channels can be defined by the open space between one or more surfaces (also referred to as sides) of the spacer 1372 and one or more interior surfaces of the film 1374. In some embodiments, the flow path can optionally include at least a portion of the spacer 1372. For example, in some embodiments, the flow path between the first and second openings 1374a, 1374b can extend through a portion of the spacer 1372 (e.g., all of it) in addition to around the spacer 1372. In some embodiments, the spacer 1372 can be positioned within the film 1372 such that the flow path between the first and second openings 1374a, 1374b only flows through the spacer. In some embodiments, the spacer 1372 can be disposed in the flow path to inhibit its occlusion. The second opening 1374b of the connector 1376 can be open to the environment 1390 outside the wound dressing to which the pump 1304 is integrated. The first opening 1374a of the film 1374 can connect to a pump or one or more other exhaust system 1370 features and components. In some embodiments, the first opening 1374a can be positioned on the top of the film 1374. In some embodiments, the first opening 1374a can be positioned through an edge of the film 1374.

In some embodiments, the exhaust system 1370 can optionally include an extension conduit 1380 having any suitable length. The extension conduit 1380 can be used to connect the connector 1376 to a source of negative pressure, such as, for example, the outlet 1304*b* of the pump 1304. Although not shown in FIG. 31A, the length of the extension conduit 1380 can advantageously position the connector 1376 outside of the wound dressing. A first end 1380*a* of the extension conduit 1380 can be coupled to the first opening 1374*a* of the film 1374. In some embodiments, a portion of the extension conduit 1380 can extend (also referred to as inserted) into the connector 1376 through the first opening 1374*a* before being attached to the connector 1376 to advantageously strengthen the attachment between the connector 1376 and the extension conduit 1380. In some embodiments, a portion of the extension conduit 1380 can extend into the connector 1376 and be integrated with the spacer 1372 (e.g., embedded with the spacer 1372). In some embodiments, a portion of the extension conduit 1380 can be enclosed in the spacer 1372. A second end 1380*b* of the extension conduit 1380 can be coupled to the outlet 1304*b* of the pump 1304 to complete the flow path through the exhaust system 1370. Once the extension conduit 1380 is connected to the pump 1304 and the connector 1376 is connected to the extension conduit 1380, the flow path of the exhaust system 1370 can be complete.

In some embodiments, the exhaust system 1370 does not include the optional extension conduit 1380. In such embodiments, the connector 1376 can be connected to the outlet 1304*b* of the pump 1304 such that the flow path of the exhaust system 1370 includes the flow path through the connector 1376.

As discussed above, the spacer 1372 can advantageously inhibit occlusion of the connector 1376. The arrangement of the connector 1376 can also advantageously prevent ingress of water, foreign bodies, dirt, and/or bacteria from getting inside the wound dressing through the flow path of the connector 1376.

The exhaust system 1370 can pass through any suitable location on a wound dressing through an opening in the wound dressing. For example, in some embodiments, a portion of the exhaust system 1370 can pass through a top layer of the wound dressing. As another example, in some embodiments, a portion of the exhaust system 1370 can pass through an edge of the wound dressing (e.g., a border of the wound dressing), such as, for example, between a top layer and a bottom layer of the wound dressing. For example, FIG. 33C is a schematic side view of an end of the exhaust system 1370 between a top layer and a bottom layer of the wound dressing. In some embodiments, the end of the exhaust system between the top and bottom layers can be the connector 1376. In some embodiments, the end of the exhaust system between the top and bottom layers can be the extension conduit 1380. In some embodiments, the top layer can include a moisture vapor permeable film and the bottom layer can include a wound contact layer, although any suitable top and bottom layers are appreciated. The exhaust system 1370 can form a gas tight seal where it passes through the opening in the wound dressing to advantageously prevent the ingress of water, foreign bodies, dirt, and/or bacteria into the wound dressing.

In some embodiments, the exhaust system 1370 include one or more connectors 1376 and zero or more extension conduits 1380.

Figure 31B:
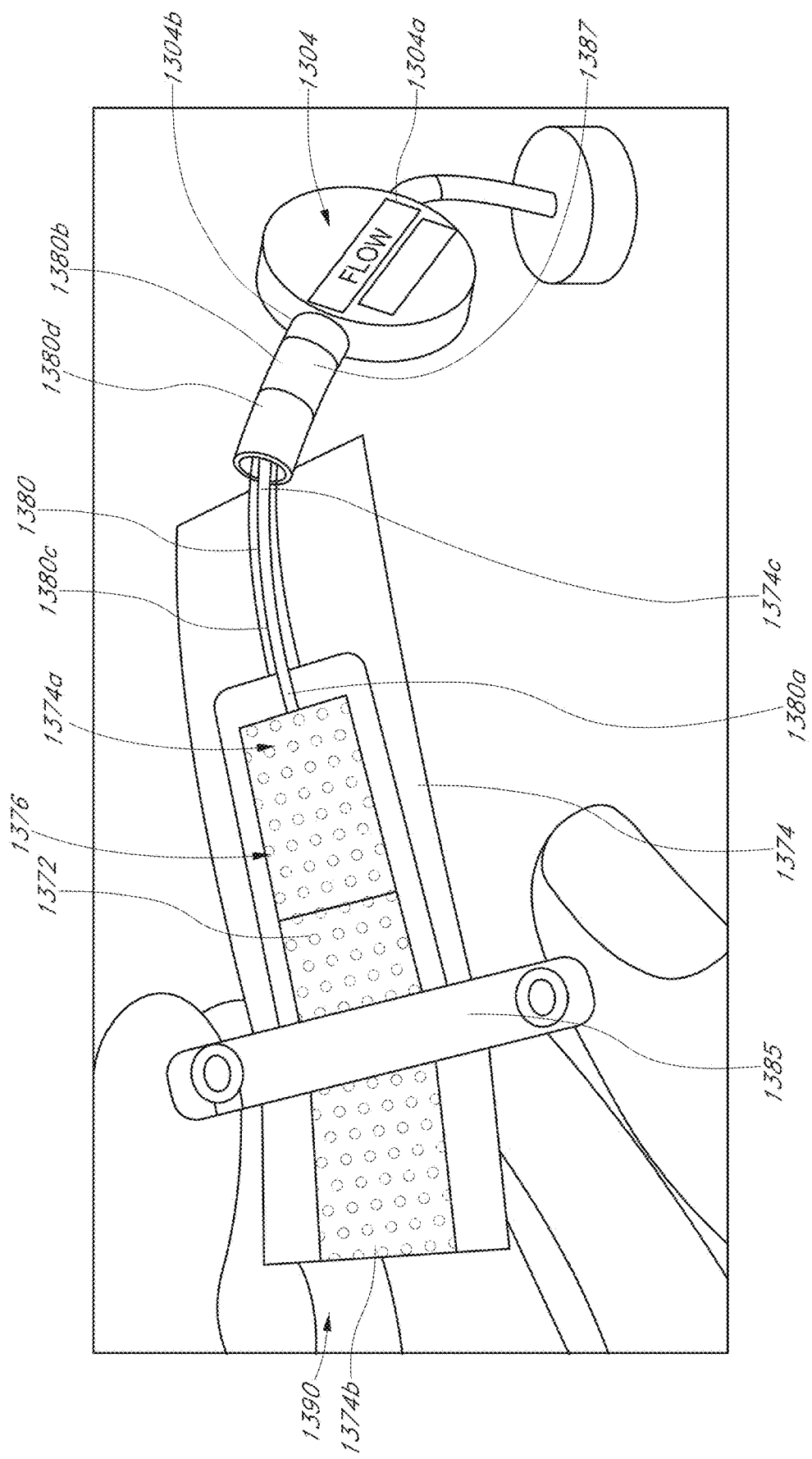
FIG. 31B is a perspective view of an embodiment of the exhaust system coupled to an outlet of a pump.

FIG. 31B is a perspective view of the exhaust system 1370 of FIG. 28A shown coupled to an outlet of a pump, according to some embodiments. Unless otherwise noted, reference numerals and like-named components in FIG. 31B refer to components that are the same as or generally similar to the components of FIGS. 28A and 31A. FIG. 31B is similar to FIG. 31A except a compression source 1385 is clamped to the connector 1376 and the connector 1376 and the extension conduit 1380 have a different arrangement. The compression source 1385 is shown clamped to the connector 1376 to illustrate that the connector 1376 can resist a compression force. The clamp 1385 can be representative, for example, of a patient lying on the connector 1376. In some embodiments, the clamping of the connector 1376, such as with the clamp 1385, can advantageously result in no more than about a 17.5% reduction in flow rate.

As shown in FIG. 31B, in some embodiments, a portion of the extension conduit 1380 can be enveloped by the film 1374. For example, in some embodiments, a distal portion 1380*c* of the extension conduit 1380 can be embedded within the film 1374. In some embodiments, a portion of the extension conduit 1380 can extend into the connector 1376 and attach to a portion of the spacer 1372. In some embodiments, a portion of the extension conduit 1380 can extend into the connector 1376 and be integrated with a portion of the spacer 1372 (e.g., embedded with the spacer 1372). In some embodiments, a proximal portion 1380*d* of the extension conduit 1380 can be covered by one or more connectors, filters, dampeners, and/or insulators 1387.

In yet other embodiments, a portion of the extension conduit 1380 (e.g., an end of the extension conduit 1380) can attach to an edge 1374*c* of the film 1374. In some embodiments, the edge 1374*c* can include the first opening 1374*a* of the film 1374 as described above with reference to FIG. 31A. In such embodiments, reference numeral 1380*c* can instead refer to a flow path defined by the film 1374 instead of a distal portion 1380*c* of the extension conduit 1380. In such embodiments, the flow path defined by the film 1374*c* can open into the region of the connector 1376 containing the spacer 1372.

Figure 32A:
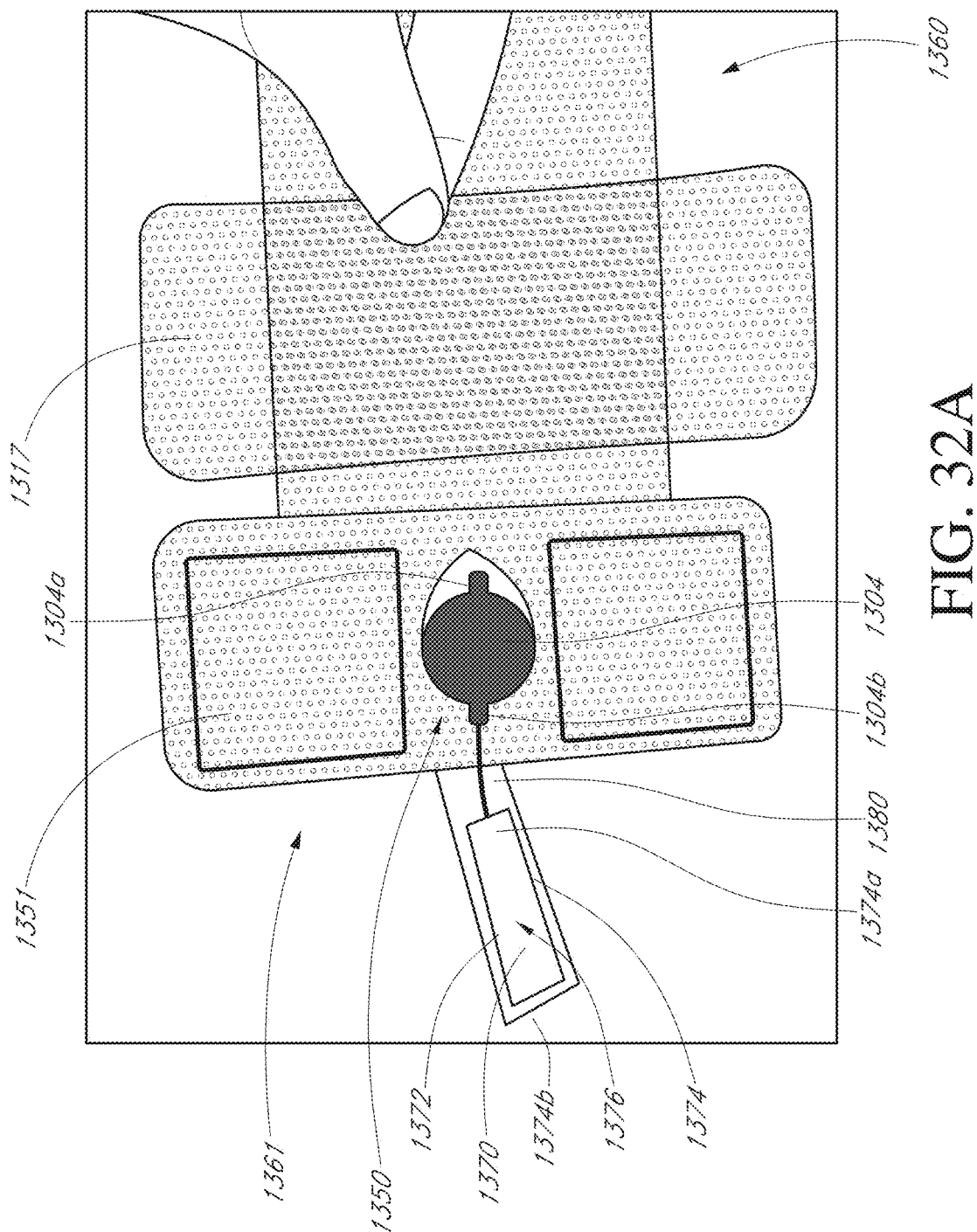
FIGS. 32A and 32B illustrate an embodiment of a wound dressing system with components of the wound dressing system.
Figure 32B:
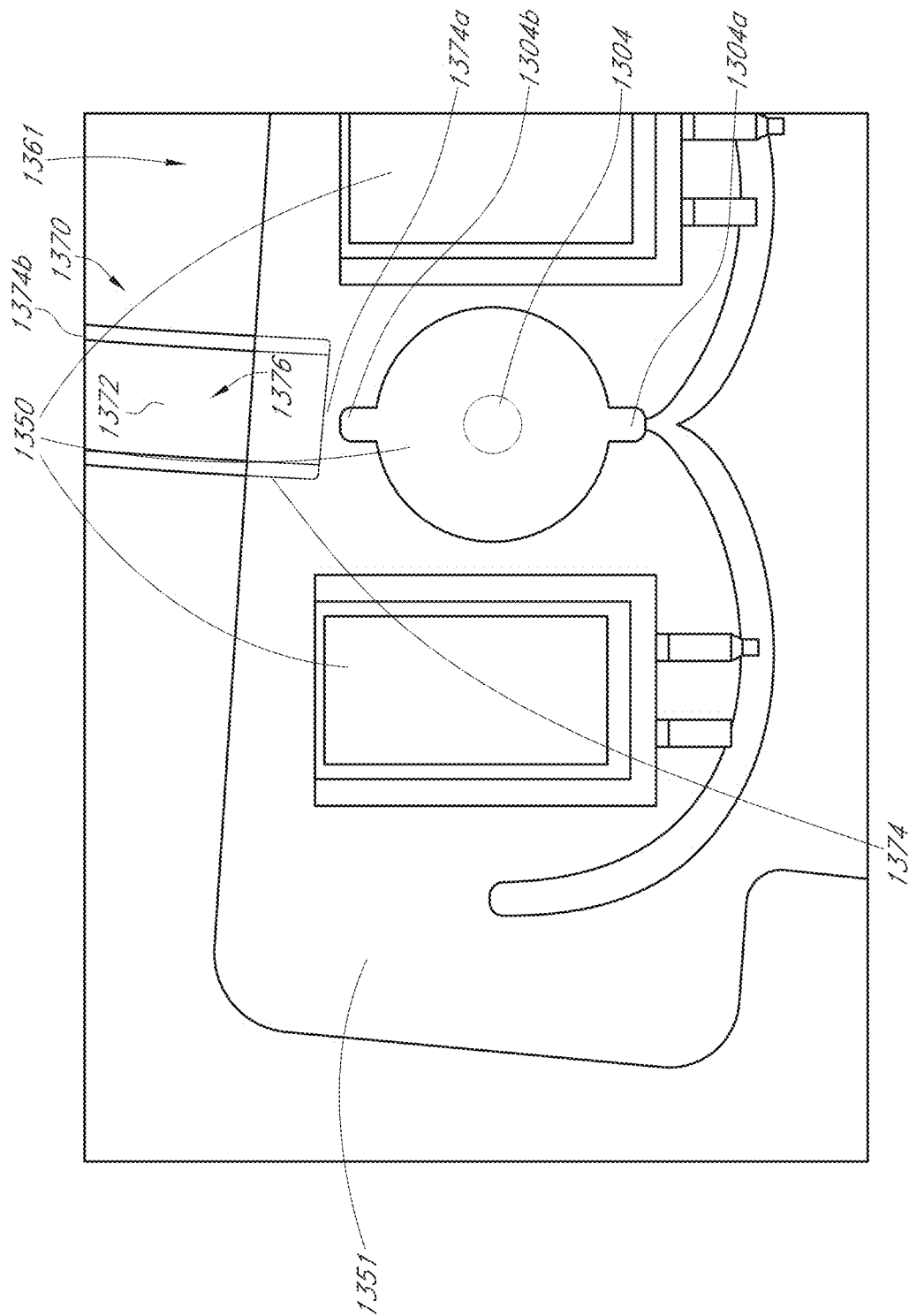

FIGS. 32A and 32B illustrates a wound dressing system with components of the wound dressing system illustrated in FIGS. 18 and 23, respectively. Unless otherwise noted, reference numerals and like-named components in FIGS. 32A and 32B refer to components that are the same as or generally similar to the components of FIGS. 18 and 23, respectively. FIG. 32A shows the dressing with a portion of the top or first spacer layer 1317 over the electronic area folded back and exposing underlying spacer layer 1351 in the electronics area and the electronic components 1350. The exhaust system 1370 is shown coupled to the pump 1304 with the optional extension conduit 1380. In FIG. 32A, the length of the extension conduit 1380 has lengthened the exhaust system 1370 such that the connector 1376 is positioned outside of the wound dressing.

FIG. 32B shows the wound dressing with the electronic components 1350 exposed and the recessed spacer layers removed. FIG. 32B is similar to FIG. 32A except that the exhaust system 1370 in FIG. 32B does not include the optional extension conduit 1380. The exhaust system 1370 of FIG. 32B is coupled to the pump 1304 with the connector 1376.

Figure 33A:
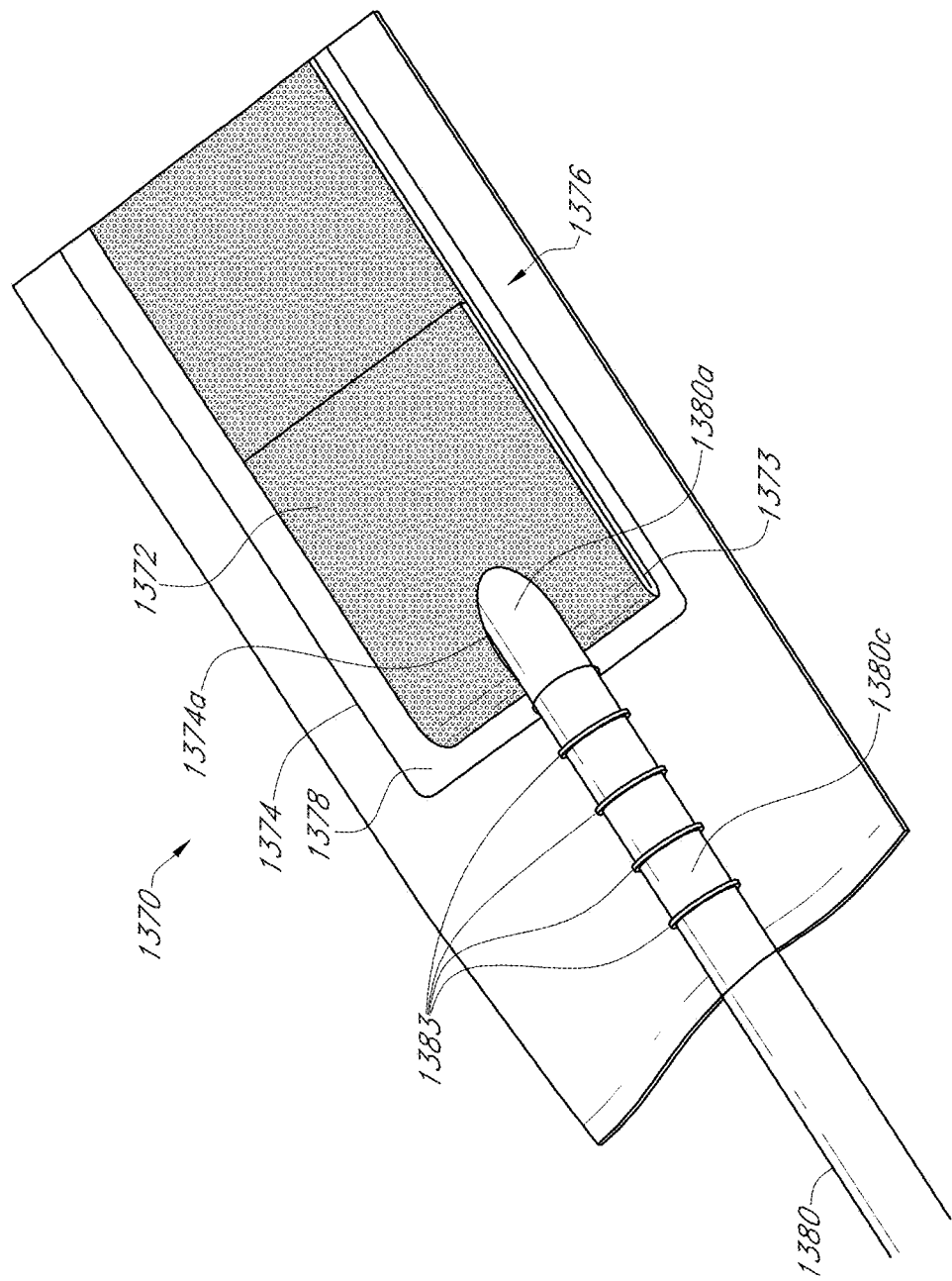
FIG. 33A illustrates an embodiment of a connector and an extension conduit for a wound dressing system.

FIG. 33A is a close up view of the connector 1376 and the extension conduit 1370 of FIG. 31B. Unless otherwise noted, reference numerals and like-named components in FIG. 33A refer to components that are the same as or generally similar to the components of FIGS. 28A and 31A-32B. In some embodiments, the extension conduit 1380 can include one or more ribs 1383, which can act to secure the distal portion of the extension conduit 1380*c* between top and bottom layers of the film 1374 (or in any other suitable fashion). In some embodiments, the one or more ribs 1383 can be circular in shape, although any suitable shape is appreciated. The one or more ribs 1383 can be formed in the extension conduit 1380 by grooves in a mold during the manufacturing of the extension conduit 1380. During thermal bonding of top and bottom layers of the film 1374, for example, melted material from the top and bottom layers can flow around the one or more ribs 1383, advantageously providing a stronger connection between the extension conduit 1380 and the film 1374. As a result, it may be more difficult to dislodge the extension conduit 1380 out from the film 1374 during use of the exhaust system 1370. FIG. 33A also shows that the top and bottom layers of the film 1374 can be joined together so that the film 1374 defines a chamber 1378. The chamber 1378 can house the spacer 1372. In some embodiments, the spacer 1372 can optionally include a fold 1373. The fold 1373 of the spacer 1372 can make the end of the connector 1376 softer and therefore more comfortable for a patient, and can also help prevent the extension conduit 1380 from blockage. The fold 1373 can further protect the end of the extension conduit 1380 (e.g., the first end of the extension conduit 1380a) from being occluded by the top or bottom layers of the film 1374. The fold 1373 can, in some embodiments, be between 1 cm and 3 cm (or between about 1 cm and about 3 cm) long, and in some embodiments is 2 cm (or about 2 cm) long. The spacer 1372 can be folded underneath itself, that is toward a bottom layer of the film 1374, and in some embodiments can be folded upward toward a top layer of the film 1374. In some embodiments, the spacer 1372 may contain no fold.

Figure 33B:
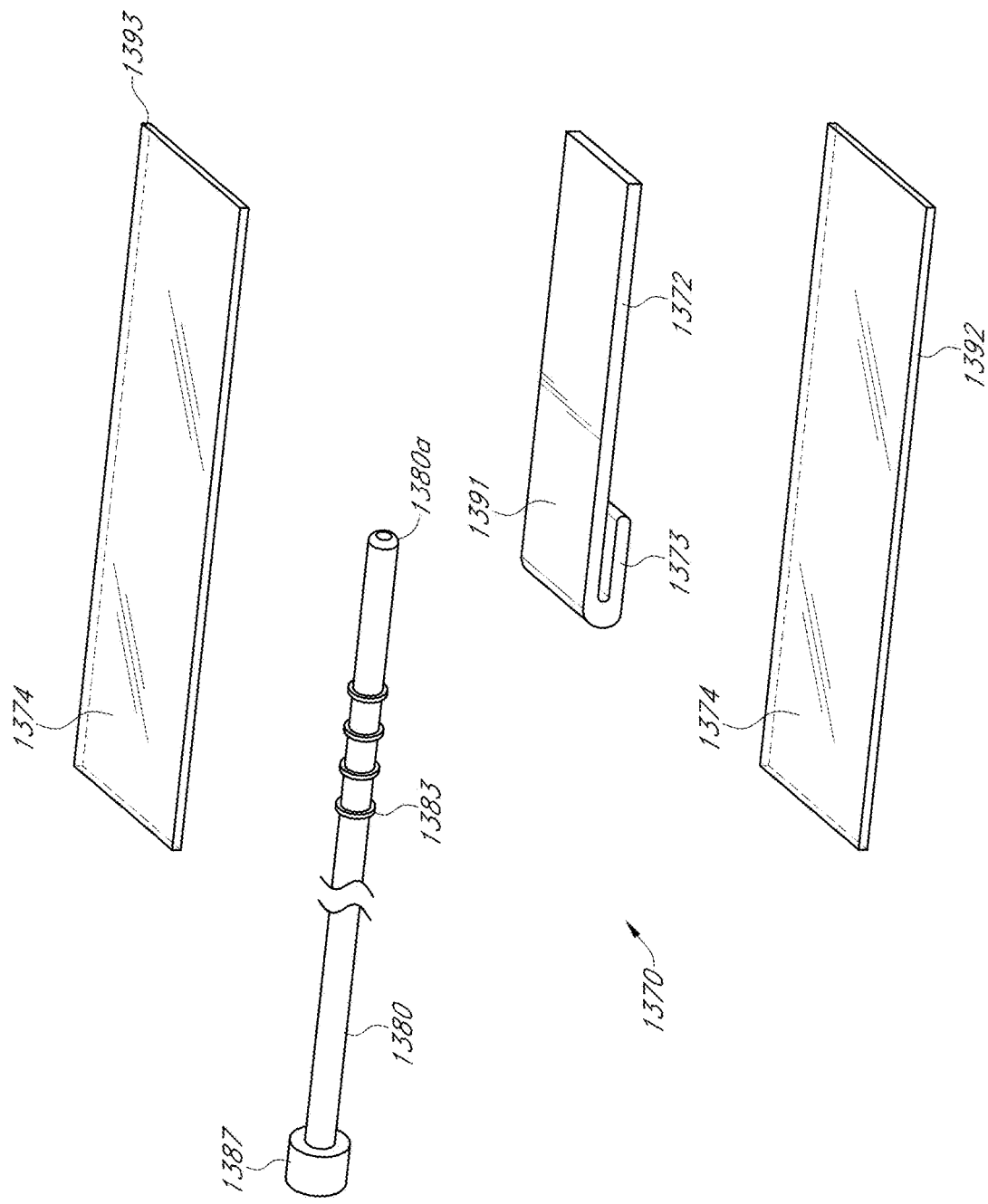
FIG. 33B illustrates a perspective exploded view of an embodiment of the exhaust system of a wound dressing system.
Figure 33C:
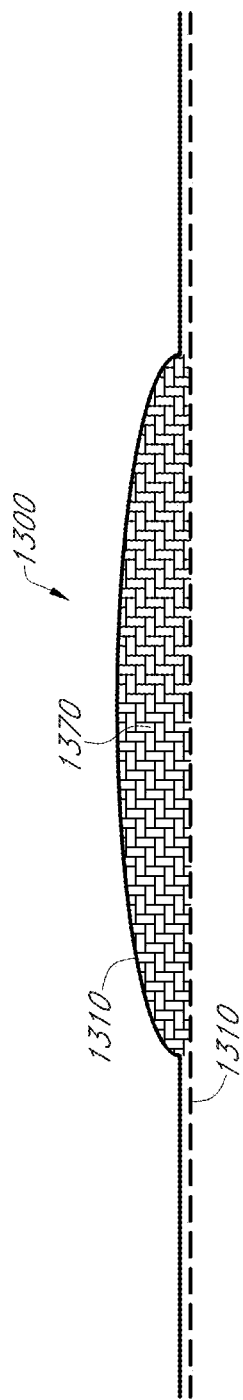
FIG. 33C is a schematic side view of an embodiment of an end of an exhaust system between a top layer and a bottom layer of the wound dressing.

FIG. 33B is a perspective exploded view the exhaust system 1370 of FIG. 33A. As shown in FIG. 33B, the film 1374 can include a top layer 1393 and a bottom layer 1392. In some embodiments, the extension conduit 1380 can optionally include one or more connectors, filters, dampeners, and/or insulators 1387. In some embodiments, a slot (also referred to as a channel) 1391 can extend perpendicularly away from the proximal end of the fold 1373, and the extension conduit 1380 can rest in the slot 1391. In some embodiments, the slot 1391 can extend through one layer of the fold, and in others it can extend through both layers of the fold. The slot 1391 can, in some embodiments, be 1 cm (or about 1 cm) long. Some embodiments can instead employ a circular or elliptical hole in the fold 1373. The hole may face proximally so that the extension conduit 1380 can be inserted into the hole and rest between the folded layers of the spacer 1372. In some embodiments, the extension conduit 1380 can be adhered to the material of the fold 1383, while in other embodiments it may not.

In some embodiments, a portion of the connector 1376 and/or the extension conduit 1380 (e.g., the top and/or bottom layers 1393, 1392 of the film 1374) can include a layer of adhesive, for example a pressure sensitive adhesive, to seal the exhaust system 1370 (e.g., a portion of the exhaust conduit 1380 and/or a portion of the connector 1376) to a wound dressing. For example, in some embodiments, the connector 1376 can be sealed to one or more layers of the wound dressing (e.g., the cover layer, the wound contact layer, and the like).

In some embodiments, the top layer 1393 of the film 1374 can be substantially the same shape as the bottom layer 1392 of the film 1374. In some embodiments, the top layer 1393 and the bottom layer 1392 can be sealed together, for example, by heat welding and/or thermal bonding. In some embodiments, the bottom layer 1392 can be substantially flat and the top layer 1393 can be slightly larger than the bottom layer 1392 in order to accommodate the height of the spacer 1372 and seal to the bottom layer 1392. In other embodiments, the top layer 1393 and the bottom layer 1392 can be substantially the same size, and the layers can be sealed together approximately at the middle of the height of the spacer 1372. In some embodiments, the exhaust system 1370 can have a length in the range of about 0.3 cm to about 10 cm, although any suitable length is appreciated. In some embodiments, the bottom and top layers 1392, 1393 of the film 1374 can include at least one layer of a flexible film, and in some embodiments can be transparent. In some embodiments, the bottom layer 1392 and the top layer 1393 can be polyurethane, and can be liquid impermeable.

As described above, the connector 1376 can include a spacer 1372, such as the 3D fabric discussed above, positioned between the lower layer 1392 and the top layer 1393 of the film 1374. The spacer 1372 can be made of any suitable material, for example material resistant to collapsing in at least one direction, thereby enabling effective transmission of exhaust air therethrough. Instead of or in addition to the 3D fabric discussed above, some embodiments of the spacer 1372 can comprise a fabric configured for lateral wicking of fluid, which may comprise viscose, polyester, polypropylene, cellulose, or a combination of some or all of these, and the material may be needle-punched. Some embodiments of the spacer 1372 can comprise polyethylene in the range of 40-160 grams per square meter (gsm) (or about 40 to about 160 gsm), for example 80 (or about 80) gsm. Such materials may be constructed so as to resist compression.

As shown in FIG. 28A, the wound dressing system 1300 can include a non-return valve 1410 to inhibit the back flow (also referred to as back leakage) of air into the wound dressing system 1300. For example, in some embodiments, the non-return valve 1410 can inhibit the back flow of air (e.g., from the environment) into the wound dressing system 1300 through the pump 1304. As described in more detail below, the non-return valve 1410 can allow fluid flow in a first direction but inhibit fluid flow in a second direction, such as, for example, a second direction opposite the first direction, although any two directions are appreciated. In some embodiments, the non-return valve 1410 can be fluidically coupled to a portion of a flow path which extends between an outlet of the pump 1304 and the environment. Such an arrangement can advantageously allow the wound dressing system 1300 to deliver a more stable target pressure to a wound site by inhibiting back flow that would otherwise cause the target pressure to be more varied. A non-return valve 1410 in fluid communication with the outlet of the pump 1304 can also advantageously make the pump more efficient by reducing the amount of power the pump consumes while it is drawing down and/or maintaining the dressing at a given target pressure.

As shown in FIG. 28A, in some embodiments, the flow path between the outlet of the pump 1304 and the environment can include an exhaust system 1370 to exhaust air from the pump 1304 to the outside of the wound dressing 1302 (e.g., to the environment). The non-return valve 1410 can be, for example, positioned in the flow path between the pump 1304 and the exhaust system 1370, although it should be appreciated that the non-return valve 1410 can be positioned in any suitable portion of the flow path that extends between the pump 1304 and the environment. For example, in some embodiments, the non-return valve 1410 can be positioned on the inlet side of the pump between the wound dressing 1302 and an inlet to the pump 1304. The exhaust system 1370 can be similar to the exhaust system described in detail herein with reference to FIGS. 31A-33C. In some embodiments, the non-return valve 1410 can be optionally connected to the pump 1304 and/or the exhaust system 1370. The non-return valve 1410 can be, for example, fitted (also referred to as connected or coupled) to the outlet of the pump 1304 and/or at least partially disposed in the pump 1304 (e.g., the outlet of the pump 1304). Although not shown in FIG. 28A, in some embodiments, the non-return valve 1410 can optionally be integrated with the exhaust system 1370. For example, in some embodiments, the non-return valve 1410 can be positioned at the inlet or outlet of the exhaust system 1370 or be incorporated within it. As another example, in some embodiments, the wound dressing system 1300 may optionally not include the exhaust system 1370 altogether.

In some embodiments, the non-return valve 1410 can optionally be integrated with the wound dressing 1302 and/or with one or more embedded electronic components 1350 (e.g., the pump 1304). The non-return valve 1410 can be, for example, sufficiently small to fit within the dimensional constraints of the wound dressing 1302. In some embodiments, the non-return valve 1410 can be optionally positioned within and/or embedded in the wound dressing 1302, such as, for example, in the electronics area 1361. To fit within the wound dressing 1302, the non-return valve 1410 can have any suitable size and shape. For example, in some embodiments, the non-return valve 1410 can have a height that is less than a thickness of the wound dressing 1302 (e.g., a thickness between the cover layer 1313 and the wound contact layer 1310). As another example, in some embodiments, the non-return valve 1410 can have a length that is less than a length of the electronics area 1361 of the wound dressing 1302.

So that the non-return valve 1410 can inhibit back flow while also efficiently allowing for out flow through the wound dressing system 1300, the non-return valve 1410 can advantageously have a low cracking pressure and a low resistance to out flow. A low cracking pressure and a low resistance to out flow can advantageously decrease the amount of power consumed during operation of the pump 1304 by decreasing the amount of resistance the pump 1304 must overcome to exhaust air. The use of a non-return valve 1410 can decrease the leak rate (also referred to as back flow) of the wound dressing system 1300 more than it decreases the pump rate of the wound dressing system 1300. For example, in some embodiments, using the non-return valve 1410 can result in a total leak rate reduction of about 8.4% compared to a total pump rate reduction of about 7%, thereby resulting in an energy savings of approximately 1.4% from the use of the non-return valve 1410 alone. In some embodiments, the cracking pressure of the non-return valve 1410 can range from about 350 Pa to 500 Pa for a flow rate of about 1 mL/min (e.g., a flow rate of exactly 1 mL/min), although any suitable cracking pressure is appreciated (and at any suitable flow rate), such as, for example, about 100 Pa, 250 Pa, 400 Pa, 550 Pa, or less than about 1,000 Pa for flow rates of about 1 mL/min, among others (e.g., any suitable cracking pressure between 0 Pa and 1,000 Pa). The cracking pressure according the aforementioned values corresponds to the threshold pressure drop to open and reseal of the non-return valve 1410 for air flows having rate of about 1 mL/min. It should be appreciated that any other standardized flow rates can be used as well. In some embodiments, the non-return valve 1410 may not decrease the flow rate through the pump by more than 100 mL/min. For example, in some embodiments, the non-return valve 1410 can decrease the flow rate through the pump between approximately 9.5 mL/min and approximately 24.5 mL/min, although other values of 100 mL/min or less are also appreciated. In some embodiments, the non-return valve 1410 can have an out flow resistance in the range of about 5.0 mL/min to about 30 mL/min (measured with a nominally fixed vacuum of 10.7 kPa below atmosphere), although any suitable out flow resistance is appreciated, such as, for example, an out flow resistance of about 9.5 mL/min to about 24.5 mL/min, an out flow resistance of about 9.5 mL/min, an out flow resistance of about 14.6 mL/min, an out flow resistance of about 24.5 mL/min, and an out flow resistance of less than about 100 mL/min, among others (as measured with a nominally fixed vacuum of 10.7 kPa below atmosphere). In some embodiments, the non-return valve 1410 does not prevent all back flow. For example, in some embodiments, the non-return valve 1410 can allow a negligible amount of air to leak into the wound dressing system 1300 through the outlet of the pump 1304. For example, in some embodiments, the leakage rate of the non-return valve 1410 can be negligible such that the pump 1304 and the non-return valve 1410 have a combined leak rate of about 10.0 mL/min or less, such as, for example, 1.0 mL/min or less, 2.0 mL/min or less, 3.0 mL/min or less, 4.0 mL/min or less, or 5.0 mL/min or less. In some embodiments, the wound dressing system 1300 can establish a target vacuum in 50 seconds or less with a non-return valve 1410 incorporated with the wound dressing 1302 and/or the exhaust system 1370. For example, in some embodiments, the wound dressing system 1300 can establish a target vacuum in about 5.1 seconds to 8.9 seconds, although any suitable time is appreciated.

Figure 34B:
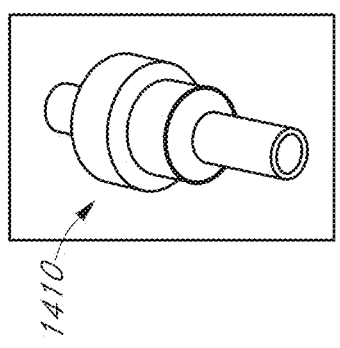
FIGS. 34A-34D illustrate embodiments of various views of duckbill non-return valves.
Figure 34D:
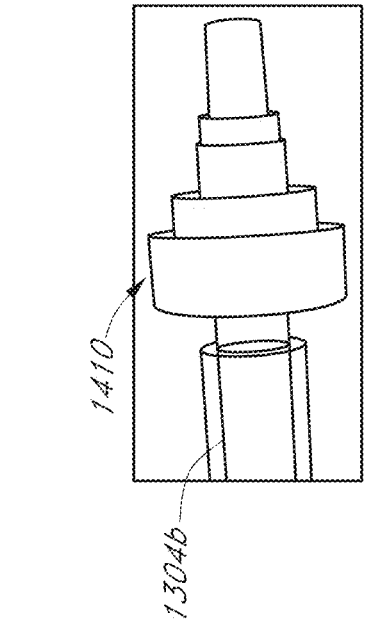
Figure 34A:
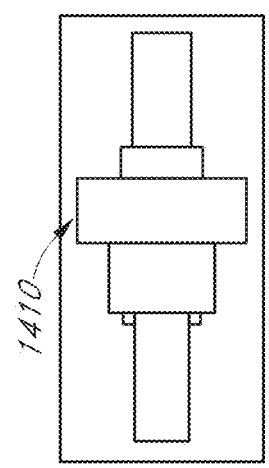
Figure 34C:
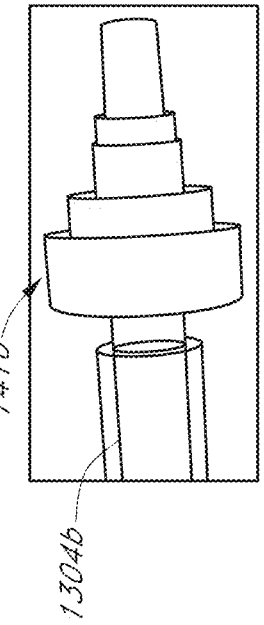
Figure 35C:
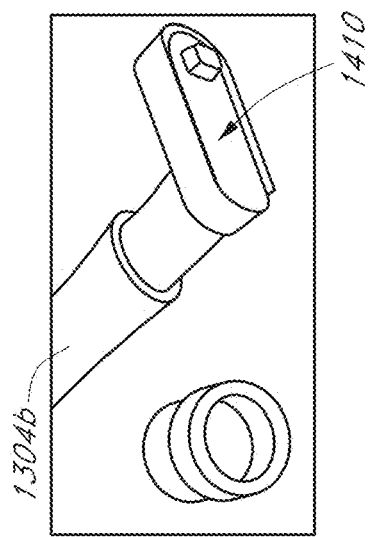
FIGS. 35A-35C illustrate various views of embodiments of various reed valves coupled to a pump outlet.
Figure 35B:
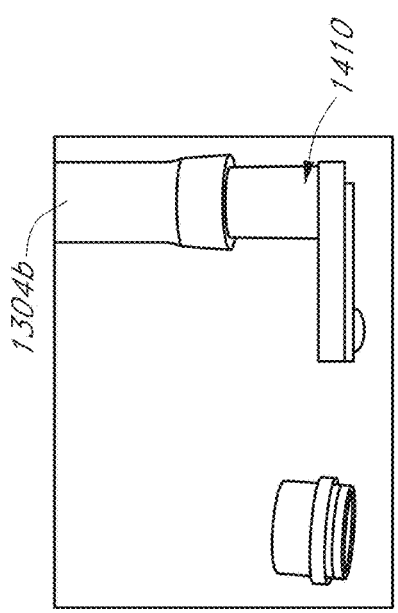
Figure 35A:
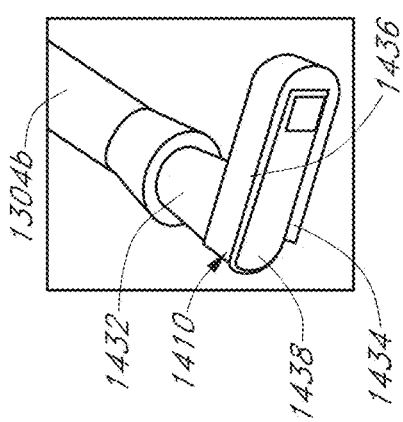

The non-return valve 1410 positioned in the out flow path of the wound dressing system 1300 can be a mechanical self-activated valve that does not need and/or use power to operate. For example, in some embodiments, the non-return valve 1410 can be a reed valve or a duckbill valve, although any suitable mechanical one-way valve is appreciated, such as, for example, a ball valve or an umbrella valve, among others. Various views of duckbill non-return valves 1410 are illustrated in FIGS. 34A-34D, with FIGS. 34C and 34D showing the duckbill valve 1410 coupled to a pump outlet 1304b. FIGS. 35A-35C illustrate various views of various reed valves 1410 coupled to a pump outlet 1304b. For example, FIG. 35A shows a reed valve 1410 having a cavity 1434 with an inlet port 1432 and an outlet port 1436 and a reed 1438 at least partially disposed in the cavity 1434. The reed 1438 of the reed valve 1410 can occlude the flow path between the pump 1304 and the environment such that it allows fluid flow in a first direction (e.g., away from the pump) but inhibits fluid flow in a second direction (e.g., toward the pump). For example, in some embodiments, the reed 1438 can act as an encastered beam, with one end fixed and another end free to deflect. The sensitivity of the reed 1438 can be increased by increasing its length (i.e., longer reeds can be more sensitive than shorter reeds). For example, all else being equal, longer reeds can have lower cracking pressures and lower out flow resistances. In some embodiments, the reed 1438 can have a length in the range of about 3.0 mm to about 30 mm (e.g., as measured from the center of the non-return valve hole is seals to its opposite end). For example, in some embodiments, the reed 1438 has a length of about 10.5 mm, although any suitable length is appreciated. In some embodiments, the reed valve 1410 can be a 75 micron thick polyester reed valve, although any suitable thickness and material is appreciated.

As shown in FIGS. 35A-35C, the shape of the non-return valve 1410 can be rectangular with two rounded ends. However, it will be understood that other suitable shapes can be provided. For example, FIGS. 36A-36C illustrate various views of a non-return valve 1410 having a crescent shape that can advantageously facilitate integration of the non-return valve 1410 into a wound dressing (e.g., wound dressing 1302 shown in FIG. 28A). For example, the crescent shape can advantageously reduce the size of the non-return valve 1410 and make the wound dressing system 1300 more compact. As another example, the crescent shape can advantageously facilitate the attachment of the top surface 1440a to a cover layer (not shown, but see cover layer 1313 in FIG. 28A). For example, the curved top surface 1440a of the crescent shape can help achieve a seal with the cover layer. The crescent shape can also advantageously streamline the upper surface of the wound dressing system in which it is incorporated by softening the edges of the non-return valve, thereby making the wound dressing system more comfortable to the user and at the same time making it less bulky. The upper curved surface 1440a of the non-return valve 1410 can also reduce the likelihood of the non-return valve 1410 from becoming snagged by better deflecting objects that come into contact with it. Note that unless otherwise specified, reference numerals in FIGS. 36A-36C refer to components that are the same as or generally similar to the components of FIGS. 28A and 34A-35C. FIGS. 36B and 36C further illustrate a crescent shaped non-return valve 1410 positioned adjacent a pump 1304. In some embodiments, the inlet port 1432 of the non-return valve can be coupled to the pump outlet 1304b.

Further, although FIGS. 36B and 36C illustrate a non-return valve 1410 having a crescent shape with an upper curved surface which intersects a lower flat surface, any suitable crescent shape is appreciated. For example, in some embodiments, the lower flat surface can have a curve which conforms to the surface of a wound site. In such embodiments, the radius of curvature of the upper surface can be less than the radius of curvature of the lower surface so that the two surfaces intersect. In some embodiments, the housing of the non-return valve 1410 can be made of a rigid, semi-rigid, and/or flexible material. For example, in some embodiments, the upper and lower surfaces of the non-return valve can be semi-rigid. As another example, in some embodiments, the lower surface of the non-return valve 1410 can be less rigid than the upper surface so that the lower surface can better conform to the surface of a wound site. The non-return valve 1410 can be made from any suitable material. In addition, for non-return valve embodiments including a reed, the reed can have a curved portion that fits inside the crescent shape of the non-return valve 1410 housing to advantageously make the non-return valve 1410 more compact.

Although not shown in FIGS. 34A-36C, the non-return valve 1410 can be positioned between the wound contact layer and the cover layer such that a bottom surface of the non-return valve 1410 sits on the wound contact layer and a top surface of the non-return valve 1410 sits under the cover layer (e.g., wound contact layer 1310 and cover layer 1313 in FIG. 28A). In some embodiments, the non-return valve 1410 can be sealed to the wound dressing 1302 and/or the exhaust system 1370 with an oil seal.

Figure 37:
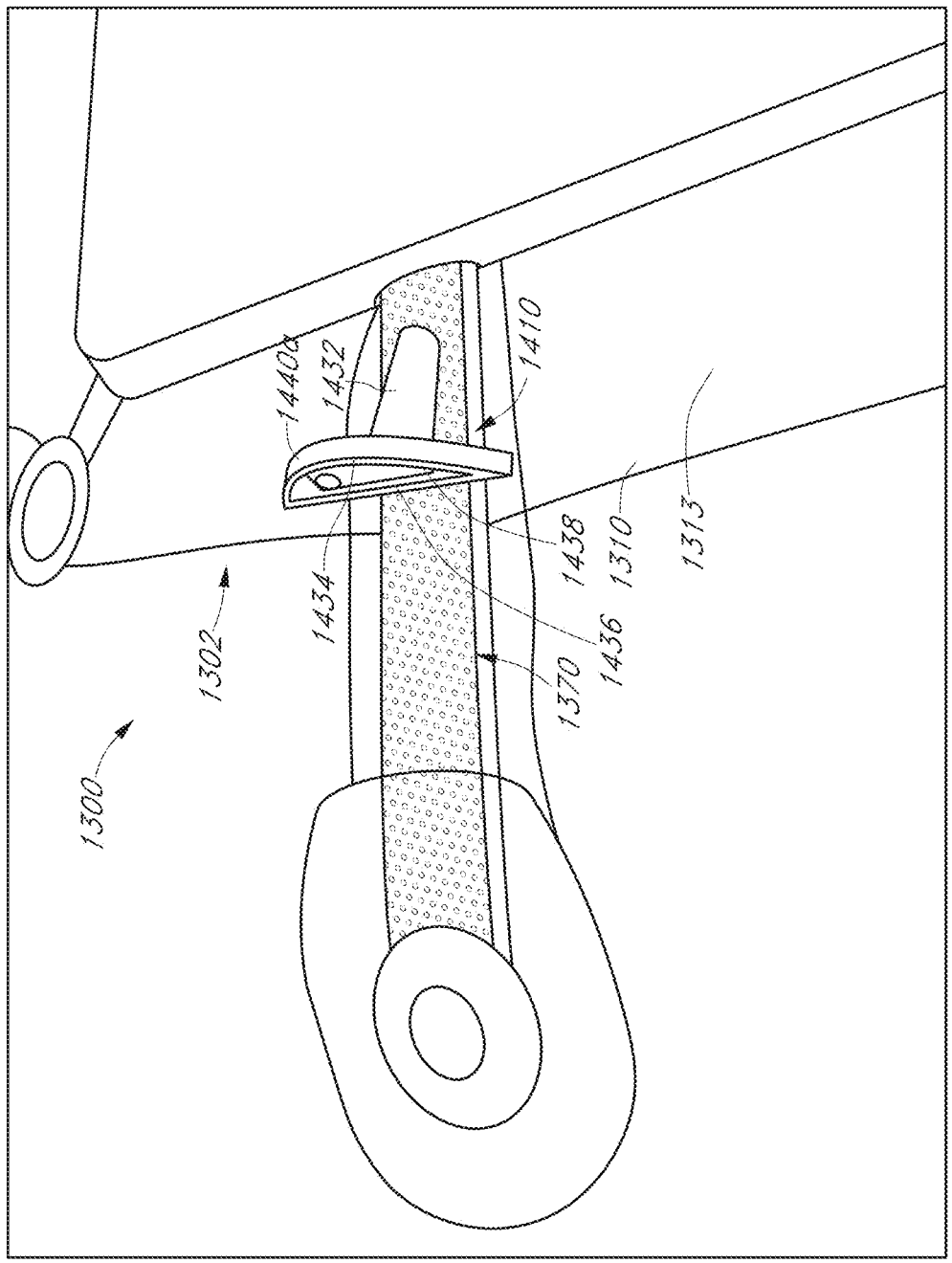
FIG. 37 illustrates an embodiment of a crescent shaped non-return valve positioned superficially above an exhaust system and a wound dressing.

FIG. 37 illustrates a crescent shaped non-return valve 1410 positioned superficially above an exhaust system 1370 and a wound dressing 1302. As described above, in some embodiments, the non-return valve 1410 can be integrated with the exhaust system 1370 and be positioned between the wound contact layer 1310 and the cover layer 1313. In some embodiments, the inlet port 1432 of the non-return valve 1410 can be fluidically coupled to the outlet of the pump (not shown) and the outlet port 1436 of the non-return valve 1410 can be fluidically coupled to an inlet of the exhaust system 1370 (not shown). In some embodiments, the non-return valve 1410 can be integrated with the exhaust system 1370 beyond the border of the wound dressing 1302 (i.e., external to the wound dressing 1302).

Figure 38B:
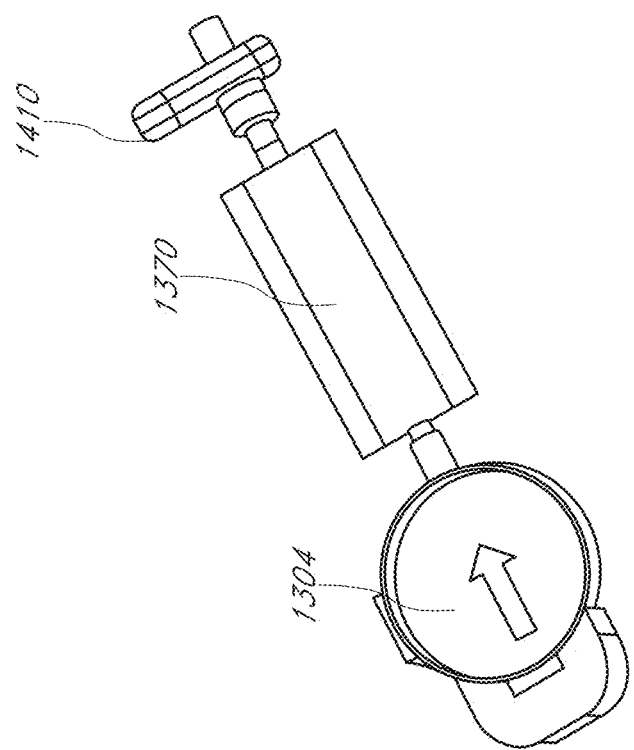
FIGS. 38A-38E illustrate various positions of an embodiment of a non-return valve in relation to a pump and an exhaust system.
Figure 38A:
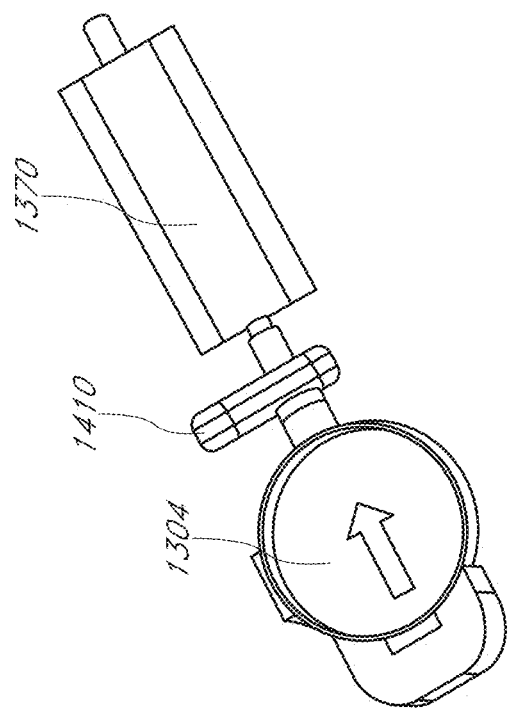
Figure 38D:
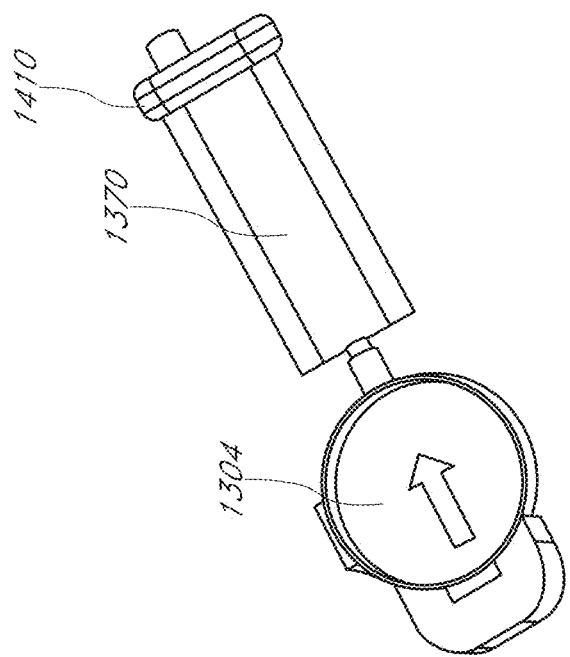
Figure 38C:
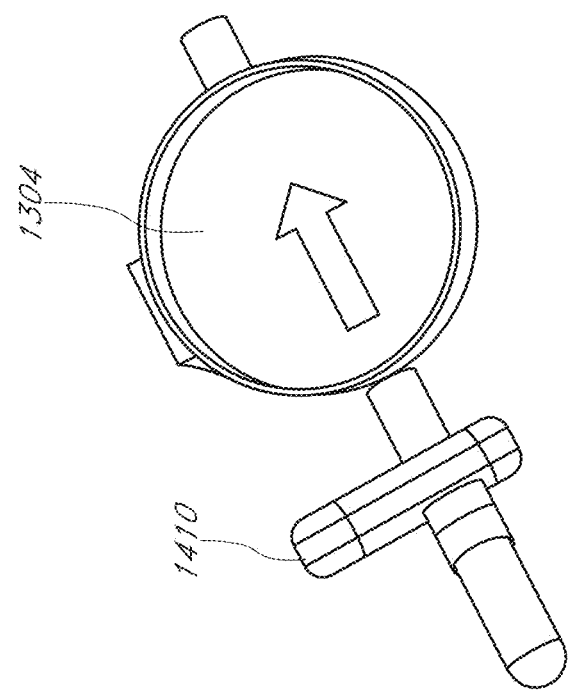
Figure 38E:
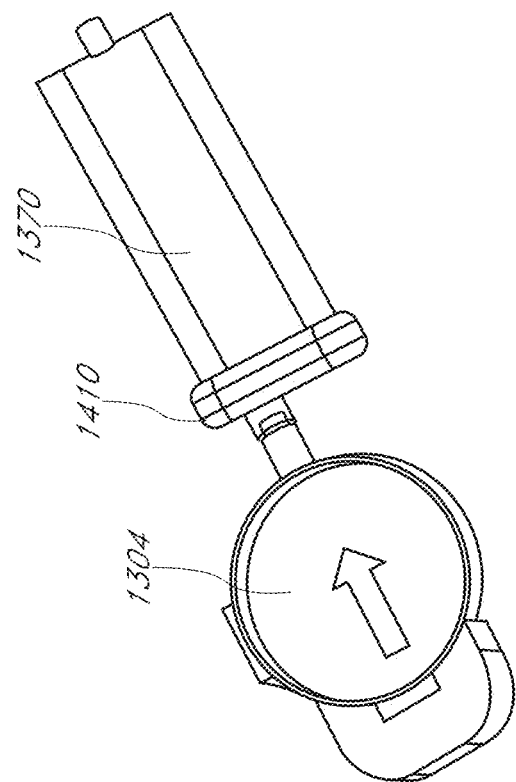

FIGS. 38A-38E illustrate various positions of a non-return valve 1410 in relation to a pump 1304 and an exhaust system 1370. FIG. 38A illustrates a non-return valve 1410 positioned between a pump 1304 and an exhaust system 1370. For example, in some embodiments, the non-return valve 1410 can be fluidically coupled to an outlet of the pump 1304 and an inlet of the exhaust system 1370. In some embodiments, the non-return valve 1410 can be fluidically coupled to an outlet of the exhaust system (e.g., so that the exhaust system 1370 is interposed between the non-return valve 1410 and the pump 1304). FIG. 38B illustrates a non-return valve 1410 positioned after an exhaust system 1370. For example, in some embodiments, the non-return valve 1410 can be fluidically coupled to an outlet of the exhaust system 1370. FIG. 38C illustrates a non-return valve 1410 positioned between an inlet (not labeled) and a pump 1304. For example, in some embodiments, the non-return valve 1410 can be fluidically coupled to an inlet of the wound dressing and an inlet of the pump 1304. As another example, FIG. 38C illustrates a non-return valve 1410 integrated with an inlet of a pump 1304. FIG. 38D illustrates a non-return valve 1410 positioned after a pump 1304 and integrated with an outlet of an exhaust system 1370. FIG. 38E illustrates a non-return valve 1410 positioned after a pump 1304 and integrated with an inlet of an exhaust system 1370. The non-return valves 1410 illustrated in FIGS. 38A-38E are shown as having a rectangular shape with circular ends. However, it will be understood that the non-return valves 1410 in FIGS. 38A-38E can have any suitable shape, such as, for example, a crescent shape, among any other suitable shape. The non-return valve 1410 and/or the exhaust system 1370 in FIGS. 38A, 38B, 38D, and 38E can be wholly or partially positioned within or external to a dressing border (not shown). A portion of the non-return valve 1410 and/or the exhaust system 1370 in FIGS. 38A, 38B, 38D, and 38E can be wholly or partially integrated within a wound dressing (not shown). In some embodiments, the pump inlet can include a fluid ingress inhibition component in fluid communication with the pump. The component can allow gas (e.g., air) but inhibit liquid (e.g., wound exudate) from passing through. The component can provide a plurality of flow paths between an interior of the wound dressing 1302 and the pump 1304 so that occlusion (e.g., from wound exudate) of the pump 1304 is inhibited. Examples of such applications where additional disclosure relating to the preceding may be found include U.S. Provisional Application No. 62/327,676, titled "Fluid Ingress Inhibition Component for Reduced Pressure Apparatuses," filed on Apr. 26, 2016, the disclosure of which is hereby incorporated by reference in its entirety.

Figure 39A:
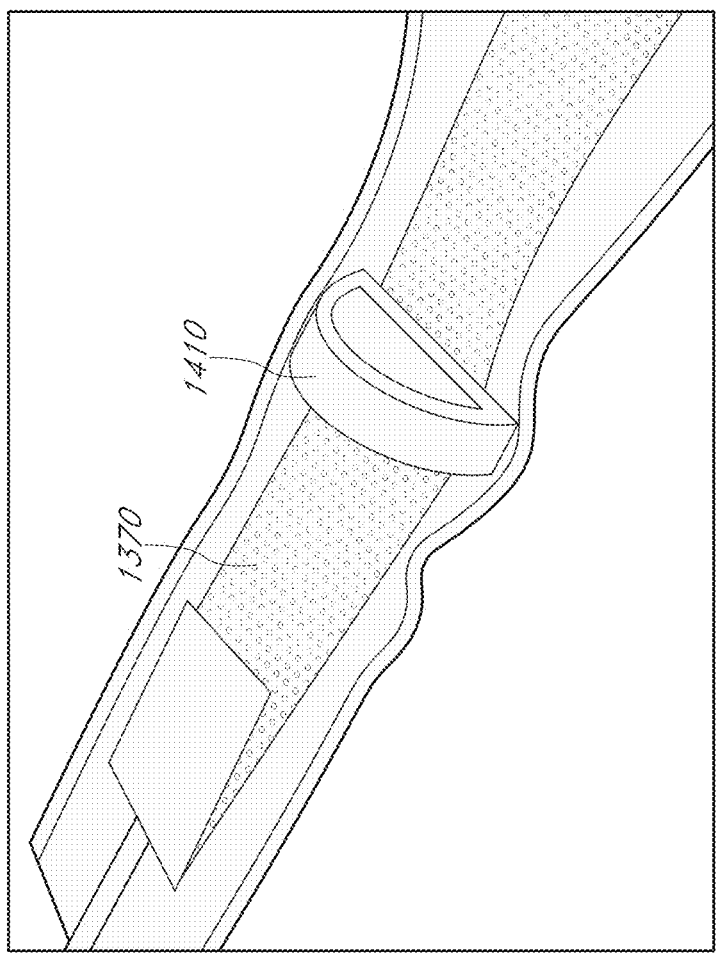
FIGS. 39A-39B illustrate two positions of an embodiment of a crescent-shaped non-return valve in relation to an exhaust system.
Figure 39B:
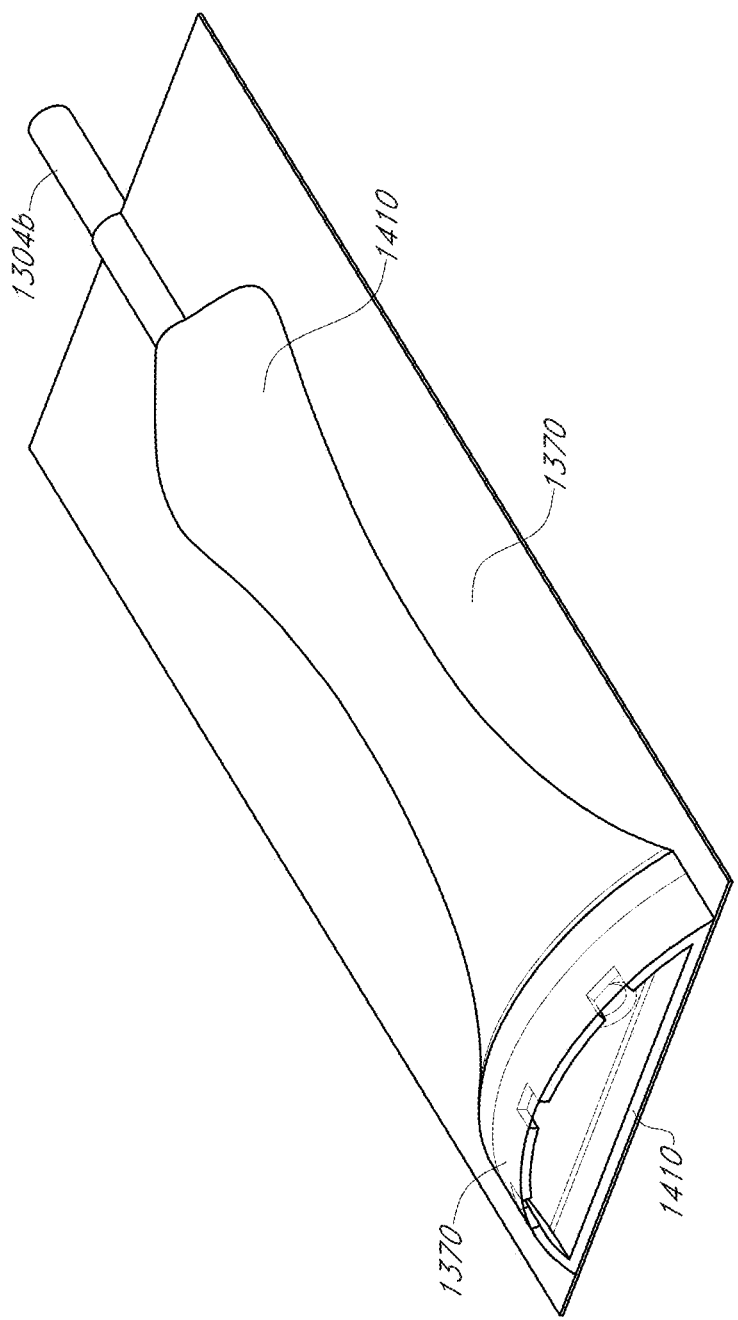

FIGS. 39A and 39B illustrate two positions of a crescent-shaped non-return valve 1410 in relation to an exhaust system 1370. FIG. 39A illustrates a non-return valve 1410 having a crescent shape integrated with an exhaust system 1370. For example, in some embodiments, the non-return valve 1410 can be fluidically coupled and integrated with an exhaust system 1370 somewhere between an inlet and an outlet of the exhaust system 1370. FIG. 39B illustrates a non-return valve 1410 having a crescent shape positioned after a pump (not shown) and integrated with an outlet of an exhaust system 1370. For example, in some embodiments, the exhaust system 1370 can be fluidically coupled to an outlet 1304b of the pump. The non-return valves 1410 illustrated in FIGS. 39A-39B are shown as having a crescent shape. However, it will be understood that the non-return valves 1410 in FIGS. 39A-39B can have any suitable shape, such as, for example, a rectangular shape with circular ends, among any other suitable shape.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A wound dressing apparatus comprising:
    a wound dressing configured to be positioned over a wound site, the wound dressing comprising a wound contact layer configured to be positioned in contact with the wound site, an absorbent layer, and a cover layer configured to cover and form a seal over the wound contact layer and the absorbent layer;
    a negative pressure source disposed on or positioned within the wound dressing, the negative pressure source comprising an inlet and an outlet and being operable to apply negative pressure to the wound site; and
    a non-return valve enclosure positioned within the wound dressing and in fluid communication with the outlet, the non-return valve enclosure comprising a non-return valve being configured to inhibit back flow of air into the wound dressing, the non-return valve enclosure comprising a cavity with an inlet port and an outlet port.

2. The wound dressing apparatus of claim 1, wherein the non-return valve is configured to inhibit back flow of air into the wound dressing through the outlet.

3. The wound dressing apparatus of claim 1, wherein the inlet port is configured to be fluidically coupled to the outlet of the negative pressure source.

4. The wound dressing apparatus of claim 1, wherein the non-return valve enclosure is at least partially disposed in the outlet.

5. The wound dressing apparatus of claim 1, wherein the non-return valve enclosure is integrated with the wound dressing.

6. The wound dressing apparatus of claim 1, wherein the non-return valve enclosure is positioned within and/or embedded in the wound dressing.

7. The wound dressing apparatus of claim 1, wherein the non-return valve enclosure is sized to fit within the wound dressing.

8. The wound dressing apparatus of claim 1, wherein the non-return valve enclosure has a height that is less than a thickness of the wound dressing.

9. The wound dressing apparatus of claim 1, wherein the non-return valve is a mechanical valve that is self-activated.

10. The wound dressing apparatus of claim 1, wherein the non-return valve comprises a duckbill valve.

11. The wound dressing apparatus of claim 1, wherein the non-return valve comprises a reed valve.

12. The wound dressing apparatus of claim 11, wherein the non-return valve comprises a reed at least partially disposed in the cavity.

13. The wound dressing apparatus of claim 1, wherein the non-return valve enclosure comprises a crescent shape.

14. The wound dressing apparatus of claim 13, wherein the crescent shape is defined by a housing having a first curved surface that intersects a second surface.

15. The wound dressing apparatus of claim 14, wherein the second surface is flat.

16. The wound dressing apparatus of claim 14, wherein the second surface is curved, the second surface having a radius of curvature that is greater than a radius of curvature of the first curved surface.

17. The wound dressing apparatus of claim 14, wherein the second surface is semi-rigid or flexible such that it is configured to conform to a surface of the wound site.

18. The wound dressing apparatus of claim 11, wherein the non-return valve enclosure comprises a crescent shape, wherein the reed comprises a rectangular shape with circular ends.

19. The wound dressing apparatus of claim 11, wherein the non-return valve enclosure comprises a crescent shape, wherein the reed includes a curved portion.

20. The wound dressing apparatus of claim 1, wherein the negative pressure source is a micro pump.

21. The wound dressing apparatus of claim 1, wherein the outlet port is covered by the non-return valve.

* * * * *